US009546214B2

(12) United States Patent
Reyes et al.

(10) Patent No.: US 9,546,214 B2
(45) Date of Patent: Jan. 17, 2017

(54) HUMANIZED ANTIBODIES THAT BIND LGR5

(71) Applicant: Bionomics Inc., San Diego, CA (US)

(72) Inventors: Christopher L. Reyes, San Diego, CA (US); Peter Chu, San Diego, CA (US); Kristen M. Smith, San Clemente, CA (US); Lioudmila A. Campbell, Del Mar, CA (US); Farbod Shojaei, San Diego, CA (US); John Thomas Norton, San Diego, CA (US)

(73) Assignee: Bionomics, Inc., San Diego, CA (US)

( * ) Notice: Subject to any disclaimer, the term of this patent is extended or adjusted under 35 U.S.C. 154(b) by 0 days.

(21) Appl. No.: 14/677,815

(22) Filed: Apr. 2, 2015

(65) Prior Publication Data
US 2016/0031984 A1 Feb. 4, 2016

Related U.S. Application Data

(60) Provisional application No. 62/081,497, filed on Nov. 18, 2014, provisional application No. 61/975,589, filed on Apr. 4, 2014.

(51) Int. Cl.
| | | |
|---|---|---|
| *C07K 16/28* | (2006.01) | |
| *A61K 39/395* | (2006.01) | |
| *C07K 16/30* | (2006.01) | |
| *A61K 45/06* | (2006.01) | |
| *A61K 39/00* | (2006.01) | |

(52) U.S. Cl.
CPC ......... *C07K 16/28* (2013.01); *A61K 39/39558* (2013.01); *A61K 45/06* (2013.01); *C07K 16/30* (2013.01); *A61K 2039/505* (2013.01); *C07K 2317/21* (2013.01); *C07K 2317/24* (2013.01); *C07K 2317/33* (2013.01); *C07K 2317/34* (2013.01); *C07K 2317/73* (2013.01); *C07K 2317/732* (2013.01)

(58) Field of Classification Search
CPC ..... C07K 16/30; C07K 16/28; C07K 2317/24; A61K 39/39558
USPC ..................................... 424/142.1; 530/387.2
See application file for complete search history.

(56) References Cited

U.S. PATENT DOCUMENTS

| | | | |
|---|---|---|---|
| 4,444,887 A | 4/1984 | Hoffmann | |
| 4,474,893 A | 10/1984 | Reading | |
| 4,676,980 A | 6/1987 | Segal et al. | |
| 4,714,681 A | 12/1987 | Reading | |
| 4,716,111 A | 12/1987 | Osband et al. | |
| 4,741,900 A | 5/1988 | Alvarez et al. | |
| 4,816,397 A | 3/1989 | Boss et al. | |
| 4,816,567 A | 3/1989 | Cabilly et al. | |
| 4,925,648 A | 5/1990 | Hansen | |
| 4,946,778 A | 8/1990 | Ladner et al. | |
| 5,112,946 A | 5/1992 | Maione | |
| 5,122,464 A | 6/1992 | Wilson et al. | |
| 5,223,409 A | 6/1993 | Ladner et al. | |
| 5,225,539 A | 7/1993 | Winter | |
| 5,258,498 A | 11/1993 | Huston et al. | |
| 5,314,995 A | 5/1994 | Fell et al. | |
| 5,336,603 A | 8/1994 | Capon et al. | |
| 5,349,053 A | 9/1994 | Landolfi | |
| 5,359,046 A | 10/1994 | Capon et al. | |
| 5,403,484 A | 4/1995 | Ladner et al. | |
| 5,413,923 A | 5/1995 | Kucherlapati et al. | |
| 5,427,908 A | 6/1995 | Dower et al. | |
| 5,447,851 A | 9/1995 | Beutler et al. | |
| 5,474,981 A | 12/1995 | Leder et al. | |
| 5,516,637 A | 5/1996 | Huang et al. | |
| 5,530,101 A * | 6/1996 | Queen ................... | C07K 16/00 424/133.1 |
| 5,545,806 A | 8/1996 | Lonberg et al. | |
| 5,545,807 A | 8/1996 | Surani et al. | |
| 5,565,332 A | 10/1996 | Hoogenboom et al. | |
| 5,569,825 A | 10/1996 | Lonberg et al. | |
| 5,571,698 A | 11/1996 | Ladner et al. | |
| 5,573,920 A | 11/1996 | Randle | |
| 5,580,717 A | 12/1996 | Dower et al. | |
| 5,585,089 A | 12/1996 | Queen et al. | |
| 5,591,669 A | 1/1997 | Krimpenfort et al. | |
| 5,601,819 A | 2/1997 | Wong | |
| 5,605,793 A | 2/1997 | Stemmer | |
| 5,612,205 A | 3/1997 | Kay et al. | |
| 5,622,929 A | 4/1997 | Willner et al. | |

(Continued)

FOREIGN PATENT DOCUMENTS

| | | |
|---|---|---|
| EP | 0239400 | 9/1987 |
| EP | 0367166 | 5/1990 |
| EP | 0396387 | 11/1990 |
| EP | 0413622 | 2/1991 |
| EP | 0439095 | 7/1991 |
| EP | 0519596 | 12/1992 |
| WO | WO 86/05807 | 10/1986 |
| WO | WO 88/07089 | 9/1988 |
| WO | WO 89/01036 | 2/1989 |
| WO | WO 89/12624 | 12/1989 |
| WO | WO 90/02809 | 3/1990 |
| WO | WO 91/00360 | 1/1991 |
| WO | WO 91/06570 | 5/1991 |
| WO | WO 91/09967 | 7/1991 |

(Continued)

OTHER PUBLICATIONS

Sasaki et al. (Biochem. Biopys. Res. Commun. 394:498-502 (2010)).*

(Continued)

*Primary Examiner* — Lynn Bristol
(74) *Attorney, Agent, or Firm* — Knobbe, Marens, Olson & Bear LLP

(57) ABSTRACT

Disclosed herein are humanized anti-LGR5 antibodies for the treatment of cancer. Antibodies disclosed herein may bind LGR5 without disrupting LGR5-RSPO1 binding or signaling, and may disrupt LGR5 signaling through Wnt that is independent of RSPO1. Also disclosed are heavy and light chain polypeptide sequences for the biding of LGR5, for example without disrupting LGR5-RSPO binding or signaling.

19 Claims, 19 Drawing Sheets

(56) References Cited

U.S. PATENT DOCUMENTS

| | | |
|---|---|---|
| 5,624,821 A | 4/1997 | Winter et al. |
| 5,625,126 A | 4/1997 | Lonberg et al. |
| 5,633,425 A | 5/1997 | Lonberg et al. |
| 5,643,763 A | 7/1997 | Dunn et al. |
| 5,648,260 A | 7/1997 | Winter et al. |
| 5,658,727 A | 8/1997 | Barbas et al. |
| 5,658,759 A | 8/1997 | Bebbington |
| 5,661,016 A | 8/1997 | Lonberg et al. |
| 5,677,425 A | 10/1997 | Bodmer et al. |
| 5,698,426 A | 12/1997 | Huse |
| 5,714,350 A | 2/1998 | Co |
| 5,721,367 A | 2/1998 | Kay et al. |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,789,208 A | 8/1998 | Sharon |
| 5,789,215 A | 8/1998 | Berns et al. |
| 5,789,650 A | 8/1998 | Lonberg et al. |
| 5,807,715 A | 9/1998 | Morrison et al. |
| 5,811,238 A | 9/1998 | Stemmer et al. |
| 5,814,318 A | 9/1998 | Lonberg et al. |
| 5,821,047 A | 10/1998 | Garrard et al. |
| 5,827,739 A | 10/1998 | Wilson et al. |
| 5,830,721 A | 11/1998 | Stemmer et al. |
| 5,834,252 A | 11/1998 | Stemmer et al. |
| 5,837,458 A | 11/1998 | Minshull et al. |
| 5,869,046 A | 2/1999 | Presta et al. |
| 5,874,299 A | 2/1999 | Lonberg et al. |
| 5,877,397 A | 3/1999 | Lonberg et al. |
| 5,879,936 A | 3/1999 | Bebbington et al. |
| 5,885,573 A | 3/1999 | Bluestone et al. |
| 5,885,793 A | 3/1999 | Griffiths et al. |
| 5,916,771 A | 6/1999 | Hori et al. |
| 5,939,598 A | 8/1999 | Kucherlapati et al. |
| 5,969,108 A | 10/1999 | McCafferty et al. |
| 5,981,175 A | 11/1999 | Loring et al. |
| 5,981,216 A | 11/1999 | Kenten et al. |
| 6,023,010 A | 2/2000 | Krimpenfort et al. |
| 6,121,022 A | 9/2000 | Presta et al. |
| 6,165,745 A | 12/2000 | Ward et al. |
| 6,194,551 B1 | 2/2001 | Idusogie et al. |
| 6,255,458 B1 | 7/2001 | Lonberg et al. |
| 6,277,375 B1 | 8/2001 | Ward |
| 6,335,163 B1 | 1/2002 | Sharon |
| 6,350,861 B1 | 2/2002 | Co |
| 6,737,056 B1 | 5/2004 | Presta et al. |
| 6,821,505 B2 | 11/2004 | Ward |
| 8,680,243 B2 | 3/2014 | Funahashi |
| 9,220,774 B2* | 12/2015 | Reyes .................. C07K 16/28 |
| 9,221,906 B2* | 12/2015 | Reyes ............. A61K 39/39558 |
| 9,221,907 B2* | 12/2015 | Reyes .................. C07K 16/28 |
| 2003/0153043 A1 | 8/2003 | Carr et al. |
| 2003/0190311 A1 | 10/2003 | Dall'Acqua et al. |
| 2004/0002587 A1 | 1/2004 | Watkins et al. |
| 2011/0318339 A1 | 12/2011 | Smider et al. |
| 2012/0316071 A1 | 12/2012 | Smider et al. |
| 2013/0336885 A1 | 12/2013 | Hongo et al. |
| 2014/0147383 A1 | 5/2014 | Funahashi |
| 2014/0256041 A1* | 9/2014 | Reyes ............. A61K 39/39558 435/375 |
| 2014/0302049 A1* | 10/2014 | Chu ...................... C07K 16/28 424/139.1 |
| 2014/0302054 A1* | 10/2014 | Reyes .................. C07K 16/28 424/143.1 |
| 2015/0037324 A1* | 2/2015 | Reyes ............. A61K 39/39558 424/133.1 |
| 2016/0031984 A1* | 2/2016 | Reyes .................. C07K 16/30 424/133.1 |
| 2016/0046723 A1* | 2/2016 | Reyes .................. C07K 16/30 424/139.1 |

FOREIGN PATENT DOCUMENTS

| | | |
|---|---|---|
| WO | WO 91/10737 | 7/1991 |
| WO | WO 91/10741 | 7/1991 |
| WO | WO 91/14438 | 10/1991 |
| WO | WO 92/01047 | 1/1992 |
| WO | WO 92/03918 | 3/1992 |
| WO | WO 92/05793 | 4/1992 |
| WO | WO 92/08495 | 5/1992 |
| WO | WO 92/08802 | 5/1992 |
| WO | WO 92/18619 | 10/1992 |
| WO | WO 92/22324 | 12/1992 |
| WO | WO 92/22645 | 12/1992 |
| WO | WO 92/22647 | 12/1992 |
| WO | WO 92/22670 | 12/1992 |
| WO | WO 93/11236 | 6/1993 |
| WO | WO 93/12227 | 6/1993 |
| WO | WO 93/15199 | 8/1993 |
| WO | WO 93/15200 | 8/1993 |
| WO | WO 93/17715 | 9/1993 |
| WO | WO 93/21232 | 10/1993 |
| WO | WO 94/00569 | 1/1994 |
| WO | WO 94/25585 | 11/1994 |
| WO | WO 95/15982 | 6/1995 |
| WO | WO 95/20401 | 8/1995 |
| WO | WO 96/04388 | 2/1996 |
| WO | WO 96/14436 | 5/1996 |
| WO | WO 96/33735 | 10/1996 |
| WO | WO 96/34096 | 10/1996 |
| WO | WO 97/13852 | 4/1997 |
| WO | WO 97/34631 | 9/1997 |
| WO | WO 98/16654 | 4/1998 |
| WO | WO 98/24884 | 6/1998 |
| WO | WO 98/24893 | 6/1998 |
| WO | WO 98/46645 | 10/1998 |
| WO | WO 98/50433 | 11/1998 |
| WO | WO 99/54342 | 10/1999 |
| WO | WO 99/58572 | 11/1999 |
| WO | WO 00/42072 | 7/2000 |
| WO | WO 02/060919 | 8/2002 |
| WO | WO 03/035835 | 5/2003 |
| WO | WO 03/075957 | 9/2003 |
| WO | WO 2004/009618 | 1/2004 |
| WO | WO 2004/029207 | 4/2004 |
| WO | WO 2004/003019 * | 6/2004 |
| WO | WO 2005/089285 | 9/2005 |
| WO | WO 2009/005809 | 1/2009 |
| WO | WO 2010/016766 | 2/2010 |
| WO | WO 2013/067054 | 5/2013 |
| WO | WO 2013/067055 | 5/2013 |
| WO | WO 2013/067057 | 5/2013 |
| WO | WO 2013/067060 | 5/2013 |

OTHER PUBLICATIONS

Walker et al. PLoS One 6(7): e22733. doi:10.1371/journal.pone.0022733.*
Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*
Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Chen et al., "The structural basis of R-spondin recognition by LGR5 and RNF43" *Genes Dev.* 27(12):1345-50 (2013).

(56) References Cited

OTHER PUBLICATIONS

International Search Report and Written Opinion issued in PCT/US2015/024162 dated Aug. 20, 2015.
Karlin et al., "Applications and statistics for multiple high-scoring segments in molecular sequences" Proc. Natl. Acad. Sci. USA, 90:5873-5877 (1993).
Kemper, et al, "Monoclonal Antibodies Against Lgr5 identify Human Colorectal Cancer Stem Cells," Stem Cells, 30:2378-2386 (2012).
Kostelny et al., "Formation of a Bispecific Antibody by the Use of Leucine Zippers" J. Immunol. 148:1547-1553 (1992).
Schaffer et al., "Improving the accuracy of PSI-BLAST protein database searches with composition-based statistics and other refinements" Nucleic Acids Res., 29:2994-3005 (2001).
Tutt, et al., "Trispecific F(ab')$_3$ Derivatives that use Cooperative Signaling via the TCR/CD3 Complex and CD2 to Activate and Redirect Resting Cytotoxic T Cells" J. Immunol. 147:60-69 (1991).
Armour, K.L. et al., Recombinant human IgG molecules lacking Fcgamma receptor I binding and monocyte triggering activities, EurJ Immunol 1999, 29:2613-2624.
Ashkenazi A. et al., Protection against endotoxic shock by a tumor necrosis factor receptor immunoadhesin. PNAS USA, Dec. 1991; 88:10535-10539.
Ausubel F.M. et al., Current Protocols in Molecular Biology, John Wiley & Sons, Inc. TOC, pp. 15.
Barker N. et al., Identification of stem cells in small intestine and colon by marker gene Lgr5, Nature Oct. 2007;449:1003-1008.
Becker, L. et al., Immunostaining of Lgr5, an Intestinal Stem Cell Marker, in Normal and Premalignant Human Gastrointestinal Tissue, ScientificWorldJournal. Nov. 2008; 23(8):1168-1176.
Better, M. et al., *Escherichia coli* Secretion of an Active Chimeric Antibody Fragment, Science May 1988; 240:1041-1043.
Bebbington C.R. et al.,[Eds], The use of vectors based on gene amplification for the expression of cloned genes in mammalian cells in DNA cloning, (Academic Press, New York, 1987) vol. 8; pp. 163-188.
Carmon, KS. et al., R-spondins function as ligands of the orphan receptors LGR4 and LGR5 to regulate Wnt/beta-catenin signaling, Proc Natl Acad Sci U S A. Jul. 12, 2011;108(28):11452-7.
Clackson T. et al., Making antibody fragments using phage display libraries. Nature Aug. 1991; 352:624-628.
Cockett et al., High level expression of tissue inhibitor of metalloproteinases in Chinese Hamster ovary cells using glutamine synthetase gene amplification, Bio/Technology (1990) 8:662-667.
Colbère-Garapin; F. et al., A new dominant hybrid selective marker for higher eukaryotic cells. J Mol Biol. Jul. 1981; 150(1):1-14.
Crouse G.F. et al., Expression and Amplification of Engineered Mouse Dihydrofolate Reductase Minigenes. Mol Cell Biol. Feb. 1983; 3(2):257-266.
De Lau, W. et al., Lgr5 homologues associate with Wnt receptors and mediate R-spondin signaling, Nature. Jul. 4, 2011; 476(7360):293-7-1.
DeNardo G.L. et al., Comparison of 1,4,7,10-tetraazacyclododecane-N,N',N'',N'''—tetraacetic acid (DOTA)-peptide-ChL6, a novel immunoconjugate with catabolizable linker, to 2-iminothiolane-2-[p-(bromoacetamido)benzyl]-DOTA-ChL6 in breast cancer xenografts; Clin Cancer Res. Oct. 1998; 4(10):2483-2490.
Dontu G. et al., In vitro propagation and transcriptional profiling of human mammary stem/progenitor cells. Genes Dev. May 2003; 17(10):1253-1270.
Dracopoli N.C. et al., [Eds.] Current Protocols in Human Genetics, John Wiley & Sons, 157; N.Y. 1994; Chapters 12 and 13; pp. 390. [uploaded in 2-part document].
Duncan, A.R. et al., Localization of the binding site for the human high-affinity Fc receptor on IgG, Nature Apr. 7, 1988; 332(6164):563-4.
Fan, X-S et al., Expression of Lgr5 in human colorectal carcinogenesis and its potential correlation with beta-catenin, Int J Colorectal Dis. 2010; 25:583-590.

Fell H.P. et al., Genetic construction and characterization of a fusion protein consisting of a chimeric F(ab') with specificity for carcinomas and human IL-2. J Immunol. Apr. 1991; 146(7):2446-2452.
Foecking M.K. et al., Powerful and versatile enhancer-promoter unit for mammalian expression vectors. Gene 1986; 45(1):101-105.
Garnett M.C., Targeted drug conjugates: Principles and Progress. Adv Drug Deliv Rev. 2001; 53(2):171-216.
Gentz R. et al., Bioassay for trans-activation using purified human immunodeficiency virus tat-encoded protein: Trans-activation requires mRNA synthesis. PNAS USA. Feb. 1989; 86:821-824.
Ghetie, V. et al., Increasing the serum persistence of an IgG fragment by random mutagenesis. Nat Biotechnol. Jul. 1997; 15(7):637-640.
Gillies et al., High-level expression of chimeric antibodies using adapted cDNA variable region cassettes. J. Immunol. Methods Dec. 1989; 125(1-2):191-202.
Gillies: S.D. et al., Antibody-targeted interleukin 2 stimulates T-cell killing of autologous tumor cells. PNAS USA. Feb. 1992; 89:1428-1432.
Green L.L. et al., Regulation of B Cell Development by Variable Gene Complexity in Mice Reconstituted with Human Immunoglobulin Yeast Artifical Chromosomes. J Exp Med. Aug. 1998; 188(3):483-495.
Greenspan N.S. et al., Idiotypes: Structure and Immunogenicity. FASEB J. 1989;7(5):437-444.
Hämmerling G.J. et al., [Eds.] "Production of Antibody-Producing Hybridomas in the Rodent Systems" in: Monoclonal Antibodies and T-Cell Hybridomas—Perspectives and technical advances. (Elsevier, N.Y., 1981) pp. 563-681.
Hansson L.O. et al., Evolution of Differential Substrate Specificities in Mu Class Glutathione Transferases Probed by DNA Shuffling. J Mol Biol. 1999; 287:265-276.
Harayama S., Artificial evolution by DNA shuffling, Trends Biotechnol. 1998; 16(2): 76-82.
Harlow, E. et al., Antibodies: A Laboratory Manual, Cold Spring Harbor Laboratory 1988; 2nd Ed., TOC 9 pages.
Hellstrom et al., "Antibodies for Drug Delivery", in Controlled Drug Delivery (2nd Ed.), Robinson et al. (eds.); (Marcel Dekker, Inc. 1987); Chapter 15; pp. 623-653.
Huston, J.S. et al., Protein engineering of single-chain Fv analogs and fusion proteins, Methods Enzymol. 1991; 203:46-88.
Hutchins, J.T. et al., Improved biodistribution, tumor targeting, and reduced immunogenicity in mice with a gamma 4 variant of Campath-1H, Proc Natl Acad Sci. USA Dec. 1995; 92:11980-11984.
Idusogie, E.E. et al., Mapping of the C1q Binding Site on Rituxan, A Chimeric Antibody with a Human IgG1 Fc, J Immunol. 2000, 164:4178-4184.
Idusogie, E.E. et al., Engineered Antibodies with Increased Activity to Recruit Complement, J Immunol. 2001,166:2571-2575.
Inouye S. et al., Up-promoter mutations in the lpp gene of *Escherichia coli*. Nuc Acids Res. 1985; 13(9):3101-3110.
Jefferis R. et al., Recognition sites on human IgG for Fc gamma receptors: the role of glycosylation, Immunol Lett. Jan. 1995; 44(2-3):111-117.
Jefferis R. et al., Modulation of FcGammaR and human complement activation by IgG3-core oligosaccharide interactions. Immunol Lett. 1996; 54:101-104.
Jefferis R. et al., Interaction sites on Human IgG-Fc for FcGammaR: current models, Immunol Lett. 2002, 82(1-2):57-65.
Jespers L.S. et al., Guiding the selection of human antibodies from phage display repertoires to a single epitope of an antigen. Bio/Technology 1994; 12:899-903.
Jones: P.T. et al., Replacing the complementarity—determining regions in a human antibody with those from a mouse. Nature May 1986; 321:522-525.
Kriegler M., Gene Transfer and Expression: A Laboratory Manual. Stockton Press, NY; 184: :1990; TOC; pp. 5.
Kleist B. et al., Expression of the adult intestinal stem cell marker Lgr5 in the metastatic cascade of colorectal cancer, Int J Clin Exp Pathol. 2011; 4(4):327-335.

(56) References Cited

OTHER PUBLICATIONS

Kobayashi, S. et al., Lgr5-positive colon cancer stem cells interconvert with drug-resistant LGR5-negative cells and are capable of tumor reconstitution, Stem Cells. Dec. 2012;30(12):2631-44.
Köhler G., Immunoglobulin chain loss in hybridoma lines. PNAS USA, Apr. 1980; 77(4):2197-2199.
Liu et al., Hedgehog Signaling and Bmi-1 Regulate Self-renewal of Normal and Malignant Human Mammary Stem Cells. Can Res. Jun. 2006; 66(12):6063-6071.
Logan J. et al., Adenovirus tripartite leader sequence enhances translation of mRNAs late after infection. PNAS, USA Jun. 1984; 81:3655-3659.
Lonberg N. et al., Antigen-specific human antibodies from mice comprising four distinct genetic modifications. Nature 1994; 368:856-859.
Lonberg N. et al., Human antibodies from transgenic mice. Int Rev Immunol. 1995;13(1):65-93.
Lorenzo M. et al. "PCR-Based Method for the Introduction of Mutations in Genes Cloned and Expressed in Vaccinia Virus", Biotechniques 1998; 24(2): 308-313.
Lund, J. et al., Human FcGammaRi and FcGammaRii interact with distinct but overlapping sites on human IgG, J Immunol. 1991; 147(8): 2657-2662.
Lund, J. et al., Multiple binding sites on the CH2 domain of IgG for mouse FcGammaR11, Mol Immunol. Jan. 1992; 29(1):53-9.
J. et al., Oligosaccharide-protein interactions in IgG can modulate recognition by Fcgamma receptors, FASEB 1995; J 9:115-119.
Lund, J. et al., Multiple interactions of IgG with its core oligosaccharide can modulate recognition by complement and human Fc gamma receptor I and influence the synthesis of its oligosaccharide chains, J Immunol. Dec. 1, 1996; 157(11):4963-4969.
Marks J.D. et al., By-passing immunization: building high affinity human antibodies by chain shuffling. Biotechnology (N.Y). Jul. 1992; 10(7):779-783.
McCafferty J. et al., Phage antibodies: filamentous phage displaying antibody variable domains. Nature Dec. 1990;348:552-554.
McClanahan, T. et al., Identification of Overexpression of Orphan G Protein-Coupled Receptor GPR49 in Human Colon and Ovarian Primary Tumors, Canc Biol Thera. Apr. 2006; 5(4):419-426.
Mendez M.J. et al., Functional transplant of megabase human immunoglobulin loci recapitulates human antibody response in mice. Nat Gene. 1997;15:146-156.
Morgan R.A. et al., Human Gene Therapy. Annu Rev Biochem. 1993;62:191-217.
Morrison S.L., Transfectomas Provide Novel Chimeric Antibodies, Science 1985; 229:1202-1207.
Mulligan R.C. et al., Selection for animal cells that express the *Escherichia coli* gene coding for xanthine-guanine phosphoribosyltransferase. PNAS USA Apr. 1981 78(4):2072-2076.
Mulligan R.C., The basic science of gene therapy. Science 1993; 260(5110):926-932.
Mullinax, R.L. et al., Expression of a heterodimeric Fab antibody protein in one cloning step, Biotechniques. Jun. 1992;12(6):864-869.
Naramura M. et al., Mechanisms of Cellular Cytotoxicity mediated by a recombinant antibody-IL-2 Fusion Protein against Human Melanoma Cells. Immunol Lett. (1994) 39:91-99.
NCBI Genbank Accession No. NP_003658.1; Mar. 15, 2015; pp. 6.
NCBI Accession No. NM_003667.2; *Homo sapiens* leucine-rich repeat containing G protein-coupled receptor 5 (LGR5), mRNA; Mar. 3, 2013, 9 pages.
Nisonoff A., Idiotypes: Concepts and Applications. J Immunol. Oct. 1991; 147(8):2429-2438.
O'Hare K. et al., Transformation of mouse fibroblasts to methotrexate resistance by a recombinant plasmid expressing a prokaryotic dihydrofolate reductase. PNAS USA, Mar. 1981; 78(3):1527-1531.
OI V.T. et al., Chimeric Antibodies, BioTechniques Mar. 1986; 4(2):214-221.

Order S.E., Analysis, results, and future prospective of the therapeutic use of radiolabeled antibody in cancer therapy, from *Monoclonal Antibodies for Cancer Detection and Therapy* [Baldwin R.W. et al. [Eds.]], Academie Press 1985; Chapter 15; pp. 303-316.
Padlan, E.A., A possible procedure for reducing the immunogenicity of antibody variable domains while preserving their ligand-binding properties. Mol Immunol. 1991; 28(4/5):489-498.
Patten et al., Applications of DNA shuffling to pharmaceuticals and vaccines, 1997, Curr Opin Biotechnol. Dec. 1997; 8(6):724-733.
Peterson J.J. et al., Enzymatic cleavage of peptide-linked radiolabels from immunoconjugates. Bioconjug Chem. Jul.-Aug. 1998; 10 (4):553-557.
Presta L.G. et al., Engineering therapeutic antibodies for improved function, Biochem Soc Trans. Aug. 2002; 30(4):487-490.
Proudfoot N.J., Transcriptional interference and termination between duplicated alpha-globin gene constructs suggests a novel mechanism for gene regulation. Nature Aug. 1986; 322:562-565.
Reddy, M.P. et al., Elimination of Fc Receptor-Dependent Effector Functions of a Modified IgG4 Monoclonal Antibody to Human CD4, J Immunol. 2000, 164:1925-1933.
Reese M.G. et al., Improved Splice Site Detection in Genie. J Comp Biol. 1997; 4(3):311-323.
Riechmann L. et al., Reshaping human antibodies for therapy. Nature 1988; 332:323-327.
Roguska M.A. et al., Humanization of murine monoclonal antibodies through variable domain resurfacing. PNAS 1994; 91:969-973.
Rüther U. et al., Easy Identification of Cdna clones. EMBO J. 1983;2(10):1791-1983.
Santerre R.F. et al., Expression of prokaryotic genes for hygromycin B and G418 resistance as dominant-selective markers in mouse L cells. Gene 1984; 30:147-156.
Sawai H. et al., Direct Production of the Fab Fragment Derived from the Sperm Immobilizaing Antibody Using Polymerase Chain Reaction and cDNA Expression Vectors. AJRI (1995) 34:26-34.
Shields, R.L. et al., High Resolution Mapping of the Binding Site on Human IgG1 for FcgammaRI, FcgammaRII, FcgammaRIII, and FcRn and design of IgG1 Variants with Improved Binding to the FcgammaR, J Biol Chem. 2001 Mr; 276(():6591-6604.
Shields, R. L. et al., Lack of Fucose on Human IgG1 N-linked Oligosaccharide Improves Binding to Human FcgammaRIII and Antibody-dependent Cellular Toxicity, J Biol Chem. Jul. 2002; 277(3):26733-26740.
Shu L. et al., Secretion of a single-gene-encoded immunoglobulin from myeloma cells, PNAS Sep. 1993; 90(17):7995-7999.
Singh S.K. et al., Identification of human brain tumor initiating cells Nature. Nov. 2004; 432(7015):396-401.
Skerra A. et al., Assembly of a Functional Immunoglobulin Fv Fragment in *Escherichia coil*, Science 1988; 240:1038-1040.
Szybalska et al., Genetics of Human Cell Lines, IV. DNA-mediated Heritable Transformation of a Biochemical Trait. Proc. Natl. Acad. Sci. USA, 1962; 48:2026-2034.
Studnicka G.M. et al., Human-engineered monoclonal antibodies retain full specific binding activity by preserving non-CDR complementarity-modulating residues. Prot Engineer. 1994; 7(6):805-814.
Tempest P.R. et al., Reshaping a human monoclonal antibody to inhibit human respiratory syncytial virus infection in vivo. Biotechnology (N.Y) Mar. 1991;9(3):266-271.
Thorpe P.E. Antibody Carriers of Cytotoxic Agents in Cancer Therapy: A Review, in Monoclonal Antibodies '84: Biological and Clinical Applications, Pinchera et al. (Eds.), Editric Kurtis, Milano, IT 1985; pp, 475-506.
Thorpe P.E. et al., The Preparation and Cytotoxic Properties of Antibody-Toxin Conjugates, Immunol Rev. 1982; 62:119-58.
Tolstoshev P., Gene Therapy, Concepts, Current Trials and Future Directions. Annu Rev Pharmacol Toxicol. 1993; 32:573-596.
Umaña P. et al., Engineered glycoforms of an antineuroblastoma IgG1 with optimized antibody-dependent cellular cytotoxic activity, Nat Biotech. Feb. 1996; 17(2):176-180.
Van Heeke et al., Expression of Human Asparagine Synthetase in *Escherichia coli*. J Biol Chem. Apr. 1989;264(10):5503-5509.
Vié H. et al., Human Fusion Proteins between Interleukin 2 and IgM Heavy Chain are Cytotoxic for Cells Expressing the Interleukin 2 Receptor. PNAS USA. Dec. 1992; 89(23):11337-11341.

(56) References Cited

OTHER PUBLICATIONS

Wigler M. et al., Transfer of Purified Herpes Virus Thymidine Kinase Gene to Cultured Mouse Cells. Cell May 1977;11:223-232.

Wigler M. et al., Transformation of mammalian cells with an amplifiable dominant-acting gene. PNAS USA. Jun. 1980;77(6):3567-3570.

Wilson I.A. et al., The structure of an antigenic determinant in a protein. Cell. Jul. 1984; 37(3):767-778.

Wu G.Y. et al., Delivery Systems for Gene Therapy. Biotherapy. 1991; 3(1):87-95.

Xu, D. et al., In vitro characterization of five humanized OKT3 effector function variant antibodies, Cell Immunol. Feb. 25, 2000; 200(1):16-26.

Yamamoto, Y. et al., Overexpression of Orphan G-Protein-Coupled Receptor, Gpr49, in Human Hepatocellular Carcinomas with beta-Catenin Mutations, Hepat. Mar. 2003; 37(3):528-533.

Zheng X.X. et al., Administration of noncytolytic IL-10/Fc in murine models of lipopolysaccharide-induced septic shock and allogeneic islet transplantation. J Immunol. May 1995; 154(10):5590-5600.

Zimmermann K. et al., A triglycine linker improves tumor uptake and biodistributions of 67-Cu-labeled anti-neuroblastoma MAb chCE7 F(ab')2 fragments, Nucl Med Biol. Nov. 1999; 26(8):943-950.

\* cited by examiner

SEQUENCE LISTING

<160> NUMBER OF SEQ ID NOS: 49

<210> SEQ ID NO 1
<211> LENGTH: 8
<212> TYPE: PRT
<213> ORGANISM: Mouse
<220> FEATURE:
<223> OTHER INFORMATION: 18G7.1 Heavy Chain CDR1 Amino Acid

<400> SEQUENCE: 1

Gly Tyr Thr Phe Ser Gly Tyr Trp
 1               5

<210> SEQ ID NO 2
<211> LENGTH: 8
<212> TYPE: PRT
<213> ORGANISM: Mouse
<220> FEATURE:
<223> OTHER INFORMATION: 18G7.1 Heavy Chain CDR2 Amino Acid

<400> SEQUENCE: 2

Ile Leu Pro Gly Ser Asp Ser Thr
 1               5

<210> SEQ ID NO 3
<211> LENGTH: 11
<212> TYPE: PRT
<213> ORGANISM: Mouse
<220> FEATURE:
<223> OTHER INFORMATION: 18G7.1 Heavy Chain CDR3 Amino Acid

<400> SEQUENCE: 3

Ala Arg Ser Gly Tyr Tyr Gly Ser Ser Gln Tyr
 1               5                   10

<210> SEQ ID NO 4
<211> LENGTH: 10
<212> TYPE: PRT
<213> ORGANISM: Mouse
<220> FEATURE:
<223> OTHER INFORMATION: 18G7.1 Light Chain CDR1 Amino Acid

<400> SEQUENCE: 4

Glu Ser Val Asp Ser Tyr Gly Asn Ser Phe
 1               5                   10

<210> SEQ ID NO 5
<211> LENGTH: 3
<212> TYPE: PRT
<213> ORGANISM: Mouse
<220> FEATURE:
<223> OTHER INFORMATION: 18G7.1 Light Chain CDR2 Amino Acid

<400> SEQUENCE: 5

Leu Thr Ser
 1

<210> SEQ ID NO 6
<211> LENGTH: 10
<212> TYPE: PRT
<213> ORGANISM: Mouse
<220> FEATURE:
<223> OTHER INFORMATION: 18G7.1 Light Chain CDR3 Amino Acid

<400> SEQUENCE: 6

Met Gln Gln Asn Asn Glu Asp Pro Arg Thr
 1               5                   10

<210> SEQ ID NO 7
<211> LENGTH: 354
<212> TYPE: DNA
<213> ORGANISM: Artifical Sequence
<220> FEATURE:
<223> OTHER INFORMATION: 18G7H6A1 Heavy Chain DNA

<400> SEQUENCE: 7

```
gaggtgcagc tggtgcagag cggagccgag gtgaagaagc ccggcgagag cctgaggatc    60
agctgcaagg gcagcggcta cagcttcacc gcgtactgga tcgagtgggt gaggcaggct   120
cccggcaagg gcctggagtg gatcggcgag atcctgcccg gcagcgacag caccaactac   180
aacgagaagt tcaagggcca cgtgaccatc agcgccgaca agagcatcag caccgcctac   240
ctgcagtgga gcagcctgaa ggccagcgac accgccgtgt actactgcgc ccgcagcggc   300
tactacggca gcagccagta ctggggccag ggcaccctgg tgaccgtgag cagc         354
```

<210> SEQ ID NO 8
<211> LENGTH: 333
<212> TYPE: DNA
<213> ORGANISM: Artifical Sequence
<220> FEATURE:
<223> OTHER INFORMATION: 18G7H6A1 Light Chain DNA

<400> SEQUENCE: 8

```
gacatcgtgc tgacccagag ccccgccagc ctggccgtga gccccggcca gagggccacc    60
atcacctgcc gcgccagcga gagcgtggac agctacggca acagcttcat gcactggtat   120
cagcagaagc ccggccagcc ccccaagctg ctgatctacc tgaccagcaa cctggagtcc   180
ggcgtgcccg acaggttcag cggcagcggc agcggcaccg acttcaccct gaccatcaac   240
cccgtggagg ccaacgacgc cgccacctac tactgccagc agaacgccga ggaccccagg   300
accttcggcg gcggcaccaa gctggagatc aag                                333
```

<210> SEQ ID NO 9
<211> LENGTH: 466
<212> TYPE: PRT
<213> ORGANISM: Artifical Sequence
<220> FEATURE:
<223> OTHER INFORMATION: 18G7H6A1 Heavy Chain Amino Acid

<400> SEQUENCE: 9

```
Met Glu Trp Ser Trp Val Phe Leu Phe Phe Leu Ser Val Thr Thr Gly
 1               5                  10                  15

Val His Ser Glu Val Gln Leu Val Gln Ser Gly Ala Glu Val Lys Lys
            20                  25                  30

Pro Gly Glu Ser Leu Arg Ile Ser Cys Lys Gly Ser Gly Tyr Ser Phe
        35                  40                  45

Thr Ala Tyr Trp Ile Glu Trp Val Arg Gln Ala Pro Gly Lys Gly Leu
    50                  55                  60

Glu Trp Ile Gly Glu Ile Leu Pro Gly Ser Asp Ser Thr Asn Tyr Asn
65                  70                  75                  80

Glu Lys Phe Lys Gly His Val Thr Ile Ser Ala Asp Lys Ser Ile Ser
                85                  90                  95

Thr Ala Tyr Leu Gln Trp Ser Ser Leu Lys Ala Ser Asp Thr Ala Val
            100                 105                 110

Tyr Tyr Cys Ala Arg Ser Gly Tyr Tyr Gly Ser Ser Gln Tyr Trp Gly
        115                 120                 125
```

Gln Gly Thr Leu Val Thr Val Ser Ser Ala Ser Thr Lys Gly Pro Ser
            130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
450                 455                 460

Pro Gly
465

<210> SEQ ID NO 10
<211> LENGTH: 238
<212> TYPE: PRT
<213> ORGANISM: Artificial Sequence
<220> FEATURE:
<223> OTHER INFORMATION: 18G7H6A1 Light Chain Amino Acid

<400> SEQUENCE: 10

Met Ser Val Pro Thr Gln Val Leu Gly Leu Leu Leu Leu Trp Leu Thr
1               5                   10                  15

Asp Ala Arg Cys Asp Ile Val Leu Thr Gln Ser Pro Ala Ser Leu Ala
            20                  25                  30

Val Ser Pro Gly Gln Arg Ala Thr Ile Thr Cys Arg Ala Ser Glu Ser
        35                  40                  45

Val Asp Ser Tyr Gly Asn Ser Phe Met His Trp Tyr Gln Gln Lys Pro
    50                  55                  60

Gly Gln Pro Pro Lys Leu Leu Ile Tyr Leu Thr Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Asn Pro Val Glu Ala Asn Asp Ala Ala Thr Tyr Tyr Cys
            100                 105                 110

Gln Gln Asn Ala Glu Asp Pro Arg Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 11
<211> LENGTH: 1423
<212> TYPE: DNA
<213> ORGANISM: Artificial Sequence
<220> FEATURE:
<223> OTHER INFORMATION: 18G7H6A3 Heavy Chain DNA

<400> SEQUENCE: 11
aagcttgccg ccaccatgga atggtcctgg gtgttcctgt cttcctgtc cgtgaccacc      60 ggcgtgcact ccgaagtgca gctggtgcag tctggcgccg aagtgaagaa gcctggcgag     120
tccctgcgga tctcctgcaa gggctccggc tactccttca ccgcctactg gattgagtgg     180
gtgcgacagg cccctggcaa gggcctggaa tggatcggag agatcctgcc cggctccgac     240
tccaccaact acaacgagaa gttcaagggc cacgtgacca tctccgccga caagtccatc     300
tctaccgcct acctgcagtg gtcctccctg aaggcctctg acaccgccgt gtactactgc     360
gccagatccg gcctgtacgg ctcctctcag tattggggcc agggcaccct cgtgaccgtg     420
tcctctgctt ctaccaaggg cccaagcgtg ttccccctgg ccccccagca gaagagcacc     480
agcggcggca gccgcccct gggctgcctg gtgaaggact acttccccga gccgtgacc      540 gtgtcctgga cagcggagc cctgaccctc ggcgtgcaca ccttcccgc cgtgctgcag     600 agcagcggcc tgtacagcct gagcagcgtg gtgaccgtgc cagcagcag cctgggcacc     660 cagacctaca tctgtaacgt gaaccacaag cccagcaaca ccaaggtgga caagaaggtg     720
gagcccaaga gctgtgacaa gacccacacc tgccccccct gcccagcccc cgagctgctg     780
ggcggaccca gcgtgttcct gttccccccc aagccccaagg acaccctgat gatcagcaga    840

```
accccccgagg tgacctgtgt ggtggtggac gtgtcccacg aggacccaga ggtgaagttc    900
aactggtacg tggacggcgt ggaggtgcac aacgccaaga ccaagcccag agaggagcag    960
tacaacagca cctacagggt ggtgtccgtg ctgaccgtgc tgcaccagga ctggctgaac   1020
ggcaaggagt acaagtgtaa ggtgtccaac aaggccctgc cagccccaat cgaaaagacc   1080
atcagcaagg ccaagggcca gccaagagag ccccaggtgt acaccctgcc acccagcagg   1140
gacgagctga ccaagaacca ggtgtccctg acctgtctgg tgaagggctt ctacccaagc   1200
gacatcgccg tggagtggga gagcaacggc cagcccgaga caactacaa gaccaccccc    1260 ccagtgctgg acagcgacgg cagcttcttc ctgtacagca agctgaccgt ggacaagagc   1320
agatggcagc agggcaacgt gttcagctgc tccgtgatgc acgaggccct gcacaaccac   1380
tacacccaga gagcctgag cctgtcccca ggctgatgaa ttc                      1423
```

<210> SEQ ID NO 12
<211> LENGTH: 739
<212> TYPE: DNA
<213> ORGANISM: Artificial Sequence
<220> FEATURE:
<223> OTHER INFORMATION: 18G7H6A3 Light Chain DNA

<400> SEQUENCE: 12

```
aagcttgccg ccaccatgtc cgtgcctacc caggtgctgg gactgctgct gctgtggctg     60
accgacgcca gatgcgacat cgtgctgacc cagagccctg cctctctggc tgtgtctcct    120
ggccagaggg ccaccatcac ctgtagagcc tccgagtccg tggactccta cggcaactcc    180
ttcatgcact ggtatcagca gaagcccggc cagcccccca gctgctgat ctacctgacc     240 tccaacctgg aatccggcgt gcccgacaga ttctccggct ctggctctgg caccgacttc    300
accctgacca tcaaccccgt ggaagccaac gacgccgcca cctactactg ccagcagaac    360
gccgaggacc ccagaacctt tggcggaggc accaagctgg aaatcaagcg tacggtggcc    420
gctcccagcg tgttcatctt cccccccaagc gacgagcagc tgaagagcgg caccgccagc    480
gtggtgtgtc tgctgaacaa cttctacccc agggaggcca aggtgcagtg gaaggtggac    540
aacgccctgc agagcggcaa cagccaggag agcgtcaccg agcaggacag caaggactcc    600
acctacagcc tgagcagcac cctgaccctg agcaaggccg actacgagaa gcacaaggtg    660
tacgcctgtg aggtgaccca ccagggcctg tccagccccg tgaccaagag cttcaacagg    720
ggcgagtgct gatgaattc                                                 739
```

<210> SEQ ID NO 13
<211> LENGTH: 466
<212> TYPE: PRT
<213> ORGANISM: Artificial Sequence
<220> FEATURE:
<223> OTHER INFORMATION: 18G7H6A3 Heavy Chain Amino Acid

<400> SEQUENCE: 13

```
Met Glu Trp Ser Trp Val Phe Leu Phe Phe Leu Ser Val Thr Thr Gly
  1               5                  10                  15

Val His Ser Glu Val Gln Leu Val Gln Ser Gly Ala Glu Val Lys Lys
             20                  25                  30

Pro Gly Glu Ser Leu Arg Ile Ser Cys Lys Gly Ser Gly Tyr Ser Phe
         35                  40                  45

Thr Ala Tyr Trp Ile Glu Trp Val Arg Gln Ala Pro Gly Lys Gly Leu
     50                  55                  60
```

```
Glu Trp Ile Gly Glu Ile Leu Pro Gly Ser Asp Ser Thr Asn Tyr Asn
 65                  70                  75                  80

Glu Lys Phe Lys Gly His Val Thr Ile Ser Ala Asp Lys Ser Ile Ser
                 85                  90                  95

Thr Ala Tyr Leu Gln Trp Ser Ser Leu Lys Ala Ser Asp Thr Ala Val
            100                 105                 110

Tyr Tyr Cys Ala Arg Ser Gly Leu Tyr Gly Ser Ser Gln Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly
465
```

<210> SEQ ID NO 14
<211> LENGTH: 238
<212> TYPE: PRT
<213> ORGANISM: Artificial Sequence
<220> FEATURE:
<223> OTHER INFORMATION: 18G7H6A3 Light Chain Amino Acid

<400> SEQUENCE: 14

```
Met Ser Val Pro Thr Gln Val Leu Gly Leu Leu Leu Trp Leu Thr
1               5                   10                  15

Asp Ala Arg Cys Asp Ile Val Leu Thr Gln Ser Pro Ala Ser Leu Ala
            20                  25                  30

Val Ser Pro Gly Gln Arg Ala Thr Ile Thr Cys Arg Ala Ser Glu Ser
        35                  40                  45

Val Asp Ser Tyr Gly Asn Ser Phe Met His Trp Tyr Gln Gln Lys Pro
    50                  55                  60

Gly Gln Pro Pro Lys Leu Leu Ile Tyr Leu Thr Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Asn Pro Val Glu Ala Asn Asp Ala Ala Thr Tyr Tyr Cys
            100                 105                 110

Gln Gln Asn Ala Glu Asp Pro Arg Thr Phe Gly Gly Gly Thr Lys Leu
        115                 120                 125

Glu Ile Lys Arg Thr Val Ala Ala Pro Ser Val Phe Ile Phe Pro Pro
    130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
            180                 185                 190

Lys Asp Ser Thr Tyr Ser Leu Ser Ser Thr Leu Thr Leu Ser Lys Ala
        195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235
```

<210> SEQ ID NO 15
<211> LENGTH: 354
<212> TYPE: DNA
<213> ORGANISM: Artificial Sequence
<220> FEATURE:
<223> OTHER INFORMATION: 18G7Ch Heavy Chain DNA

<400> SEQUENCE: 15

| | | |
|---|---|---|
| caggttcagc tgcagcagtc tggagctgag ctggtgaagc ctggggcctc agtgaagata | 60 |
| tcctgcaagg ctactggcta cacattcagt ggctactgga tagagtgggt aaagcagagg | 120 |
| cctggacatg gccttgagtg gattggagag attttgcctg gaagtgatag tactaactac | 180 |
| aatgagaagt tcaagggcaa ggccacattc actgcagata catcctccaa cacagtctac | 240 |
| atgcaattca gcagcctgac atctgaggac tctgccgtct attactgtgc aagatcgggt | 300 |
| tactacggta gtagtcagta ctggggccaa ggcaccactc tcacagtctc ctca | 354 |

<210> SEQ ID NO 16
<211> LENGTH: 334

```
<212> TYPE: DNA
<213> ORGANISM: Artificial Sequence
<220> FEATURE:
<223> OTHER INFORMATION: 18G7Ch Light Chain DNA

<400> SEQUENCE: 16
aacattgtgc tgacccaatc tcctgcttct ttggctgtgt ctctagggca gagggccacc      60
atatcctgca gagccagtga aagtgttgat agttatggca atagttttat gcactggtac     120
cagcagaaac aggacagcc acccaaactc ctcatctatc ttacatccaa cctagaatct      180
ggggtccctg ccaggttcag tggcagtggg tctaggacag acttcaccct caccattgat     240
cctgtggagg ctgatgatgc tgcaacctat tactgtcagc aaaataatga ggatcctcgg     300
acgttcggtg gaggcaccaa gctggaaatc aaac                                 334

<210> SEQ ID NO 17
<211> LENGTH: 466
<212> TYPE: PRT
<213> ORGANISM: Artificial Sequence
<220> FEATURE:
<223> OTHER INFORMATION: 18G7Ch Heavy Chain Amino Acid

<400> SEQUENCE: 17

Met Glu Trp Ser Trp Val Phe Leu Phe Phe Leu Ser Val Thr Thr Gly
  1               5                  10                  15

Val His Ser Gln Val Gln Leu Gln Gln Ser Gly Ala Glu Leu Val Lys
             20                  25                  30

Pro Gly Ala Ser Val Lys Ile Ser Cys Lys Ala Thr Gly Tyr Thr Phe
         35                  40                  45

Ser Gly Tyr Trp Ile Glu Trp Val Lys Gln Arg Pro Gly His Gly Leu
     50                  55                  60

Glu Trp Ile Gly Glu Ile Leu Pro Gly Ser Asp Ser Thr Asn Tyr Asn
 65                  70                  75                  80

Glu Lys Phe Lys Gly Lys Ala Thr Phe Thr Ala Asp Thr Ser Ser Asn
                 85                  90                  95

Thr Val Tyr Met Gln Phe Ser Ser Leu Thr Ser Glu Asp Ser Ala Val
            100                 105                 110

Tyr Tyr Cys Ala Arg Ser Gly Tyr Tyr Gly Ser Ser Gln Tyr Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270
```

```
Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
450                 455                 460

Pro Gly
465

<210> SEQ ID NO 18
<211> LENGTH: 238
<212> TYPE: PRT
<213> ORGANISM: Artificial Sequence
<220> FEATURE:
<223> OTHER INFORMATION: 18G7ch Light Chain Amino Acid

<400> SEQUENCE: 18

Met Ser Val Pro Thr Gln Val Leu Gly Leu Leu Leu Leu Trp Leu Thr
1               5                   10                  15

Asp Ala Arg Cys Asn Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
            35                  40                  45

Val Asp Ser Tyr Gly Asn Ser Phe Met His Trp Tyr Gln Gln Lys Pro
50                  55                  60

Gly Gln Pro Pro Lys Leu Leu Ile Tyr Leu Thr Ser Asn Leu Glu Ser
65                  70                  75                  80

Gly Val Pro Ala Arg Phe Ser Gly Ser Gly Ser Arg Thr Asp Phe Thr
            85                  90                  95

Leu Thr Ile Asp Pro Val Glu Ala Asp Asp Ala Ala Thr Tyr Tyr Cys
            100                 105                 110

Gln Gln Asn Asn Glu Asp Pro Arg Thr Phe Gly Gly Gly Thr Lys Leu
            115                 120                 125

Glu Ile Lys Arg Thr Val Ala Ala Pro Ser Val Phe Ile Phe Pro Pro
130                 135                 140

Ser Asp Glu Gln Leu Lys Ser Gly Thr Ala Ser Val Val Cys Leu Leu
145                 150                 155                 160
```

Asn Asn Phe Tyr Pro Arg Glu Ala Lys Val Gln Trp Lys Val Asp Asn
            165                 170                 175

Ala Leu Gln Ser Gly Asn Ser Gln Glu Ser Val Thr Glu Gln Asp Ser
        180                 185                 190

Lys Asp Ser Thr Tyr Ser Leu Ser Ser Thr Leu Thr Leu Ser Lys Ala
    195                 200                 205

Asp Tyr Glu Lys His Lys Val Tyr Ala Cys Glu Val Thr His Gln Gly
    210                 215                 220

Leu Ser Ser Pro Val Thr Lys Ser Phe Asn Arg Gly Glu Cys
225                 230                 235

<210> SEQ ID NO 19
<211> LENGTH: 137
<212> TYPE: PRT
<213> ORGANISM: Artificial Sequence
<220> FEATURE:
<223> OTHER INFORMATION: 18G7H6A3 Heavy Chain Variable Domain Amino Acid

<400> SEQUENCE: 19

Met Glu Trp Ser Trp Val Phe Leu Phe Phe Leu Ser Val Thr Thr Gly
1               5                   10                  15

Val His Ser Glu Val Gln Leu Val Gln Ser Gly Ala Glu Val Lys Lys
            20                  25                  30

Pro Gly Glu Ser Leu Arg Ile Ser Cys Lys Gly Ser Gly Tyr Ser Phe
        35                  40                  45

Thr Ala Tyr Trp Ile Glu Trp Val Arg Gln Ala Pro Gly Lys Gly Leu
    50                  55                  60

Glu Trp Ile Gly Glu Ile Leu Pro Gly Ser Asp Ser Thr Asn Tyr Asn
65                  70                  75                  80

Glu Lys Phe Lys Gly His Val Thr Ile Ser Ala Asp Lys Ser Ile Ser
                85                  90                  95

Thr Ala Tyr Leu Gln Trp Ser Ser Leu Lys Ala Ser Asp Thr Ala Val
            100                 105                 110

Tyr Tyr Cys Ala Arg Ser Gly Tyr Tyr Gly Ser Ser Gln Tyr Trp Gly
        115                 120                 125

Gln Gly Thr Leu Val Thr Val Ser Ser
    130                 135

<210> SEQ ID NO 20
<211> LENGTH: 411
<212> TYPE: DNA
<213> ORGANISM: Artificial Sequence
<220> FEATURE:
<223> OTHER INFORMATION: 18G7H6A3 Heavy Chain Variable Domain DNA

<400> SEQUENCE: 20
atggaatggt cctgggtgtt cctgttcttc ctgtccgtga ccaccggcgt gcactccgaa     60
gtgcagctgg tgcagtctgg cgccgaagtg aagaagcctg gcgagtccct gcggatctcc    120
tgcaagggct ccggctactc cttcaccgcc tactggattg agtgggtgcg acaggcccct    180
ggcaagggcc tggaatggat cggagagatc ctgcccggct ccgactccac caactacaac    240
gagaagttca aggccacgt gaccatctcc gccgacaagt ccatctctac cgcctacctg    300
cagtggtcct ccctgaaggc ctctgacacc gccgtgtact actgcgccag atccggcctg    360
tacggctcct ctcagtattg gggccagggc accctcgtga ccgtgtcctc t             411

<210> SEQ ID NO 21

```
<211> LENGTH: 131
<212> TYPE: PRT
<213> ORGANISM: Artificial Sequence
<220> FEATURE:
<223> OTHER INFORMATION: 18G7H6A3 Light Chain Variable Domain

<400> SEQUENCE: 21

Met Ser Val Pro Thr Gln Val Leu Gly Leu Leu Leu Leu Trp Leu Thr
 1               5                  10                  15

Asp Ala Arg Cys Asp Ile Val Leu Thr Gln Ser Pro Ala Ser Leu Ala
             20                  25                  30

Val Ser Pro Gly Gln Arg Ala Thr Ile Thr Cys Arg Ala Ser Glu Ser
         35                  40                  45

Val Asp Ser Tyr Gly Asn Ser Phe Met His Trp Tyr Gln Gln Lys Pro
     50                  55                  60

Gly Gln Pro Pro Lys Leu Leu Ile Tyr Leu Thr Ser Asn Leu Glu Ser
 65                  70                  75                  80

Gly Val Pro Asp Arg Phe Ser Gly Ser Gly Ser Gly Thr Asp Phe Thr
                 85                  90                  95

Leu Thr Ile Asn Pro Val Glu Ala Asn Asp Ala Ala Thr Tyr Tyr Cys
            100                 105                 110

Gln Gln Asn Ala Glu Asp Pro Arg Thr Phe Gly Gly Gly Thr Lys Leu
        115                 120                 125

Glu Ile Lys
    130

<210> SEQ ID NO 22
<211> LENGTH: 393
<212> TYPE: DNA
<213> ORGANISM: Artificial Sequence
<220> FEATURE:
<223> OTHER INFORMATION: 18G7H6A3 Light Chain Variable Domain DNA

<400> SEQUENCE: 22
atgtccgtgc ctacccaggt gctgggactg ctgctgctgt ggctgaccga cgccagatgc     60
gacatcgtgc tgacccagag ccctgcctct ctggctgtgt ctcctggcca gagggccacc    120
atcacctgta gagcctccga gtccgtggac tcctacggca actccttcat gcactggtat    180
cagcagaagc ccggccagcc ccccaagctg ctgatctacc tgacctccaa cctggaatcc    240
ggcgtgcccg acagattctc cggctctggc tctggcaccg acttcaccct gaccatcaac    300
cccgtggaag ccaacgacgc cgccacctac tactgccagc agaacgccga ggaccccaga    360
acctttggcg gaggcaccaa gctggaaatc aag                                 393

<210> SEQ ID NO 23
<211> LENGTH: 8
<212> TYPE: PRT
<213> ORGANISM: Artificial Sequence
<220> FEATURE:
<223> OTHER INFORMATION: 18G7H6A3 Heavy Chain CDR1 Amino Acid

<400> SEQUENCE: 23

Gly Tyr Ser Phe Thr Ala Tyr Trp
 1               5

<210> SEQ ID NO 24
<211> LENGTH: 24
<212> TYPE: DNA
<213> ORGANISM: Artificial Sequence
<220> FEATURE:
<223> OTHER INFORMATION: 18G7H6A3 Heavy Chain CDR1 DNA
```

<400> SEQUENCE: 24
ggctactcct tcaccgccta ctgg                                              24

<210> SEQ ID NO 25
<211> LENGTH: 8
<212> TYPE: PRT
<213> ORGANISM: Artificial Sequence
<220> FEATURE:
<223> OTHER INFORMATION: 18G7H6A3 Heavy Chain CDR2 Amino Acid

<400> SEQUENCE: 25

Ile Leu Pro Gly Ser Asp Ser Thr
 1               5

<210> SEQ ID NO 26
<211> LENGTH: 24
<212> TYPE: DNA
<213> ORGANISM: Artificial Sequence
<220> FEATURE:
<223> OTHER INFORMATION: 18G7H6A3 Heavy Chain CDR2 DNA

<400> SEQUENCE: 26
atcctgcccg gctccgactc cacc                                              24

<210> SEQ ID NO 27
<211> LENGTH: 11
<212> TYPE: PRT
<213> ORGANISM: Artificial Sequence
<220> FEATURE:
<223> OTHER INFORMATION: 18G7H6A3 Heavy Chain CDR3 Amino Acid

<400> SEQUENCE: 27

Ala Arg Ser Gly Tyr Tyr Gly Ser Ser Gln Tyr
 1               5                  10

<210> SEQ ID NO 28
<211> LENGTH: 33
<212> TYPE: DNA
<213> ORGANISM: Artificial Sequence
<220> FEATURE:
<223> OTHER INFORMATION: 18G7H6A3 Heavy Chain CDR3 DNA

<400> SEQUENCE: 28
gccagatccg gcctgtacgg ctcctctcag tat                                    33

<210> SEQ ID NO 29
<211> LENGTH: 10
<212> TYPE: PRT
<213> ORGANISM: Artificial Sequence
<220> FEATURE:
<223> OTHER INFORMATION: 18G7H6A3 Light Chain CDR1 Amino Acid

<400> SEQUENCE: 29

Glu Ser Val Asp Ser Tyr Gly Asn Ser Phe
 1               5                  10

<210> SEQ ID NO 30
<211> LENGTH: 30
<212> TYPE: DNA
<213> ORGANISM: Artificial Sequence
<220> FEATURE:
<223> OTHER INFORMATION: 18G7H6A3 Light Chain CDR1 DNA

<400> SEQUENCE: 30
gagtccgtgg actcctacgg caactccttc                                        30

<210> SEQ ID NO 31
<211> LENGTH: 3
<212> TYPE: PRT
<213> ORGANISM: Artificial Sequence
<220> FEATURE:
<223> OTHER INFORMATION: 18G7H6A3 Light Chain CDR2 Amino Acid

<400> SEQUENCE: 31

Leu Thr Ser
 1

<210> SEQ ID NO 32
<211> LENGTH: 9
<212> TYPE: DNA
<213> ORGANISM: Artificial Sequence
<220> FEATURE:
<223> OTHER INFORMATION: 18G7H6A3 Light Chain CDR2 DNA

<400> SEQUENCE: 32 ctgacctcc                                                                  9

<210> SEQ ID NO 33
<211> LENGTH: 9
<212> TYPE: PRT
<213> ORGANISM: Artificial Sequence
<220> FEATURE:
<223> OTHER INFORMATION: 18G7H6A3 Light Chain CDR3 Amino Acid

<400> SEQUENCE: 33

Gln Gln Asn Ala Glu Asp Pro Arg Thr
 1               5

<210> SEQ ID NO 34
<211> LENGTH: 27
<212> TYPE: DNA
<213> ORGANISM: Artificial Sequence
<220> FEATURE:
<223> OTHER INFORMATION: 18G7H6A3 Light Chain CDR3 DNA

<400> SEQUENCE: 34
cagcagaacg ccgaggaccc cagaacc                                             27

<210> SEQ ID NO 35
<211> LENGTH: 8
<212> TYPE: PRT
<213> ORGANISM: Artificial Sequence
<220> FEATURE:
<223> OTHER INFORMATION: 18G7H6A1 Heavy Chain CDR1 Amino Acid

<400> SEQUENCE: 35

Gly Tyr Ser Phe Thr Ala Tyr Trp
 1               5

<210> SEQ ID NO 36
<211> LENGTH: 24
<212> TYPE: DNA
<213> ORGANISM: Artificial Sequence
<220> FEATURE:
<223> OTHER INFORMATION: 18G7H6A1 Heavy Chain CDR1 DNA

<400> SEQUENCE: 36
ggctactcct tcaccgccta ctgg                                                24

<210> SEQ ID NO 37
<211> LENGTH: 8

<212> TYPE: PRT
<213> ORGANISM: Artificial Sequence
<220> FEATURE:
<223> OTHER INFORMATION: 18G7H6A1 Heavy Chain CDR2 Amino Acid

<400> SEQUENCE: 37

Ile Leu Pro Gly Ser Asp Ser Thr
 1               5

<210> SEQ ID NO 38
<211> LENGTH: 24
<212> TYPE: DNA
<213> ORGANISM: Artificial Sequence
<220> FEATURE:
<223> OTHER INFORMATION: 18G7H6A1 Heavy Chain CDR2 DNA

<400> SEQUENCE: 38
atcctgcccg gcagcgacag cacc                                          24

<210> SEQ ID NO 39
<211> LENGTH: 11
<212> TYPE: PRT
<213> ORGANISM: Artificial Sequence
<220> FEATURE:
<223> OTHER INFORMATION: 18G7H6A1 Heavy Chain CDR3 Amino Acid

<400> SEQUENCE: 39

Ala Arg Ser Gly Tyr Tyr Gly Ser Ser Gln Tyr
 1               5                   10

<210> SEQ ID NO 40
<211> LENGTH: 33
<212> TYPE: DNA
<213> ORGANISM: Artificial Sequence
<220> FEATURE:
<223> OTHER INFORMATION: 18G7H6A1 Heavy Chain CDR3 DNA

<400> SEQUENCE: 40
gcccgcagcg gctactacgg cagcagccag tac                                33

<210> SEQ ID NO 41
<211> LENGTH: 10
<212> TYPE: PRT
<213> ORGANISM: Artificial Sequence
<220> FEATURE:
<223> OTHER INFORMATION: 18G7H6A1 Light Chain CDR1 Amino Acid

<400> SEQUENCE: 41

Glu Ser Val Asp Ser Tyr Gly Asn Ser Phe
 1               5                   10

<210> SEQ ID NO 42
<211> LENGTH: 30
<212> TYPE: DNA
<213> ORGANISM: Artificial Sequence
<220> FEATURE:
<223> OTHER INFORMATION: 18G7H6A1 Light Chain CDR1 DNA

<400> SEQUENCE: 42
gagagcgtgg acagctacgg caacagcttc                                    30

<210> SEQ ID NO 43
<211> LENGTH: 3
<212> TYPE: PRT
<213> ORGANISM: Artificial Sequence
<220> FEATURE:
<223> OTHER INFORMATION: 18G7H6A1 Light Chain CDR2 Amino Acid

<400> SEQUENCE: 43

Leu Thr Ser
 1

<210> SEQ ID NO 44
<211> LENGTH: 9
<212> TYPE: DNA
<213> ORGANISM: Artificial Sequence
<220> FEATURE:
<223> OTHER INFORMATION: 18G7H6A1 Light Chain CDR2 DNA

<400> SEQUENCE: 44 ctgaccagc                                                                9

<210> SEQ ID NO 45
<211> LENGTH: 9
<212> TYPE: PRT
<213> ORGANISM: Artificial Sequence
<220> FEATURE:
<223> OTHER INFORMATION: 18G7H6A1 Light Chain CDR3 Amino Acid

<400> SEQUENCE: 45

Gln Gln Asn Ala Glu Asp Pro Arg Thr
 1               5

<210> SEQ ID NO 46
<211> LENGTH: 27
<212> TYPE: DNA
<213> ORGANISM: Artificial Sequence
<220> FEATURE:
<223> OTHER INFORMATION: 18G7H6A1 Light Chain CDR3 DNA

<400> SEQUENCE: 46
cagcagaacg ccgaggaccc caggacc                                            27

<210> SEQ ID NO 47
<211> LENGTH: 561
<212> TYPE: PRT
<213> ORGANISM: Homo Sapiens

<400> SEQUENCE: 47

Met Asp Thr Ser Arg Leu Gly Val Leu Leu Ser Leu Pro Val Leu Leu
 1               5                  10                  15

Gln Leu Ala Thr Gly Gly Ser Ser Pro Arg Ser Gly Val Leu Leu Arg
                20                  25                  30

Gly Cys Pro Thr His Cys His Cys Glu Pro Asp Gly Arg Met Leu Leu
            35                  40                  45

Arg Val Asp Cys Ser Asp Leu Gly Leu Ser Glu Leu Pro Ser Asn Leu
        50                  55                  60

Ser Val Phe Thr Ser Tyr Leu Asp Leu Ser Met Asn Asn Ile Ser Gln
 65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
                100                 105                 110

Leu Tyr Ser Leu Lys Val Leu Met Leu Gln Asn Asn Gln Leu Arg His
            115                 120                 125

Val Pro Thr Glu Ala Leu Gln Asn Leu Arg Ser Leu Gln Ser Leu Arg
        130                 135                 140

Leu Asp Ala Asn His Ile Ser Tyr Val Pro Pro Ser Cys Phe Ser Gly

```
            145                 150                 155                 160
Leu His Ser Leu Arg His Leu Trp Leu Asp Asp Asn Ala Leu Thr Glu
                    165                 170                 175

Ile Pro Val Gln Ala Phe Arg Ser Leu Ser Ala Leu Gln Ala Met Thr
                    180                 185                 190

Leu Ala Leu Asn Lys Ile His Ile Pro Asp Tyr Ala Phe Gly Asn
                    195                 200                 205

Leu Ser Ser Leu Val Val Leu His Leu His Asn Asn Arg Ile His Ser
                    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                    245                 250                 255

Ser Asn Leu Lys Glu Leu Gly Phe His Ser Asn Asn Ile Arg Ser Ile
                    260                 265                 270

Pro Glu Lys Ala Phe Val Gly Asn Pro Ser Leu Ile Thr Ile His Phe
                    275                 280                 285

Tyr Asp Asn Pro Ile Gln Phe Val Gly Arg Ser Ala Phe Gln His Leu
                    290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                    325                 330                 335

Gly Ala Gln Ile Ser Ser Leu Pro Gln Thr Val Cys Asn Gln Leu Pro
                    340                 345                 350

Asn Leu Gln Val Leu Asp Leu Ser Tyr Asn Leu Leu Glu Asp Leu Pro
                    355                 360                 365

Ser Phe Ser Val Cys Gln Lys Leu Gln Lys Ile Asp Leu Arg His Asn
                    370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile His Pro Asn
                    405                 410                 415

Ala Phe Ser Thr Leu Pro Ser Leu Ile Lys Leu Asp Leu Ser Ser Asn
                    420                 425                 430

Leu Leu Ser Ser Phe Pro Ile Thr Gly Leu His Gly Leu Thr His Leu
                    435                 440                 445

Lys Leu Thr Gly Asn His Ala Leu Gln Ser Leu Ile Ser Ser Glu Asn
                    450                 455                 460

Phe Pro Glu Leu Lys Val Ile Glu Met Pro Tyr Ala Tyr Gln Cys Cys
465                 470                 475                 480

Ala Phe Gly Val Cys Glu Asn Ala Tyr Lys Ile Ser Asn Gln Trp Asn
                    485                 490                 495

Lys Gly Asp Asn Ser Ser Met Asp Asp Leu His Lys Lys Asp Ala Gly
                    500                 505                 510

Met Phe Gln Ala Gln Asp Glu Arg Asp Leu Glu Asp Phe Leu Leu Asp
                    515                 520                 525

Phe Glu Glu Asp Leu Lys Ala Leu His Ser Val Gln Cys Ser Pro Ser
                    530                 535                 540

Pro Gly Pro Phe Lys Pro Cys Glu His Leu Leu Asp Gly Trp Leu Ile
545                 550                 555                 560

Arg
```

```
<210> SEQ ID NO 48
<211> LENGTH: 137
<212> TYPE: PRT
<213> ORGANISM: Artificial Sequence
<220> FEATURE:
<223> OTHER INFORMATION: 18G7H6A1 Heavy Chain Variable Amino acid

<400> SEQUENCE: 48

Met Glu Trp Ser Trp Val Phe Leu Phe Phe Leu Ser Val Thr Thr Gly
 1               5                  10                  15

Val His Ser Glu Val Gln Leu Val Gln Ser Gly Ala Glu Val Lys Lys
            20                  25                  30

Pro Gly Glu Ser Leu Arg Ile Ser Cys Lys Gly Ser Gly Tyr Ser Phe
        35                  40                  45

Thr Ala Tyr Trp Ile Glu Trp Val Arg Gln Ala Pro Gly Lys Gly Leu
    50                  55                  60

Glu Trp Ile Gly Glu Ile Leu Pro Gly Ser Asp Ser Thr Asn Tyr Asn
65                  70                  75                  80

Glu Lys Phe Lys Gly His Val Thr Ile Ser Ala Asp Lys Ser Ile Ser
                85                  90                  95

Thr Ala Tyr Leu Gln Trp Ser Ser Leu Lys Ala Ser Asp Thr Ala Val
            100                 105                 110

Tyr Tyr Cys Ala Arg Ser Gly Tyr Tyr Gly Ser Ser Gln Tyr Trp Gly
        115                 120                 125

Gln Gly Thr Leu Val Thr Val Ser Ser
    130                 135

<210> SEQ ID NO 49
<211> LENGTH: 131
<212> TYPE: PRT
<213> ORGANISM: Artificial Sequence
<220> FEATURE:
<223> OTHER INFORMATION: 18G7H6A1 Light Chain Variable Amino acid

<400> SEQUENCE: 49

Met Ser Val Pro Thr Gln Val Leu Gly Leu Leu Leu Leu Trp Leu Thr
 1               5                  10                  15

Asp Ala Arg Cys Asp Ile Val Leu Thr Gln Ser Pro Ala Ser Leu Ala
            20                  25                  30

Val Ser Pro Gly Gln Arg Ala Thr Ile Thr Cys Arg Ala Ser Glu Ser
        35                  40                  45

Val Asp Ser Tyr Gly Asn Ser Phe Met His Trp Tyr Gln Gln Lys Pro
    50                  55                  60

Gly Gln Pro Pro Lys Leu Leu Ile Tyr Leu Thr Ser Asn Leu Glu Ser
65                  70                  75                  80

Gly Val Pro Asp Arg Phe Ser Gly Ser Gly Ser Gly Thr Asp Phe Thr
                85                  90                  95

Leu Thr Ile Asn Pro Val Glu Ala Asn Asp Ala Ala Thr Tyr Tyr Cys
            100                 105                 110

Gln Gln Asn Ala Glu Asp Pro Arg Thr Phe Gly Gly Gly Thr Lys Leu
        115                 120                 125

Glu Ile Lys
    130
```

HUMANIZED ANTIBODIES THAT BIND LGR5

RELATED APPLICATIONS

This application claims the benefit of U.S. Provisional App. No. 62/081,497 filed Nov. 18, 2014, and U.S. Provisional App. No. 61/975,589 filed Apr. 4, 2014, the contents of which are incorporated herein by reference in their entireties.

FIELD OF THE INVENTION

The present invention relates generally to the field of cancer biology. More particularly, embodiments are drawn to humanized antibodies against LGR5 and uses of such antibodies. Several embodiments relate to monoclonal, humanized, or fully human antibodies against LGR5, hybridomas or other cell lines expressing such antibodies, nucleic acids and vectors comprising nucleic acids encoding for such antibodies, and methods of blocking cancer stem cell growth with such antibodies.

REFERENCE TO SEQUENCE LISTING

The present application is being filed along with a Sequence Listing in electronic format. The Sequence Listing is provided as a file entitled BIONO10A_SEQLISTING.TXT, created Apr. 2, 2015 which is approximately 40 Kb in size. The information in the electronic format of the Sequence Listing is incorporated herein by reference in its entirety.

BACKGROUND OF THE INVENTION

Leucine-rich repeat containing G-protein-coupled receptor 5 (LGR5), also known as GPR49/HG38/FEX, belongs to the leucine-rich repeat containing G-protein-coupled receptor (LGR)/G-Protein-coupled Receptor (GPR) protein family of receptor proteins that are structurally similar to glycoprotein hormone receptors. LGRs are divided into three subgroups: (1) glycoprotein hormone receptors including thyroid-stimulating hormone (TSH) receptor, follicle-stimulating hormone (FSH) receptor, and luteinizing hormone (LH) receptor; (2) relaxin receptors LGR7 and LGR8; and (3) LRG4, LGR5, and LGR6. LGR5 is expressed in several tissues including the intestine, skeletal muscle, placenta, brain, and spinal cord.

SUMMARY OF THE INVENTION

Some embodiments of the compositions, methods and kits provided herein include a humanized or human monoclonal antibody that binds LGR5. In some embodiments, the antibody comprises a heavy chain CDR1 comprising SEQ ID NO:23 or conservative variations thereof. In some embodiments, the antibody comprises a heavy chain CDR2 comprising SEQ ID NO:2 or conservative variations thereof. In some embodiments, the antibody comprises a heavy chain CDR3 comprising SEQ ID NO:3 or conservative variations thereof. In some embodiments, the antibody comprises a light chain CDR1 comprising SEQ ID NO:4 or conservative variations thereof. In some embodiments, the antibody comprises a light chain CDR2 having amino acids LTS or conservative variations thereof. In some embodiments, the antibody comprises a light chain CDR3 comprising SEQ ID NO:33 or conservative variations thereof. In some embodiments, the antibody comprises a heavy chain variable domain comprising SEQ ID NOs:19 or 48. In some embodiments, the antibody comprises a light chain variable domain comprising SEQ ID NOs: 21 or 49. In some embodiments, the antibody binds an epitope within amino acids T175, E176, Q180, R183, S186, A187, Q189, D247, E248, T251, R254, S257, N258, K260 of LGR5 (SEQ ID NO:47). In some embodiments, the antibody binds an epitope within leucine rich repeats 6-9 of LGR5 (SEQ ID NO:47). In some embodiments, the antibody binds an epitope on the convex surface of LGR5. In some embodiments, the antibody does not bind a RSPO-LGR5 binding site. In some embodiments, the antibody does not disrupt LGR5-RSPO binding. In some embodiments, the antibody does not disrupt LGR5-RSPO signaling. In some embodiments, the RSPO is selected from the group consisting of RSPO1, RSPO2, RSPO3, and RSPO4. In some embodiments, the antibody does disrupt formation of a complex such as LGR5-RSPO-RNF43, LGR5-RSPO-ZNRF3, LGR5-RSPO-LRP6, LGR5-NORRIN-RNF43, LGR5-NORRIN-ZNRF3, LGR5-NORRIN-LRP6. In some embodiments, the antibody disrupts LGR5 signaling through Wnt/β-catenin pathway. In some embodiments, the antibody induces expression of differentiation markers in a tumor. In some embodiments, the antibody is capable of inducing cells in a tumor to differentiate. In some embodiments, the antibody which inhibits tumor growth. In some embodiments, the antibody reduces the frequency of cancer stem cells in a tumor.

Some embodiments of the compositions, methods and kits provided herein include an isolated polynucleotide molecule comprising a polynucleotide that encodes any one of the foregoing antibodies. Some embodiments of the compositions, methods and kits provided herein include a vector comprising any one of the foregoing polynucleotides. Some embodiments of the compositions, methods and kits provided herein include a host cell comprising any one of the foregoing vectors. Some embodiments of the compositions, methods and kits provided herein include a method of producing an antibody comprising culturing any one of the foregoing host cells so that the antibody is produced.

Some embodiments of the compositions, methods and kits provided herein include a pharmaceutical composition comprising any one of the foregoing antibodies and a pharmaceutically acceptable carrier.

Some embodiments of the compositions, methods and kits provided herein include a method of treating a subject having a cancer comprising administering any one of the foregoing antibodies to the subject. Some embodiments also include administering a chemotherapeutic agent in combination with the antibody. In some embodiments, the chemotherapeutic agent is selected from the group consisting of folinic acid, fluorouracil, irinotecan, gemcitabine and Abraxane. In some embodiments, the folinic acid, fluorouracil, and irinotecan are administered in combination with the antibody to the subject.

In some embodiments, the treatment increases the likelihood of survival of the subject for a period of at least 3 months after the treatment compared to the likelihood of survival of a subject not treated with the antibody. In some embodiments, the likelihood of survival of the subject is increased for a period of at least 6 months. In some embodiments, the likelihood of survival of the subject is increased for a period of at least 12 months.

In some embodiments, the treatment reduces the risk of recurrence of the cancer in the subject compared to the risk of recurrence of the cancer in a subject not treated with the antibody.

In some embodiments, the treatment reduces the level of tumor cells in the peripheral blood of the subject compared to the level of tumor cells in the peripheral blood of a subject not treated with the antibody.

In some embodiments, the cancer is selected from the group consisting of colon cancer, colorectal cancer, pancreatic cancer, breast cancer, and lung cancer. In some embodiments, the cancer is selected from the group consisting of colon cancer comprising an APC mutation, colon cancer comprising an KRAS mutation, metastatic colorectal cancer, metastatic pancreatic cancer, triple-negative breast cancer, and small cell lung cancer.

In some embodiments, the subject is mammalian. In some embodiments, the subject is human.

Some embodiments of the compositions, methods and kits provided herein include a method for reducing the risk of developing a cancer, preventing the recurrence of a cancer, or preventing a cancer in a subject predisposed to the cancer comprising administering any one of the foregoing antibodies to the subject.

Some embodiments of the compositions, methods and kits provided herein include a method of increasing the likelihood of survival of a subject having a cancer comprising administering any one of the foregoing antibodies to the subject. In some embodiments, the likelihood of survival of the subject is increased for a period of at least 3 months after the treatment compared to the likelihood of survival of a subject not treated with the antibody. In some embodiments, the likelihood of survival of the subject is increased for a period of at least 6 months. In some embodiments, the likelihood of survival of the subject is increased for a period of at least 12 months.

Some embodiments of the compositions, methods and kits provided herein include a method of reducing the risk of recurrence of a cancer in a subject comprising administering any one of the foregoing antibodies to the subject.

Some embodiments of the compositions, methods and kits provided herein include a method of reducing the level of tumor cells of a cancer in the peripheral blood of a subject comprising administering any one of the foregoing antibodies to the subject.

Some embodiments also include administering a chemotherapeutic agent in combination with the antibody. In some embodiments, the chemotherapeutic agent is selected from the group consisting of folinic acid, fluorouracil, irinotecan, gemcitabine and Abraxane. In some embodiments, the folinic acid, fluorouracil, and irinotecan are administered in combination with the antibody to the subject.

In some embodiments, the subject is determined to be predisposed to the cancer by a predictive clinical test, a genetic analysis, or a family history analysis.

In some embodiments, the cancer is selected from the group consisting of colon cancer, colorectal cancer, pancreatic cancer, breast cancer, and lung cancer. In some embodiments, the cancer is selected from the group consisting of colon cancer comprising an APC mutation, colon cancer comprising an KRAS mutation, metastatic colorectal cancer, metastatic pancreatic cancer, triple-negative breast cancer, and small cell lung cancer.

In some embodiments, the subject is mammalian. In some embodiments, the subject is human.

Some embodiments of the compositions, methods and kits provided herein include a method of selecting a treatment for a subject having a tumor comprising: (a) administering a chemotherapeutic agent to the subject; (b) identifying an increased level of a LGR5 polypeptide or a nucleic acid encoding LGR5 in the tumor; and (c) administering any one of the foregoing antibodies to the subject having the increased level of LGR5 polypeptide or a nucleic acid encoding LGR5 in the tumor. In some embodiments, the chemotherapeutic agent is selected from the group consisting of folinic acid, fluorouracil, irinotecan, gemcitabine and Abraxane. In some embodiments, the tumor is selected from the group consisting of colon cancer tumor, colorectal cancer tumor, pancreatic cancer tumor, breast cancer tumor, and lung cancer tumor. In some embodiments, the tumor is selected from the group consisting of colon cancer tumor comprising an APC mutation, colon cancer tumor comprising an KRAS mutation, metastatic colorectal cancer tumor, metastatic pancreatic cancer tumor, triple-negative breast cancer tumor, and small cell lung cancer tumor.

Some embodiments of the compositions, methods and kits provided herein include a method of assessing the efficacy of a treatment with any one of the foregoing antibodies comprising measuring the level of a biomarker in a tumor treated with the antibody. In some embodiments, the biomarker is a nucleic acid or a polypeptide encoded by the nucleic acid, wherein the biomarker selected from the group consisting of WNT6, FZD8, FOSL1, WT11, NFATC1, FZD5, FZD2, FRZB, PRICKLE1, FZDB, FZD7, WNT7B, FBXW11, FZD1, DVL1, CSNK2A1, ANGPT2, AKAP12, ADM, CTNNB1, ALDOC, CDH5, ITGA2, DAB1, MIR655, NKX1-2, ZBTB11, ITPKA, PSMC3IP and BAK1. In some embodiments, a decrease in the level of the biomarker compared to a the level of the biomarker in a tumor not treated with the tumor is indicative of an effective treatment. In some embodiments, the biomarker is selected from the group consisting of WNT6, FZD8, FOSL1, WT11, NFATC1, FZD5, FZD2, FRZB, PRICKLE1, FZDB, FZD7, WNT7B, FBXW11, FZD1, DVL1, CSNK2A1, ANGPT2, AKAP12, ADM, CTNNB1, ALDOC, CDH5, and ITGA2. In some embodiments, an increase in the level of the biomarker compared to a the level of the biomarker in a tumor not treated with the tumor is indicative of an effective treatment. In some embodiments, the biomarker is selected form the group consisting of DAB1, MIR655, NKX1-2, ZBTB11, ITPKA, PSMC3IP and BAK1. In some embodiments, the tumor is selected from the group consisting of colon cancer tumor, colorectal cancer tumor, pancreatic cancer tumor, breast cancer tumor, and lung cancer tumor. In some embodiments, the tumor is selected from the group consisting of colon cancer tumor comprising an APC mutation, colon cancer tumor comprising an KRAS mutation, metastatic colorectal cancer tumor, metastatic pancreatic cancer tumor, triple-negative breast cancer tumor, and small cell lung cancer tumor.

DETAILED DESCRIPTION

Figure 1:
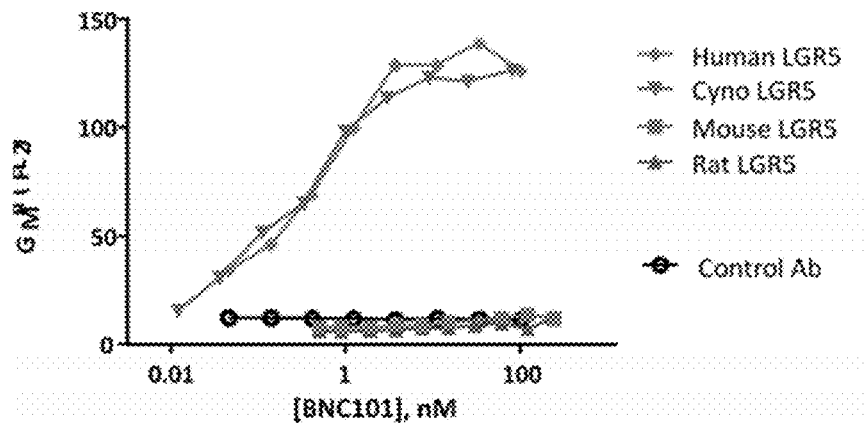
FIG. 1 is a graph showing direct FACS binding of humanized monoclonal antibody 18G7H6A3 to human LGR5 (CHO).

Several embodiments of the present application are drawn to humanized antibodies that specifically bind to LRG5 and methods of inhibiting cancer stem cell growth with such antibodies. In some embodiments, the antibodies specifically bind LGR5 but do not inhibit R-Spo binding to LGR5. Other embodiments include antibodies that bind LGR5 without inhibiting R-Spo signaling through LGR5. Still other embodiments include antibodies that bind LGR5 but do not inhibit both R-Spo binding or signaling through LGR5.

Another embodiment is antibodies that bind LGR5 and also inhibit LGR5 signaling through the Wnt pathway. In some embodiments, these antibodies may inhibit LGR5 signaling through the Wnt pathway, and be independent of RSpo signaling.

Other embodiments include methods of using the antibodies described above to inhibiting LGR5 or R-Spo signaling in a cell or tissue.

LGR5 was identified through lineage tracing studies as a highly specific marker of normal stem cells and tumor-initiating cells in the gut. Previously about 150 genes were identified whose expression was quenched following abrogation of Wnt expression. A comprehensive characterization of these 'Wnt target genes' found LGR5 to be selectively expressed on a population of 10-14 proliferating wedge-shaped cells at the crypt base. These crypt-based columnar cells were previously proposed to be a candidate stem cell population. Using in vivo lineage tracing with a heritable lacZ–LGR5 reporter gene, it has been confirmed that LGR5 intestinal stem cells are a multi-potent, self-renewing population of adult intestinal stem cells that give rise to uninterrupted ribbons of lacZ+ progeny cells initiating from the crypt base and extending to the villus tips.

The specific expression of LGR5 on CSCs provides an opportunity to target CSCs selectively and effectively. LGR5 is highly over expressed in CRC, pancreatic and most other solid tumors, compared to normal tissues, thereby providing a wide therapeutic window to target CSCs in CRC, pancreatic, breast, ovarian, lung, gastric and liver cancer.

LGR5 itself is a facultative component of the Wnt-Fzd-LRP receptor complex that binds secreted R-spondin ligands to selectively amplify and enhance Wnt signals on LGR5 positive cells. There is also evidence that LGR5 can signal in a Wnt-independent manner. In addition, the related transmembrane RING-type E3 ubiquitin ligase ZNRF3 (zinc and RING finger 3) or RNF43 (RING finger 43), are uniquely expressed in LGR5+ stem cells and reduce Wnt signals by selectively ubiquitinating frizzled receptors, thereby targeting these Wnt receptors for degradation. The R-spondin ligands interact with LGR5, to form a ternary complex with the transmembrane ZNRF3 or RNF43. Formation of these ternary complexes sequester ZNRF3 or RNF43 from the Wnt-Fzd-LRP complex and stabilize canonical and noncanonical Wnt signaling. Finally, Norrin has been identified as an additional ligand for the LGR family with unknown associated biology.

The gate keeping mutation in CRC is loss of adenomatous polyposis coli (APC), resulting in the aberrant activation of Wnt signaling, which normally acts to regulate the balance between stem cell self-renewal and differentiation in the colon crypt. Dysregulated Wnt signaling in intestinal stem cells leads to the formation of adenomatous polyps in the colon that are the precursor to malignant CRC. LGR5 stem cells were confirmed to be the source or root of these mouse intestinal tumors, using a strategy that crossed inducible APC gene knockout mice with mice whose LGR5 stem cells were specifically and randomly labeled with one of four (GFP/YFP/ECFP/RFP) fluorescent genetic markers. The appearance of single colored tumors (i.e., all GFP or all RFP) 4 weeks after induction of APC deletion confirmed that these tumors arose from a single LGR5 stem cell. Furthermore, this model also allowed for the fluorescent genetic tag in the LGR5 stem cells to be flipped to a different color, so that an RFP+LGR5 cancer stem cell generating a red tumor could be transformed midstream into a ECFP+ LGR5 cancer stem cell, that was still seeding the tumor but now giving rise to blue tumor cells invading the previously all red GFP+ tumor mass. This flipping experiment not only provided further confirmation that LGR5 CSCs are the origin of intestinal tumors, able to initiate and seed the growth of intestinal tumors, but also that they continuously maintain tumor formation (i.e., have long-term repopulating ability).

A functional role of LGR5 in cancer has been validated through ribonucleic acid interference (RNAi) knockdown studies. Knockdown of LGR5 in a panel of CRC tumor cell lines significantly inhibited the growth of soft agar colonies in vitro, and also the growth of HCT116 colon tumor xenografts in vivo. LGR5 RNAi knockdown was subsequently shown to also reduce the growth of CSC colonies from patient-derived CRC tumor cells in vitro (data not shown). Finally, sorted LGR5+ PATIENT DERIVED XENOGRAFT CRC tumor cells were found to be highly tumorigenic in vivo compared to control LGR5– cells.

CSCs are believed to responsible for the high incidence of tumor recurrence in many cancer patients treated with surgery and standard of care chemotherapy. For example, CD44+CSCs from breast cancer patients were found to be enriched following chemotherapy, and that high levels of CSCs correlated with poor clinical response to chemotherapy. Similarly, in metastatic CRC, LGR5 expression was upregulated in damaged liver following chemotherapy, suggesting that increased LGR5 CSCs in response to chemotherapy initiate and/or acerbate metastatic disease. Indeed, it has been found that LGR5 expression is significantly greater in metastatic sites compared to primary CRC tumors.

Anti-LGR5 Antibodies

As used herein, the term "antibody" includes, but is not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv), Fab fragments, F(ab') fragments, disulfide-linked Fvs (sdFv) (including bi-specific sdFvs), and anti-idiotypic (anti-Id) antibodies, and epitope-binding fragments of any of the above. The antibodies of several embodiments provided herein may be monospecific, bispecific, trispecific or of greater multispecificity. Multispecific antibodies may be specific for different epitopes of a polypeptide or may be specific for both a polypeptide as well as for a heterologous epitope, such as a heterologous polypeptide or solid support material. See, e.g., PCT publications WO 93/17715; WO 92/08802; WO91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148: 1547-1553 (1992); each of which is incorporated herein by reference in its entirety.

As used herein, LGR5 includes, but is not limited to, human LGR5 including the polypeptide of NCBI Accession No. NP_003658.1, or fragments thereof, which is encoded by the coding nucleotide sequence within NM_003667.2, or fragments thereof. The amino acid sequence and entire entry of NCBI Accession No. NP_003658.1 and nucleotide sequence and entire entry of NM_003667.2 are fully incorporated by reference in their entireties. Examples of LGR5 fragments contemplated herein include the LGR5 ectodomain, transmembrane domain, or intracellular domain and portions thereof.

Several embodiments relate to a hybridoma that produces the light chain and/or the heavy chain of an anti-LGR5 antibody, including the anti-LGR5 antibodies designated as 18G7H6A3 and 18G7H6A1 produced and described in the Examples below. In one aspect, the hybridoma produces the light chain and/or the heavy chain of a humanized or fully human monoclonal antibody such as that of 18G7H6A3 and 18G7H6A1 produced and described in the Examples below.

Some embodiments are drawn to a nucleic acid molecule encoding the light chain or the heavy chain of an anti-LGR5 antibody, including any one of the anti-LGR5 antibodies designated as 18G7H6A3 and 18G7H6A1 produced and described in the Examples below. In some aspects, a nucleic acid molecule encodes the light chain or the heavy chain of a humanized or fully human monoclonal, such as antibody 18G7H6A3 and 18G7H6A1 produced and described in the Examples below.

Various embodiments are directed to a vector comprising a nucleic acid molecule or molecules encoding a light chain and/or a heavy chain of an anti-LGR5 antibody, including any one of the anti-LGR5 antibodies designated as 18G7H6A3 and 18G7H6A1 produced and described in the Examples below.

In various embodiments, the glycosylation of the antibodies can be modified. For example, an aglycosylated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861; each of which is incorporated herein by reference in its entirety.

In several embodiments, the antibodies specifically bind a polypeptide comprising or consisting of a LGR5 polypeptide having at least 60% identity, or at least 70% identity, or at least 80% identity, at least 85% identity, at least 90% identity, at least 95% identity, or at least at least 97% identity, or at least 99% identity, or 100% identity to the human LGR5 polypeptide of NCBI Accession Nos. NP_003658.1 (SEQ ID NO: 47) or fragments thereof. Such fragments can, for example, be at least about 5, 10, 15, 20, 25, 50, 75, 100, 150, 200, 250, 300, 350, 400, 450, 500, 550, 600, 650, 700, 750, 800, 850, or 900 contiguous or non-contiguous amino acids of the LGR5 polypeptide, or any number of contiguous or non-contiguous amino acids in between any of the aforementioned lengths.

In several embodiments, the antibody is antibody 18G7H6A3 and comprises a heavy chain amino acid sequence of SEQ ID NO: 13 and a DNA sequence of SEQ ID NO: 11. In some embodiments, the antibody is antibody 18G7H6A3 and has a heavy chain variable domain comprises SEQ ID NO: 19. In several embodiments, the antibody is antibody 18G7H6A3 and comprises a light chain sequence of SEQ ID NO: 14. In other embodiments, the antibody is antibody 18G7H6A3 and comprises a light chain variable domain of SEQ ID NO: 21.

In some embodiments the antibodies comprise a sequence that is 80%, 81%, 82%, 83%, 84%, 85%, 86%, 87%, 88%, 89%, 90%, 91%, 92%, 93%, 94%, 95%, 96% 97%, 98%, 99%, or 100% identical to the sequence of the above sequences. In some embodiments the antibodies comprise a sequence that is 100% identical to the above antibody sequences over a span of 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, or 118 residues of the heavy chain, light chain, or variable domains of the above sequences.

In some embodiments the antibodies comprise a sequence that is 80%, 81%, 82%, 83%, 84%, 85%, 86%, 87%, 88%, 89%, 90%, 91%, 92%, 93%, 94%, 95%, 96% 97%, 98%, 99%, or 100% identical to the antibody sequences. In some embodiments the antibodies comprise a sequence that is 84%, 85%, 86%, 87%, 88%, 89%, 90%, 91%, 92%, 93%, 94%, 95%, 96% 97%, 98%, 99%, or 100% identical to the antibody sequences. In some embodiments the antibodies comprise a sequence that is 100% identical to the antibody sequences of over a span of 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, or 111 residues.

In some embodiments, an anti-LGR5 antibody provided herein comprises a heavy chain CDR1 comprising GYSFTAYW (SEQ ID NO:23), a heavy chain CDR2 comprising ILPGSDST (SEQ ID NO:2), and a heavy chain CDR3 comprising ARSGYYGSSQY (SEQ ID NO:3). In some embodiments, an anti-LGR5 antibody provided herein comprises a light chain CDR1 comprising ESVDSYGNSF (SEQ ID NO:4), a light chain CDR2 comprising LTS, and a light chain CDR3 comprising QQNAEDPRT (SEQ ID NO:33).

In some embodiments, an anti-LGR5 antibody provided herein comprises: (a) a heavy chain CDR1 comprising variants of the above sequences having 1, 2, 3, or 4 amino acid substitutions. The antibody may also have a heavy chain CDR2 having a variant comprising 1, 2, 3, or 4 amino acid substitutions. The antibody may also have a heavy chain CDR3 having a variant comprising 1, 2, 3, or 4 amino acid substitutions. In addition to these modifications of the heavy chain, the antibody may also have a light chain CDR1 having a variant comprising 1, 2, 3, or 4 amino acid substitutions. The antibody may also have a light chain CDR2 having a variant comprising 1, 2, 3, or 4 amino acid substitutions. The antibody may also have a light chain CDR3 having 1, 2, 3, or 4 amino acid substitutions. In some embodiments, the amino acid substitutions are conservative amino acid substitutions.

In some embodiments, an anti-LGR5 antibody provided herein comprises an antibody which comprises a heavy chain variable region having at least 80% or 90% sequence identity to the sequences described herein in the attached sequence listing. The antibody may also have a light chain variable region having at least 80% or 90% sequence identity to the antibody sequences described herein.

The percent identity of two amino acid sequences (or two nucleic acid sequences) can be determined, for example, by aligning the sequences for optimal comparison purposes (e.g., gaps can be introduced in the sequence of a first sequence). The amino acids or nucleotides at corresponding positions are then compared, and the percent identity between the two sequences is a function of the number of identical positions shared by the sequences (i.e., % identity=# of identical positions/total # of positions×100). The actual comparison of the two sequences can be accomplished by well-known methods, for example, using a mathematical algorithm. A specific, non-limiting example of such a mathematical algorithm is described in Karlin et al., Proc. Natl. Acad. Sci. USA, 90:5873-5877 (1993), which is incorporated herein by reference in its entirety. Such an algorithm is incorporated into the BLASTN and BLASTX programs (version 2.2) as described in Schaffer et al., Nucleic Acids Res., 29:2994-3005 (2001), which is incorporated herein by reference in its entirety. When utilizing BLAST and Gapped BLAST programs, the default parameters of the respective programs (e.g., BLASTN) can be used. See http://www.ncbi.nlm.nih.gov, as available on Apr. 10, 2002. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Several embodiments also encompass variants of the above described antibodies, including any one of the anti-LGR5 antibodies designated as 18G7H6A3 and 18G7H6A1 produced and described in the Examples below, comprising one or more amino acid residue substitutions in the variable light ($V_L$) domain and/or variable heavy ($V_H$) domain. Several also encompass variants of the above described antibodies with one or more additional amino acid residue substitutions in one or more $V_L$ CDRs and/or one or more $V_H$ CDRs. The antibody generated by introducing substitutions in the $V_H$ domain, $V_H$ CDRs, $V_L$ domain and/or $V_L$ CDRs of the above described antibodies can be tested in vitro and in vivo, for example, for its ability to bind to LGR5 (by, e.g., immunoassays including, but not limited to ELISAs and BIAcore).

Various embodiments include antibodies that specifically bind to LGR5 comprising derivatives of the $V_H$ domains, $V_H$ CDRs, $V_L$ domains, or $V_L$ CDRs of anti-LGR5 antibodies, such as any one of the anti-LGR5 antibodies designated as 18G7H6A3 and 18G7H6A1 produced and described in the Examples below, that specifically bind to LGR5. Standard techniques known to those of skill in the art can be used to introduce mutations (e.g., additions, deletions, and/or substitutions) in the nucleotide sequence encoding an antibody, including, for example, site-directed mutagenesis and PCR-mediated mutagenesis are routinely used to generate amino acid substitutions. In one embodiment, the $V_H$ and/or $V_L$ CDRs derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original $V_H$ and/or $V_L$ CDRs. In another embodiment, the $V_H$ and/or $V_L$ CDRs derivatives have conservative amino acid substitutions (e.g. supra) made at one or more predicted nonessential amino acid residues (i.e., amino acid residues which are not critical for the antibody to specifically bind to LGR5). Alternatively, mutations can be introduced randomly along all or part of the $V_H$ and/or $V_L$ CDR coding sequence, such as by saturation mutagenesis, and the resultant mutants can be screened for biological activity to identify mutants that retain activity. Following mutagenesis, the encoded antibody can be expressed and the activity of the antibody can be determined.

Several embodiments also encompass antibodies that specifically bind to LGR5 or a fragment thereof, the antibodies comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of any of the antibodies described herein including any one of the anti-LGR5 antibodies including those designated as 18G7H6A3 and 18G7H6A1 produced and described in the Examples below.

Another embodiment includes the introduction of conservative amino acid substitutions in any portion of an anti-LGR5 antibody, such as any one of the anti-LGR5 antibodies designated as 18G7H6A3 and 18G7H6A1 produced and described in the Examples below. It is well known in the art that "conservative amino acid substitution" refers to amino acid substitutions that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several families of conservative amino acid substitutions are shown in Table 1.

TABLE 1

| Family | Amino Acids |
| --- | --- |
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| aromatic | Trp, Tyr, Phe, His |

Blocking Cancer Stem Cell Growth with Anti-LGR5 Antibodies

Several embodiments are drawn to blocking cancer stem cell growth in vitro and in vivo with anti-LGR5 antibodies. In some embodiments, a method of blocking cancer stem cell growth comprises administering an effective amount of an anti-LGR5 antibody to cancer stem cells, wherein the effective amount of the anti-LGR5 antibody is sufficient to reduce growth of the cancer stem cells.

In some embodiments, a method of blocking cancer stem cell growth comprises administering an effective amount of an anti-LGR5 antibody to cancer stem cells, wherein the effective amount of the anti-LGR5 antibody is sufficient to reduce or block proliferation, or reduce or block the growth, of the cancer stem cells.

In some aspects, an effective amount of an anti-LGR5 antibody is administered to cancer stem cells in vitro. In other aspects, an effective amount of an anti-LGR5 antibody is administered to cancer stem cells in a patient in need of treatment thereof, in vivo.

In several embodiments, antibodies against LGR5 are used in methods of inhibiting LGR5 signaling without inhibiting R-Spo binding to LGR5. In several embodiments, antibodies against LGR5 are used in methods of inhibiting LGR5 signaling without inhibiting R-Spo signaling through LGR5. In several embodiments, antibodies against LGR5 are used in methods of inhibiting LGR5 signaling without inhibiting R-Spo binding to LGR5 or signaling through LGR5. In several embodiments, antibodies against LGR5 are used in methods of inhibiting LGR5 signaling through Wnt. In several embodiments, antibodies against LGR5 are used in methods of inhibiting LGR5 signaling through Wnt that is independent of RSpo signaling.

As used herein, the term "cancer stem cell(s)" refers to a cell that can proliferate extensively or indefinitely and give rise to a large proportion of cancer cells in a cancer. In some aspects, the large proportion of cancer cells represents a majority of the cancer cells in a given cancer. For illustration, but not limitation, a cancer stem cell(s) can be a founder of a tumor or a progenitor of the cancer cells that comprise the majority of a cancer's mass. In some aspects, cancer stem cells refer to cells that divide to form one or more tumors when implanted into an immunocompromised individual, in the absence of any additional mutation to the cells or introduction of exogenous cell proliferation-inducing or carcinogenic agents. In some aspects cancer stem cells divide to yield additional cancer stem cells as well as terminally differentiated cancer cells or cancer tissue.

In some embodiments cancer stem cell growth, proliferation, or viability is blocked without interfering with LGR5-RSpo binding or signaling. In some embodiments cancer stem cell growth, proliferation, or viability is blocked without interfering with LGR5-RSpo binding or signaling through blocking or inhibiting LGR5 signaling through Wnt.

As used with respect to blocking cancer stem cell growth, the term "effective amount" refers to an amount of anti-LGR5 antibody sufficient to reduce the growth of cancer stem cells by any degree. Any assay known in the art can be used to measure cancer stem cell growth. For example, cancer stem cell growth can be measured by colony count, total cell count, or volume/size of a cell population or colony. In several embodiments, cancer stem cell growth can be measured by the tumor sphere growth assay described below in Example 1.

In certain embodiments, an effective amount of an anti-LGR5 antibody can block cancer stem cell growth as measured by at least a 5%, 10%, 15%, 20%, 30%, 40%, 50%, 60%, 70%, 80%, 90%, 95%, 96%, 97%, 98%, 99%, or 100% reduction in the cancer stem cell population or tumorsphere growth, or any percentage in between any of the aforementioned numbers. In some aspects, the anti-LGR5 antibody is any one or combination of the anti-LGR5 antibodies designated as 18G7H6A3 and 18G7H6A1 produced and described in the Examples below.

For example, in some embodiments, an effective amount of an anti-LGR5 antibody can block cancer stem cell growth as measured by at least about 5%-99%, a 5%-80%, a 5 to 40%, a 10% to 99%, a 10 to 80%, a 10-60%, a 10%-40%, a 20 to 99%, a 20%-80%, a 20%-60%, a 20%-40%, a 50%-98%, 50%-80%, or a 60%-99% reduction in the cancer stem cell population or tumorsphere growth. In some aspects, the anti-LGR5 antibody is any one or combination of the anti-LGR5 antibodies designated as 18G7H6A3 and 18G7H6A1 produced and described in the Examples below.

In other embodiments, the effective amount of an anti-LGR5 antibody can block cancer stem cell growth as measured by at least about a 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.5, 4.0, 4.5, 5.0, 10, 25, 50, 75, 100, 200, or 1000-fold reduction in the cancer stem cell population or tumorsphere growth, or any fold-reduction in between any of the aforementioned numbers. In some aspects, the anti-LGR5 antibody is any one or combination of the anti-LGR5 antibodies designated as 18G7H6A3 and 18G7H6A1 produced and described in the Examples below.

In some embodiments, the effective amount of an anti-LGR5 antibody sufficient to block cancer stem cell growth by any degree described above is in a concentration of about 1 nM, 50 nM, 75 nM, 100 nM, 150 nM, 200 nM, 250 nM, 300 nM, 350 nM, 400 nM, 500 nM, 550 nM, 600 nM, 700 nM, 800 nM, 900 nM, 1 µM, 50 µM, 75 µM, 100 µM, 150 µM, 200 µM, 250 µM, 300 µM, 350 µM, 400 µM, 500 µM, 550 µM, 600 µM, 700 µM, 800 µM, 900 µM, 1 mM, 5 mM, 10 mM, 15 mM, 20 mM, 25 mM, 30 mM, 35 mM, 40 mM, 45 mM, 50 mM, 75 mM, 100 mM, 200 mM, 300 mM, 400 mM, 500 mM, 600 mM, 700 mM, 800 mM, 900 mM, 1000 mM, 1 M, 5 M, 10 M, 15 M, 20 M, 25 M, 30 M, 35 M, 40 M, 45 M, 50 M, 75 M, 100 M, or any number in between any two of the aforementioned concentrations. In some aspects, an anti-LGR5 antibody composition may comprise both of antibodies designated as 18G7H6A3 and 18G7H6A1 produced and described in the Examples below.

In some embodiments, an anti-LGR5 antibody provided herein binds human LGR5 with a KD of less than about 200 nM, less than about 100 nM, less than about 80 nM, less than about 50 nM, less than about 20 nM, less than about 10 nM, less than about 1 nM, and a range between any of the foregoing values. In some embodiments, an anti-LGR5 antibody provided herein binds LGR5 with an affinity less than about 10 nM, 5 nM, 4 nM, 3 nM, 2 nM, 1 nM, and within a range of any of the foregoing values. In some embodiments, an anti-LGR5 antibody provided herein binds LGR5 with an affinity greater than about 0.0001 nM, 0.001 nM, 0.01 nM, and within a range of any of the foregoing values.

In some embodiments, an anti-LGR5 antibody provided herein binds to an epitope comprising or consisting of or within amino acids T175, E176, Q180, R183, S186, A187, Q189, D247, E248, T251, R254, S257, N258, K260 of SEQ ID NO: 47. In some embodiments, an anti-LGR5 antibody provided herein binds to an epitope comprising or consisting of or within leucine rich repeats 6-9 (See e.g., Chen et al. *Genes Dev.* 27(12):1345-50 which is incorporated by reference in its entirety). In some embodiments, an anti-LGR5 antibody provided herein binds to an epitope comprising or consisting of or within the convex surface of the LGR5 ecto domain (See e.g., Chen et al. *Genes Dev.* 27(12):1345-50 which is incorporated by reference in its entirety).

In some embodiments, an anti-LGR5 antibody provided herein does not significantly disrupt the binding of R-spondin (RSPO) proteins to LGR5. In some embodiments, an anti-LGR5 antibody provided herein does not bind a RSPO-LGR5 binding site. In some embodiments, an anti-LGR5 antibody provided herein does not compete with RSPO for binding to LGR5. In some embodiments, an anti-LGR5 antibody provided herein does not significantly disrupt RSPO activation of Wnt signaling. In some embodiments, an anti-LGR5 antibody provided herein can disrupt LGR5-RSPO-RNF43 complex formation. In some embodiments, an anti-LGR5 antibody provided herein can disrupt LGR5-RSPO-ZNRF3 complex formation. In some embodiments, an anti-LGR5 antibody provided herein can disrupt LGR5-RSPO-LRP6 complex formation. In some embodiments, the RSPO can include R-spondin-1 (RSPO1), R-spondin-2 (RSPO2), R-spondin-3 (RSPO3), and R-spondin-4 (RSPO4). In some embodiments, an anti-LGR5 antibody provided herein can disrupt LGR5-NORRIN-RNF43 complex formation. In some embodiments, an anti-LGR5 antibody provided herein can disrupt LGR5-NORRIN-ZNRF3 complex formation. In some embodiments, an anti-LGR5 antibody provided herein can disrupt LGR5-NORRIN-LRP6 complex formation.

Some embodiments include methods of inhibiting Wnt/β-catenin signaling in a cell. More embodiments include methods of inhibiting NF-κB signaling in a cell. Some of the foregoing methods can include contacting the cell with an effective amount of an anti-LGR5 antibody provided herein.

In some embodiments, the cell is a tumor cell. In some embodiments, the cell can include a colorectal tumor cell, breast cancer cell, lung cancer cell, or a pancreatic tumor cell. In some embodiments, the tumor cell can express elevated levels of LGR5 protein. In some embodiments, the anti-LGR5 antibody provided herein inhibits growth of the tumor cell, for example, by reducing the number and/or frequency of cancer stem cells.

Some embodiments include methods of treating cancer comprising administering a therapeutically effective amount of an anti-LGR5 antibody provided herein to a subject in need thereof. In some embodiments, the cancer is selected from pancreatic cancer, colorectal cancer, lung cancer, pancreatic cancer, and breast cancer, such as triple negative breast cancer. In some embodiments, the colorectal cancer comprises an inactivating mutation in the adenomatous polyposis coli (APC) gene, does not comprise an inactivating mutation in the APC gene, or comprises a wild-type APC gene. In some embodiments, the cancer is. In some embodiments, the cancer comprises elevated levels of LGR5 protein. In some embodiments, the cancer is colon cancer that expresses elevated levels of LGR5. In some embodiments, the cancer is a pancreatic cancer that expresses elevated levels of LGR5, In some embodiments, the cancer is a breast cancer that expresses elevated levels of LGR5.

Some embodiments include methods of treating a disease in a subject wherein the disease is associated with activation of β-catenin, and/or aberrant β-catenin signaling. Some embodiments include administering a therapeutically effective amount of an anti-LGR5 antibody provided herein to a subject in need thereof.

Some embodiments include methods of treating a disease comprising administering a therapeutically effective amount of an anti-LGR5 antibody provided herein to a subject in need thereof in combination with at least one additional therapeutic agent. In some embodiments, the additional therapeutic agent comprises a chemotherapeutic agent. In some embodiments, the additional therapeutic agent comprises a biologic agent. Some embodiments include administering an anti-LGR5 antibody provided herein in combination with a chemotherapeutic agent and a biologic agent. In some embodiments, administering an anti-LGR5 antibody provided herein in combination with a chemotherapeutic agent can increase the expression level of LGR5 in a cancer, such as a tumor. Some embodiments of the methods provided herein include determining the level of LGR5 protein expression in a tumor or cancer.

Some embodiments of the methods provided herein include identifying a subject for treatment with an anti-LGR5 antibody provided herein. Some embodiments include determining if the subject has a tumor comprising an elevated expression level of LGR5 as compared to the expression of the same LGR5 protein in normal tissue. Some embodiments include selecting a subject for treatment if the tumor has an elevated level of LGR5 expression. Some embodiments also include determining if the subject has a tumor that comprises an inactivating mutation in the APC gene. Some embodiments also include selecting a subject for treatment if the tumor comprises an inactivating mutation in the APC gene.

Methods, compositions and related disclosure relevant to the above are provided in, for example, PCT Publication No. WO 2013/067055, published May 10, 2013, the contents of which are hereby incorporated by reference in their entirety, as well as for example, PCT Publication No. WO 2013/067054, published May 10, 2013, the contents of which are hereby incorporated by reference in their entirety, as well as for example, PCT Publication No. WO 2013/067057, published May 10, 2013, the contents of which are hereby incorporated by reference in their entirety, as well as for example, PCT Publication No. WO 2013/067060, published May 10, 2013, the contents of which are hereby incorporated by reference in their entirety.

Kits

Some embodiments provided herein include kits. In some embodiments, a kit can include a humanized antibody provided herein. In some embodiments, the antibody is lyophilized. In some embodiments, the antibody is in aqueous solution. In some embodiments, the kit includes a pharmaceutical carrier for administration of the antibody. In some embodiments, the kit also includes a chemotherapeutic agent. In some embodiments, the chemotherapeutic agent is selected from folinic acid, fluorouracil, irinotecan, gemcitabine and Abraxane.

While the present embodiments have been described in some detail for purposes of clarity and understanding, one skilled in the art will appreciate that various changes in form and detail can be made without departing from the true scope of the invention.

EXAMPLES

Having generally described embodiments drawn to antibodies against LGR5, hybridomas or other cell lines expressing such antibodies, nucleic acids and vectors comprising nucleic acids encoding for such antibodies, and methods of blocking cancer stem cell growth with such antibodies, a further understanding can be obtained by reference to certain specific examples which are provided for purposes of illustration only and are not intended to be limiting.

Example 1

Humanization of LGR5 Antibody

Human germline sequences were used as the acceptor frameworks for humanizing the murine antibody 18G7.1. To find the closest germline sequences, the most similar expressed light chain and the most similar heavy chain were identified in a database of germline sequences by NCI IgBLAST (ncbi.nlm.nih.gov/igblast/). In this search the CDR sequences of 18G7.1 were masked. The selection of the most suitable expressed sequence included checking for sequence identity of the canonical and interface residues, and checking for the similarity in CDR loop lengths.

In order to identify potential structural conflicts in key structural framework residues between the candidate humanized sequence and the parent murine monoclonal antibody 18G7.1, a three-dimensional model was generated. A composite of antibody structures was used to create a homology model with grafted candidate humanized sequences followed by molecular energy minimization. Structural analysis using computer software Pymol, was used to identify residues that could potentially negatively impact proper folding.

From this analysis, six candidate VH chains were constructed that included: 1) a functional human framework containing selected substitutions within the candidate humanized framework region based on analysis of likely impact on folding and ii) the parental 18G7.1 murine antibody CDRs (SEQ ID NOs: 1, 2, and 3). fused in-frame to the human IgG1 constant region are chemically synthesized.

Similarly, two candidate VL chains were constructed that included: 1) a functional human framework containing selected substitutions within the candidate humanized framework region based on analysis of likely impact on folding and ii) the parental 18G7.1 murine antibody CDRs (SEQ ID NOs: 4, 5, and 6). The candidate VL chain and the candidate VH chain fused in-frame to the human IgG1 constant region were chemically synthesized.

Selected candidate variant humanized heavy and light chain combinations were tested for functionality by co-transfection into mammalian cells. Each of the six candidate humanized 18G7.1 heavy chains described above were co-transfected with one of the candidate 18G7.1 light chains into HEK 293 cells, and conditioned media was assayed for LGR5 antigen binding activity by flow cytometry. In addition, three candidate humanized 18G7.1 heavy chains described above were co-transfected with the second candidate 18G7.1 light chain into HEK 293 cells, and conditioned media was assayed for LGR5 antigen binding activity by flow cytometry. The 18G7.1 candidate heavy chain/light chain combination (humanization variant) known as 18G7H6, and which exhibited the most robust binding was selected for affinity maturation.

Example 2

Humanized LGR5 Antibody Affinity Maturation

In order to increase the affinity of the selected humanized variant 18G7H6, a combination of alanine scanning mutagenesis and saturation mutagenesis was employed. Residues in heavy chain CDR1 and light chain CDR1 and CDR3 were mutated to alanine, transfected into HEK 293 cells, and the resultant conditioned media was assayed for LGR5 antigen binding activity by flow cytometry. Saturation mutagenesis was performed on heavy chain CDR3, in which every residue in CDR3 was mutated to each of the 19 naturally occurring amino acids except the original amino acid identity at that position. Each of the mutants were transfected into HEK 293 cells, and the resultant conditioned media was assayed for LGR5 antigen binding activity by flow cytometry.

These mutations were incorporated at increasing number into 3 constructs. These three constructs were then transfected into HEK 293 cells, and the resultant conditioned media was assayed for LGR5 antigen binding activity by flow cytometry. Two constructs 18G7H6A1 and 18G7H6A3 were selected for further characterization. TABLE 1A lists certain sequences of the antibodies.

TABLE 1A

| Description | SEQ ID NO: |
|---|---|
| 18G7.1 Heavy Chain CDR1 Amino Acid | 1 |
| 18G7.1 Heavy Chain CDR2 Amino Acid | 2 |
| 18G7.1 Heavy Chain CDR3 Amino Acid | 3 |
| 18G7.1 Light Chain CDR1 Amino Acid | 4 |
| 18G7.1 Light Chain CDR2 Amino Acid | 5 |
| 18G7.1 Light Chain CDR3 Amino Acid | 6 |
| 18G7H6A1 Heavy Chain DNA | 7 |
| 18G7H6A1 Light Chain DNA | 8 |
| 18G7H6A1 Heavy Chain Amino Acid | 9 |
| 18G7H6A1 Light Chain Amino Acid | 10 |
| 18G7H6A3 Heavy Chain DNA | 11 |
| 18G7H6A3 Light Chain DNA | 12 |
| 18G7H6A3 Heavy Chain Amino Acid | 13 |
| 18G7H6A3 Light Chain Amino Acid | 14 |
| 18G7Ch Heavy Chain DNA | 15 |

TABLE 1A-continued

| Description | SEQ ID NO: |
| --- | --- |
| 18G7Ch Light Chain DNA | 16 |
| 18G7Ch Heavy Chain Amino Acid | 17 |
| 18G7ch Light Chain Amino Acid | 18 |
| 18G7H6A3 Heavy Chain Variable Domain Amino Acid | 19 |
| 18G7H6A3 Heavy Chain Variable Domain DNA | 20 |
| 18G7H6A3 Light Chain Variable Domain | 21 |
| 18G7H6A3 Light Chain Variable Domain DNA | 22 |
| 18G7H6A3 Heavy Chain CDR1 Amino Acid | 23 |
| 18G7H6A3 Heavy Chain CDR1 DNA | 24 |
| 18G7H6A3 Heavy Chain CDR2 Amino Acid | 25 |
| 18G7H6A3 Heavy Chain CDR2 DNA | 26 |
| 18G7H6A3 Heavy Chain CDR3 Amino Acid | 27 |
| 18G7H6A3 Heavy Chain CDR3 DNA | 28 |
| 18G7H6A3 Light Chain CDR1 Amino Acid | 29 |
| 18G7H6A3 Light Chain CDR1 DNA | 30 |
| 18G7H6A3 Light Chain CDR2 Amino Acid | 31 |
| 18G7H6A3 Light Chain CDR2 DNA | 32 |
| 18G7H6A3 Light Chain CDR3 Amino Acid | 33 |
| 18G7H6A3 Light Chain CDR3 DNA | 34 |
| 18G7H6A1 Heavy Chain CDR1 Amino Acid | 35 |
| 18G7H6A1 Heavy Chain CDR1 DNA | 36 |
| 18G7H6A1 Heavy Chain CDR2 Amino Acid | 37 |
| 18G7H6A1 Heavy Chain CDR2 DNA | 38 |
| 18G7H6A1 Heavy Chain CDR3 Amino Acid | 39 |
| 18G7H6A1 Heavy Chain CDR3 DNA | 40 |
| 18G7H6A1 Light Chain CDR1 Amino Acid | 41 |
| 18G7H6A1 Light Chain CDR1 DNA | 42 |
| 18G7H6A1 Light Chain CDR2 Amino Acid | 43 |
| 18G7H6A1 Light Chain CDR2 DNA | 44 |
| 18G7H6A1 Light Chain CDR3 Amino Acid | 45 |
| 18G7H6A1 Light Chain CDR3 DNA | 46 |
| LGR5 Amino Acid Sequence | 47 |
| 18G7H6A1 Heavy Chain Variable Amino acid | 48 |
| 18G7H6A1 Light Chain Variable Amino acid | 49 |

Example 3

Production of Humanized LGR5 Antibodies

GS single gene vectors for 18G7H6A1, 18G7H6A3 and a chimeric 18G7.1 (murine Fab from 18G7.1 fused to human IgG1 Fc), named 18G7Ch were constructed, amplified and transiently co-transfected into Chinese Hamster Ovary cells (CHOK1SV GS-KO) using transient transfection for expression evaluation at a volume of 200 ml. Large scale transient transfection of CHOK1SV GS-KO cells at a final volume of 5 liters for 18G7CH and 2.5 liters for both 18G7H6A1 and 18G7H6A3 was then initiated. Clarified culture supernatant was purified using one-step Protein A chromatography. Product quality analysis in the form of SE-HPLC, SDS-PAGE and endotoxin measurement was carried out using purified material at a concentration of 1 mg/ml including an in-house human antibody as a control sample. Results showed high purity of product recovered (>95.7%).

Example 4

Construction of the Cell Line for a Humanized LGR5 Antibody

Stable GS-CHO transfectant pools, expressing the 18G7H6A3 antibody were created by transfection of CHOK1SV GS-KO host cells with the expression vector p18G7H6A3/DGV. The DGV containing the gene encoding the antibody was constructed, transfected and resultant clonal cell lines were subsequently generated by single cell sorting of the transfectant pools using a FACS method. The 96-well plates generated during cloning were screened weekly for the presence of single colonies. After approximately 2 weeks, supernatant from up 1000 colonies were screened for antibody production using an Octet® System method. Of the 1000 colonies screened, 991 produced detectable levels of antibody. The Octet data were ranked and the highest producing colonies were selected for progression.

The highest ranked colonies were progressed to suspension culture in 96-deep well plates in CD CHO medium and were subsequently adapted to subculture medium. Productivity of the selected cell lines were performed using a feed regime which mimicked, as closely as possible, the bioreactor process. The cultures were harvested on day 12 and assayed for antibody concentration using an Octet® System method. Antibody concentrations at harvest ranged from <20 mg/L to 3000 mg/L. Twenty cell lines were selected for further evaluation based upon rank position in the productivity screen, the parental pool from which the cell line was derived and evidence that each cell line arose from a single colony. The cultures of the 20 selected cell lines were expanded by serial subculture from 96 deep well plates to shake-flasks. Based upon rank position in the 'abridged' fed-batch suspension culture productivity screen and having acceptable growth characteristics during routine subculture in shake-flask cultures (consistently ≥1×106 viable cells per mL at routine subculture), the lead cell line selected for evaluation in two 10 L laboratory-scale stirred-tank bioreactors. This lead cell line demonstrated consistently high growth and viability during routine subculture and has >2000 mg/L titers at harvest. This cell line was used for creation of the Master Cell Bank (MCB) and for evaluation in 10 L laboratory-scale bioreactors

Example 5

Humanized LGR5 Antibody Binds to Human LGR5

A FACS-based assay was used to measure the binding of purified 18G7H6A1 and 18G7H6A3 to recombinant human LGR5 overexpressed on the surface of CHO cells. CHO and CHO-LGR5 cells were stained with serial dilutions of 18G7H6A1 or 18G7H6A3 at 4° C., surface staining was detected with PE-conjugated anti-human IgG secondary antibodies and analyzed on the FACScalibur. The EC50 of 18G7H6A1 and 18G7H6A3 for human LGR5 binding was <10 nM. An antibody control (MOPC) was used as a negative control in this experiment as well as wild-type CHO without LGR5. 18G7H6A3 showed no binding to the wild-type CHO and the isotype control did not show any measurable binding to human LGR5.

To identify potential animal model species for investigating the therapeutic efficacy and safety of 18G7H6A3, the cross-reactivity of 18G7H6A3 to LGR5 expressed by species homologues was determined in a series of in vitro binding studies. See FIG. 1. As shown, antibody 18G7H6A3 (BNC101) was found to strongly bind human and cyno LGR5, but not bind to rat or mouse LGR5.

Example 6

Binding of a Humanized LGR5 Antibody to Plate-Bound Recombinant, Human LGR5 Ectodomain Binding of 18G7H6A1 and 18G7H6A3 to human LGR5 was assessed in vitro using an ELISA-based plate binding assay. The assay measured antibody binding to ELISA plate-bound purified recombinant, LGR5 ectodomain-IgG-Fc fusion, with detection of LGR5-bound antibody with horseradish peroxidase-conjugated anti-human IgG-CH1 secondary antibody. The EC50 of 18G7H6A3 for human LGR5-Fc was found to be 300 pM.

Example 7

Binding Characteristics of a Humanized LGR5 Antibody on Tumor Cells

The binding characteristics of 18G7H6A3 to human cancer cell lines expressing different levels of LGR5, were analyzed by flow cytometry to define the potential targeting properties of 18G7H6A3 on heterogeneous tumor populations. The expression levels of LGR5 in multiple tumor cell lines were quantified by flow cytometry.

Human tumor cell lines analyzed in these studies included colon carcinoma cancer cell lines (CT1 (Bionomics), CT3 (Bionomics), DLD1 (ATCC), Ls174T (ATCC), LoVo (ATCC), SW48 (ATCC), SW480 (ATCC), SW620 (ATCC) and HCT116 (ATCC)), triple negative breast cancer cell lines (Hs578T (ATCC) and MDA-MB-231 (ATCC)), pancreatic cancer cell lines (AsPC-1 (ATCC), BxPC3 (ATCC), Capan2 (ATCC), HPAFII (ATCC), SW1990 (ATCC), CFPAC (ATCC), Panc10.05 (ATCC) and PANC-1 (ATCC)), cisplatin-sensitive ovarian cancer cell lines (OVCAR3 (ATCC) and SK-OV-3 (ATCC)), cisplatin-resistant ovarian cancer cell lines (SK-OV-3/CP, OVCAR8/CP, Igrov1/CP and A2780/CP (TGEN)) and lung adenocarcinoma cell line HOP62 (ATCC).

Cells grown near confluence were lifted with TrypLE cell dissociation buffer (Life Technologies), counted and plated in 96-well V-bottom plates at 1×105 cells per well. 18G7H6A3 was tested at a starting concentration of 100 nM with serial dilutions in staining buffer (PBS/0.8% bovine serum albumin). Samples were incubated on ice for 30 minutes, then centrifuged at 1800 rpm for 2 minutes at 4° C. and washed 3 times with staining buffer. Fifty μl of secondary antibody goat anti-human IgG-PE conjugate at 1:250 dilution (Southern Biotech) was added to each corresponding well in staining buffer. Samples were incubated for an additional 15 minutes on ice, and then washed as described above and resuspended in 100 μl staining buffer containing propidium iodide (PI) (Life Technologies) for dead cell exclusion. Samples were analyzed on the FACScalibur flow cytometer using CellQuest (Becton Dickinson) and FlowJo (TreeStar, Inc) software.

The cell surface expression levels of LGR5 in multiple tumor cell lines were quantified by flow cytometry. CT1 colorectal tumor cells and pancreatic cancer cell lines Panc-1, Capan2 and CFPAC were among the highest LGR5 expressors. Moderate expression levels were observed in pancreatic cancer cell lines (AsPC-1, SW1990, HPAFII), cisplatin-resistant ovarian cancer cell lines (OVCAR8/CP, A2780/CP and Igrov1/CP) as well as colon, breast and ovarian cancer cell lines (SW48, Hs578T and OVCAR3). Low but detectable levels of LGR5 cell surface expression were observed in colon (SW480, LoVo) and breast cancer cell lines (MDA-MB-231). Table 2 summarizes the data for 18G7H6A3 FACS binding to Tumor cell lines.

TABLE 2

| Tumor Cell line | 18G7H6A3 (18G7.1) | IgG |
|---|---|---|
| CRC | | |
| CT1 | + | − |
| CT3 | + | − |
| DLD1 | +/− | − |
| Ls174T | +/− | − |
| LoVo | +/− | − |
| SW48 | + | − |
| SW480 | +/− | − |
| SW620 | +/− | − |
| HCT116 | +/− | − |
| Breast | | |
| MDA-MB-231 | +/− | − |
| MDA-MB-231 LM2 | +/− | − |
| Hs578T | + | − |
| CN34 | +/− | − |
| CN34 LM1 | +/− | − |
| Prostate | | |
| PC-3 | +/− | − |
| PCSD1 | +/− | − |
| Ovarian | | |
| OVCAR-3 | + | − |
| SK-OV-3 | +/− | − |
| SK-OV-3/CP | +/− | − |
| OVCAR8/CP | + | − |
| Igrov1/CP | + | − |
| A2780/CP | + | − |
| Lung | | |
| HOP-62 | +/− | − |
| Pancreatic | | |
| AsPC-1 | + | − |
| Capan2 | ++ | − |
| HPAFII | + | − |
| Sw1990* | + | − |
| CFPAC | ++ | − |
| PANC-1 | ++ | − |

Example 8

Inhibition of Cachectic Colorectal Tumor Growth In Vivo by a Humanized Anti-LGR5 Antibody The CT1 primary CRC xenograft model was derived from a patient with stage IV metastatic colon cancer. DNA sequencing of this tumor identified common colon cancer mutations in multiple genes including K-Ras, PI3K, PTEN, p53 and APC. Low passage CT1 tumorspheres maintained in culture under serum-free conditions were injected into SCID/Bg mice in Matrigel subcutaneously on day 0, and monitored twice weekly for tumor size and body weight. At day 25 CT1 subcutaneous tumors were randomized into groups of 10 mice when tumors reached 120 mm3. Mice were treated with either PBS, antibody control MOPC, 18G7H6A1, 18G7H6A3 or human/murine chimeric 18G7Ch. Mice were dosed BIW at 15 mg/kg for 2.5 weeks (5 doses total).

Antibody 18G7H6A3 showed significant anti-tumor activity in vivo compared to PBS and MOPC antibody controls during the course of 4 doses (15 mg/kg, twice weekly). While antibody 18G7H6A1 showed anti-tumor activity, monoclonal 18G7H6A3 showed superior activity to both 18G7H6A1 and the parental murine chimeric 18G7Ch antibody. Table 3 shows percent CT1 tumor volume reduction (group vs MOPC) after 1-4 doses of Lgr5+ Abs.

TABLE 3

| # of Doses: | 1 | 2 | 3 | 4 |
|---|---|---|---|---|
| 18G7Ch | 9.2% | 30.6% | 19.5% | 29.0% |
| 18G7H6A1 | 17.5% | 19.1% | 14.2% | 19.0% |
| 18G7H6A3 | 38.8% | 42.0% | 28.9% | 35.4% |

Example 9

Inhibition of Colorectal Tumor Growth In Vivo by a Humanized Anti-LGR5 Antibody

The CT3 primary CRC xenograft model was derived from a patient with stage III mCRC with mutations in K-Ras, H-Ras, APC, PI3K, PTEN, STK11, RB1, TP53, FGFR2, VANGL2, and ISCO. Low passage cryopreserved CT3 primary xenograft tumor fragments were implanted into 5 SCID/Bg mice. Tumors averaging ~1150 mm3 pooled from five CT3 primary xenograft-bearing SCID mice were removed at day 41 post-implant, dissociated and re-implanted into CB.17 SCID mice in Matrigel subcutaneously, and monitored twice weekly for tumor size and body weight. When tumors reached an average of 130 mm3, mice were randomized (34 days post implant). Mice were treated with either PBS, antibody control MOPC, 18G7H6A3, 18G7H6A1 or human/murine chimeric 18G7Ch. Mice were dosed BIW at 15 mg/kg for 2.5 weeks (5 doses), starting on day 34. All mice were monitored twice weekly for body weight and tumor size, as well as overall health and appearance, until termination.

While antibody 18G7H6A1 showed anti-tumor activity, monoclonal 18G7H6A3 showed significant anti-tumor activity compared to PBS and MOPC antibody controls after 4 doses (15 mg/kg, twice weekly). 18G7H6A3 showed superior activity to the parental murine chimeric 18G7Ch antibody and equivalent activity to 18G7H6A1. Table 4 shows percent CT3 tumor volume reduction (group vs MOPC) after n dose of test Abs.

TABLE 4

| # of Ab Doses: | 1 | 2 | 3 | 4 |
|---|---|---|---|---|
| 18G7Ch | 22.6% | 8.9% | 17.0% | 13.8% |
| 18G7H6A1 | 18.3% | 12.6% | 28.8% | 28.7% |
| 18G7H6A3 | 34.2% | 38.1% | 23.4% | 28.2% |

Example 10

Figure 2:
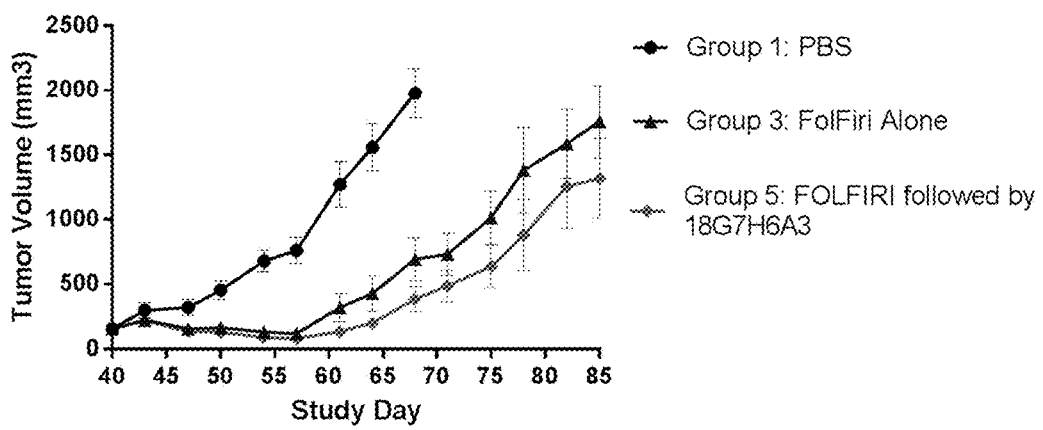
FIG. 2 is a graph showing the effect of FOLFIRI, alone and in combination with 18G7H6A3, on CT3 CRC tumor volume.

Inhibition of Colorectal Tumor Growth In Vivo by a Humanized Anti-LGR5 Antibody in Combination with FOLFIRI CB.17 SCID mice were implanted with CT3 cells grown under CSC conditions. At day 40 post-implantation, when tumors reached ~160 mm3, mice were randomized into treatment groups including i) PBS, ii) FolFiri (5FU 30 mg/kg, leucovorin 90 mg/kg and Irinotecan 24 mg/kg), given every 5 days for for 15 days (3 doses total), and iii) Combination of FolFiri (as in ii.) and 18G7H6A3 (15 mg/kg twice per week). Analyses of tumor volume showed that combination of 18G7H6A3 and FolFiri reduced growth of CT3 tumors compared to FolFiri regimen. Combination treatment reduced tumor volume at days 61, 65, 68, 71 and 75 by about 58%, 53%, 45%, 33% and 37% respectively (FIG. 2).

Example 11

Inhibition of Pancreatic Cancer Tumor Growth In Vivo by a Humanized Anti-LGR5 Antibody To assess efficacy of 18G7H6A3 as single agent or in combination with standard of care, a pancreatic cancer xenograft model was tested. CB17.SCID mice were implanted with AsPC-1 cells (in matrigel+RPMI in a 1:1 ratio). Tumors were randomized at day 20 post implantation into 5 groups: i) PBS, ii) MOPC (15 mg/kg, twice per week, ip), iii) 18G7H6A3 (15 mg/kg, twice per week, ip), iv) gemcitabine (90 mg/kg, twice per week, ip) and v) concurrent combination of gemcitabine and 18G7H6A3 at the above doses.

It was discovered that 18G7H6A3 as single agent inhibited tumor growth compared to saline and/or control IgG up to nearly 40% at day 41 post implantation. In addition, the combination of 18G7H6A3 and gemcitabine significantly inhibited tumor growth in AsPC-1 model (up to 36% at day 61 post implantation) compared to gemcitabine alone. 18G7H6A3 as single agent also provided some inhibition in tumor growth compared to PBS and control IgG up to day 65.

Example 12

Figure 3:
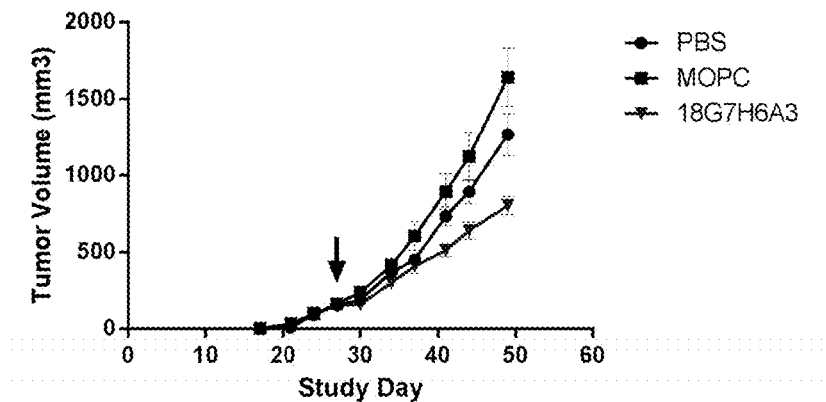
FIG. 3 is a graph showing 18G7H6A3 treatment significantly reduced MDA-MB-231-LM3 primary tumor volume.

Inhibition of Triple Negative Breast Cancer Tumor Growth In Vivo by a Humanized Anti-LGR5 Antibody This in vivo study was performed using low passage triple negative breast cancer cells (ER-, PR-, no HER2 overexpression). MDA-MB-231-LM3 cells were maintained in adherent culture with DMEM/10% FBS/anti-anti medium. CB.17 SCID mice were injected on day 0 with MDA-MB-231-LM3 cells in RPMI:Matrigel (1:1) into the 4th mammary fat pad and monitored twice weekly for tumor size and body weight. At day 27, MDA-MB-231-LM3 tumors were randomized into 4 groups of 10 mice when tumors reached ~155 mm$^3$. Mice were treated with PBS, antibody control MOPC, or 18G7H6A3. Mice were dosed BIW at 15 mg/kg for 3.5 weeks (7 doses). It was discovered that antibody 18G7H6A3 showed significant anti-tumor activity compared to PBS (60.7% tumor growth inhibition) or MOPC antibody (49.3% tumor growth inhibition) controls (FIG. 3).

Example 13

Induction of Expression of LGR5 in Colorectal Cancer Cells Treated with a SN38 or a PI3K/mTOR Inhibitor A panel of CRC cell lines including DLD1, HCT116, LS174t, LoVo, SW48, SW480 and SW620 were treated with a PI3K/mTOR dual inhibitor (NVP) or 2 different cytotoxic agents including SN38 (active metabolite of Irinotecan) or 5FU (5 fluorouracil). Cells were treated with the above agents at 1 um and were harvested after 72 hrs. Cells were then stained with anti-LGR5 Mab conjugated to Alexa Fluor647 and the data were analyzed by flow cytometry using a FACScalibur.

Flow cytometry analyses of CRC cell lines showed greater expression of LGR5 in LoVo, HCT116, LS174t, SW48, SW480 and SW620 cells when treated with a PI3K/mTOR inhibitor. Additionally, treatment with SN38 promoted LGR5 expression in HCT116, LS174t, SW48, SW480 and especially SW620 cells. 5FU treatment, however, did not induce LGR5 expression in any of these lines suggesting that underlying mechanisms governing LGR5 expression are distinct in these lines. These data indicate that LGR5+ cells are more resistant to treatment with the above agents as treatments have mostly targeted the LGR5 negative non-cancer stem cell population. To understand if treatment with these agents upregulate LGR5 expression on these cells, we analyzed LGR5 cell surface expression by flow cytometry in all the cell lines. Upon treatment with PI3K/mTOR inhibitor, LGR5 expression was significantly upregulated in LoVo. These data indicate that treatment with small molecule inhibitors or cytotoxic agents target LGR5neg cells and causes increased expression of LGR5 in these cells.

Example 14

LGR5 Expression is Promoted in Pancreatic Cancer Cell Lines Treated with Small Molecule Inhibitors or Cytotoxic Agents In addition to CRC cell lines to further expand the above findings, expression of LGR5 was investigated in a series of pancreatic cell lines treated with relevant standard of care including nab-paclitaxel, gemcitabine and taxol and also small molecule inhibitors targeting most relevant pathways in pancreatic cancer such as inhibitors of PI3K, MEK and GSK3β. The pancreatic cell lines that were tested include: AsPc1, HPAFII, PANC1, BxPc3, CFPAC, PANC10.05, Capan2 and SW1990. Treatment with nab-paclitaxel results in LGR5 upregulation in PANC1, BxPc3 and PANC10.05 as assessed by flow cytometry. Gemcitabine treatment upregulates LGR5 in PANC1 and taxol treatment results in increased LGR5 expression in HPAFII. The PI3K/mTOR treatment results in upregulation of LGR5 in CFPAC and the MEK inhibitor upregulates LGR5 in HPAFII and SW1990.

Example 15

LGR5 is Upregulated in Colorectal Cancer Tumors Treated with FOLFIRI Regimen (5FU, Leucovorin and Irinotecan)

Figure 4:
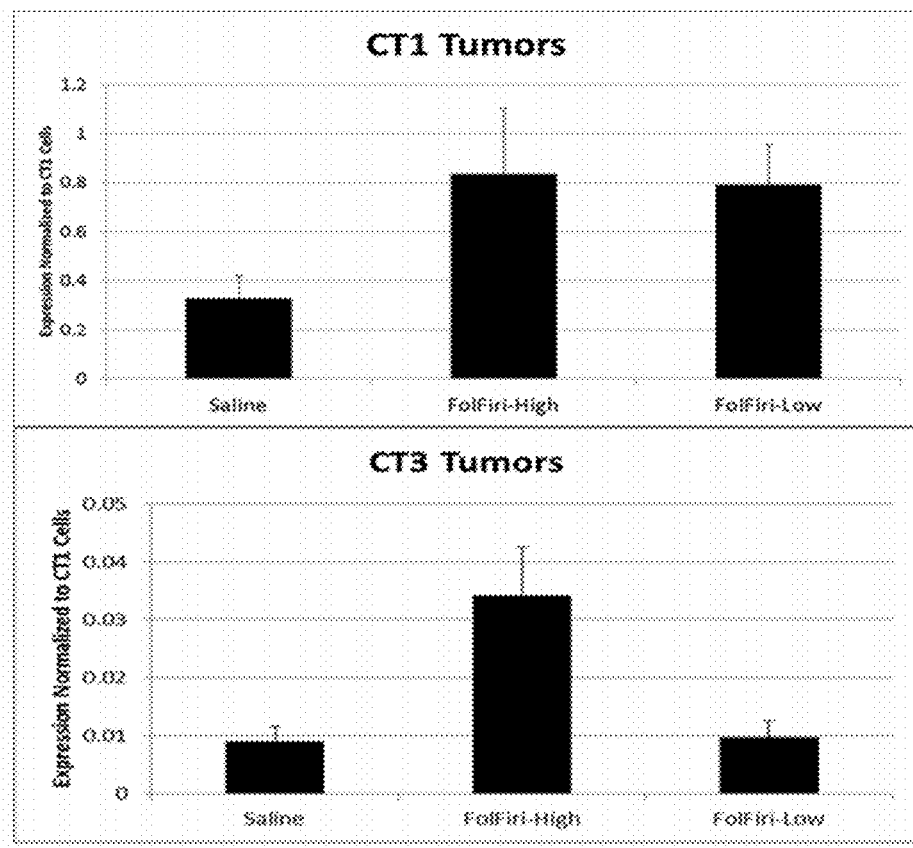
FIG. 4 shows graphs of FolFiri treatment in mice bearing CT1, or CT3 tumors results in upregulation of LGR5.

To investigate if chemo treatment alters LGR5 expression in colorectal tumors, mice were treated every 5 days with 5FU (30 mg/kg i.p), leucovorin (90 mg/kg) and 2 different doses of irinotecan (24 mg/kg or 8 mg/kg). The result of those studies showed that while CT3 tumors were sensitive to the chemo regimen, CT1 tumors did not full regress and showed some resistance to the regimen (FIG. 4). To examine the effect of FOLFIRI treatment of LGR5 expression, total mRNA was extracted from CT1 and CT3 patient derived tumors and expression of LGR5 and was determined by qRT-PCR and was analyzed by subtracting the Ct value (cycle threshold) of LGR5 in each sample from its corresponding GAPDH transcript to generate DCT (delta Ct) values. Data are presented as 2 to the power of DCT. Analyses of abundance of LGR5 showed that the LGR5 transcript is increased in both CT1 (for about 2 folds) and CT3 tumors (approximately 3.5 folds) compared to corresponding saline treated tumors.

Example 16

LGR5 is Upregulated in Pancreatic Cancer Tumors Treated with Gemcitabine Alone and in Combination of nab-Paclitaxel To investigate if standard of care chemotherapy treatment for pancreatic cancer alters LGR5 expression in pancreatic tumors, mice were treated twice per week with combination of gemcitabine and nab-paclitaxel (in JH109 primary xenografts). At terminal analysis, qRT-PCR data using tumor cDNA showed a remarkable increase in the expression of LGR5 in chemotherapy treated tumors compared to corresponding saline-treated tumors indicating that treatment with standard of care results in upregulation of LGR5 in tumor cells.

Figure 5:
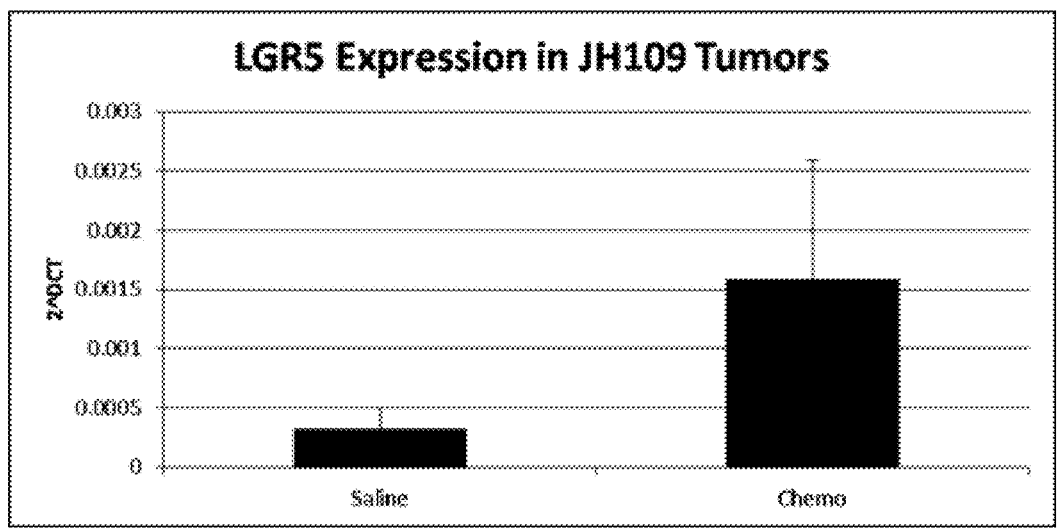
FIG. 5 is a bar chart showing chemotherapy results in upregulation of LGR5 (more than 4-fold) in JH109 tumors.

LGR5 expression in JH109 model which is a patient derived xenograft model of pancreatic tumor. Mice were implanted with tumor chunks that were continuously passaged in the recipient but were never exposed to in vitro culture condition. Treatment of tumor-bearing mice with a chemotherapy regimen (combination of gemcitabine and nab-paclitaxel) resulted in a significant inhibition in tumor growth. Consistent with the colon cancer models, chemotherapy resulted in upregulation of LGR5 (more than 4-fold) in JH109 tumors, further suggesting enrichment of the cancer stem cell population upon treatment with chemotherapy. See, for example, FIG. 5.

Example 17

Inhibition of Pancreatic Tumor Growth In Vivo by a Humanized Anti-LGR5 Antibody

Efficacy of 18G7H6A3 was also investigated in a pancreatic cancer xenograft model. CB.17 SCID mice were implanted with PANC1 cells (1E6/mouse s.c in matrigel+RPMI 1:1 ratio), and randomized at day 41 post implantation into treatment groups: i) PBS, ii) IgG control (15 mg/kg, twice per week, ip), iii) 18G7H6A3 (15 mg/kg, twice per week, ip), iv) gemcitabine (90 mg/kg, twice per week, ip) and v) concurrent combination of gemcitabine and 18G7H6A3 (15 mg/kg, twice per week, ip). Gemcitabine was administered in assigned group for 3 weeks to inhibit tumor growth. All mice were monitored twice weekly for body weight and tumor size, as well as overall health and appearance.

Figure 6:
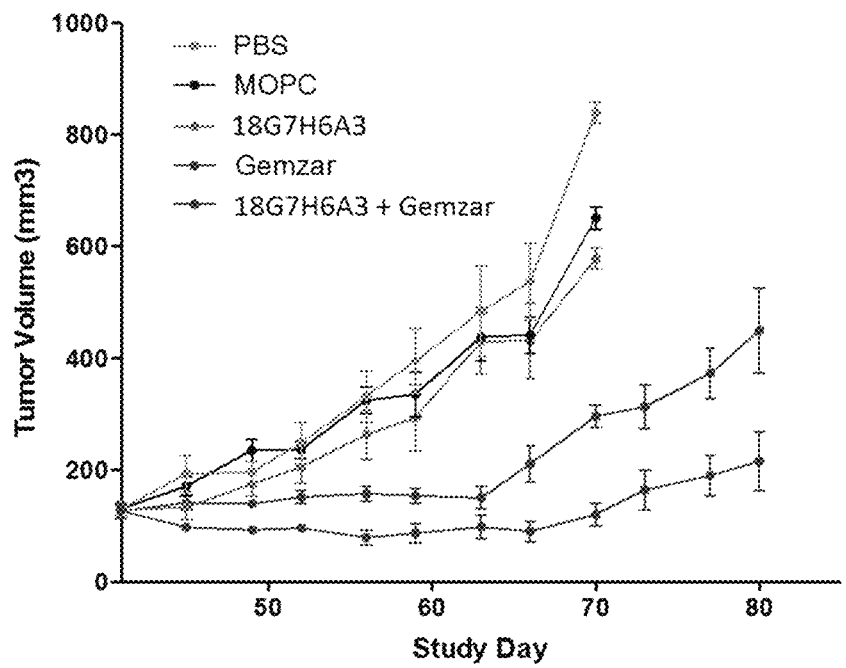
FIG. 6 is a graph showing significant activity of 18G7H6A3 observed when administered in combination with chemotherapy (gemcitabine).

Analysis of tumor volume showed that while there is a trend in favor of 18G7H6A3 as single agent (up to 30% at day 70 post implantation) to inhibit tumor growth, combination of 18G7H6A3 and gemcitabine significantly inhibited growth of PANC1 tumors (up to 52% at day 80 post implantation) compared to gemcitabine alone group. See FIG. 6.

In this example, the significant activity of 18G7H6A3 observed when administered in combination with chemotherapy (gemcitabine) can be attributed to the increased expressed of the target antigen LGR5 in response to gemcitabine treatment.

Example 18

Inhibition of Pre-Treated Pancreatic Tumor Growth In Vivo by a Humanized Anti-LGR5 Antibody In addition to cell lines, we also investigated the efficacy of 18G7H6A3 as single agent or in combination with standard of care in the JH109 primary patient derived xenograft model of pancreatic cancer. The JH109 xenograft model is from a patient that had received four treatment regimens including 5-FU, Gemcitabine, Erbitux and radiotherapy. The original patient tumor has been passaged in immune-deficient mice continuously without any exposure to in vitro culture. To test efficacy of 18G7H6A3 in JH109 model, tumor bearing mice (n=7) were treated with control IgG (15 mg/kg i.p twice/week), 18G7H6A3 (15 mg/kg i.p twice/week) single agent, standard of care chemo (combination of gemcitabine (50 mg/kg i.p once week; and nab-paclitaxel 30 mg/kg, i.v once a week), combination of chemo and control IgG, and combination of chemo and 18G7H6A3. While single 18G7H6A3 mAb did not affect tumor growth, combination of 18G7H6A3 with Nab-paclitaxel and gemcitabine chemotherapy led to a significantly greater degree of tumor inhibition compared to chemotherapy alone. 18G7H6A3 combined with chemotherapy led to 77% greater tumor growth inhibition compared to chemotherapy alone. Three mice treated with the 18G7H7A3 chemotherapy combination had complete eradication of their tumor (no measureable tumor detected). The 18G7H6A3 chemotherapy combination group continued to suppress tumor growth even after discontinuation of treatment and one mouse was still devoid of any measurable tumors three months after cessation of chemotherapy. In this example, the significant activity of 18G7H6A3 observed when administered in combination with chemotherapy (gemcitabine plus nab-paclitaxel) can be attributed to the increased expressed of the target antigen LGR5 in response to gemcitabine nab-paclitaxel treatment and is a demonstration of prevention of re-growth or recurrence of a primary tumor in vivo after chemotherapy treatment to eradicate the primary tumor bulk.

Example 19

Humanized LGR5 Antibody Treatment Reduces Cancer Stem Cell Populations

For flow cytometric analysis, cells from 5 individual tumors were stained with a variety of antibodies against stem cell specific markers CD44, and CD166. Tumors were dissociated, depleted for mouse cells and then counted for viable cells. Dissociated cells were used for analysis of cell surface stem cell marker expression by flow cytometry.

Figure 7:
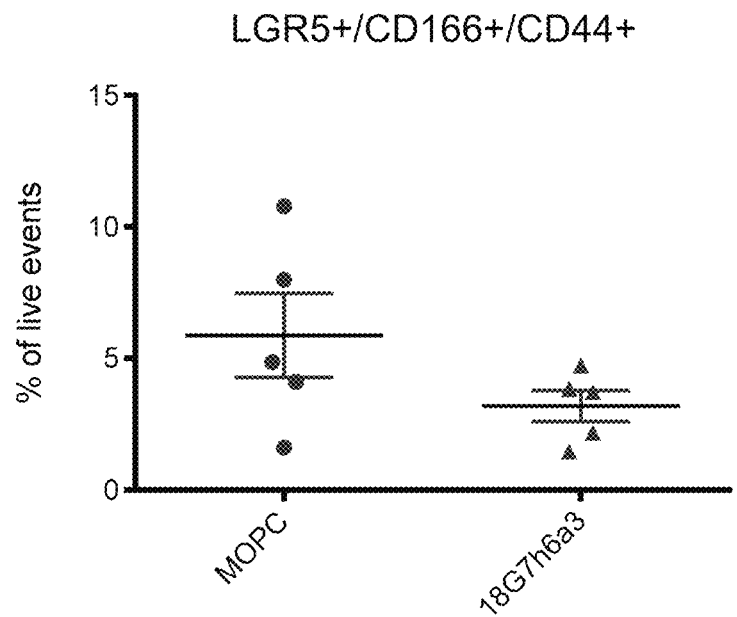
FIG. 7 is a point plot showing that antibody 18G7H6A3 reduces the number of live events in a CT1 cancer stem cell population.

There was a decrease in cancer stem cell population as defined by CD166+/CD44+, LGR5+/CD166+, or LGR5+/CD166+/CD44+ subpopulations (FIG. 7).

Example 20

Humanized LGR5 Antibody Treatment Reduces Colon Cancer Tumor Recurrence and Cancer Stem Cell Frequency In Vivo The effects of 18G7H6A3 in combination with FolFiri were tested in colon cancer CT3 model (Example 10). The results of this primary tumor efficacy study showed that 18G7H6A3 in combination with a 3 cycle FOLFIRI regiment was more effective than FolFiri alone in reducing tumor growth. To determine if the 18G7H6A3 FOLFIRI combination regimen was also effective in reducing cancer stem cell (CSC) frequency, tumors from day 78 were harvested, dissociated, pooled and re-implanted in a limiting dilution assay at 10, 30, 100 cells/flank into a new cohort of tumor naïve CB17.Scid mice. The mice were then monitored 2× per week for tumor growth, and tumors allowed to grow with no further treatment.

Figure 8:
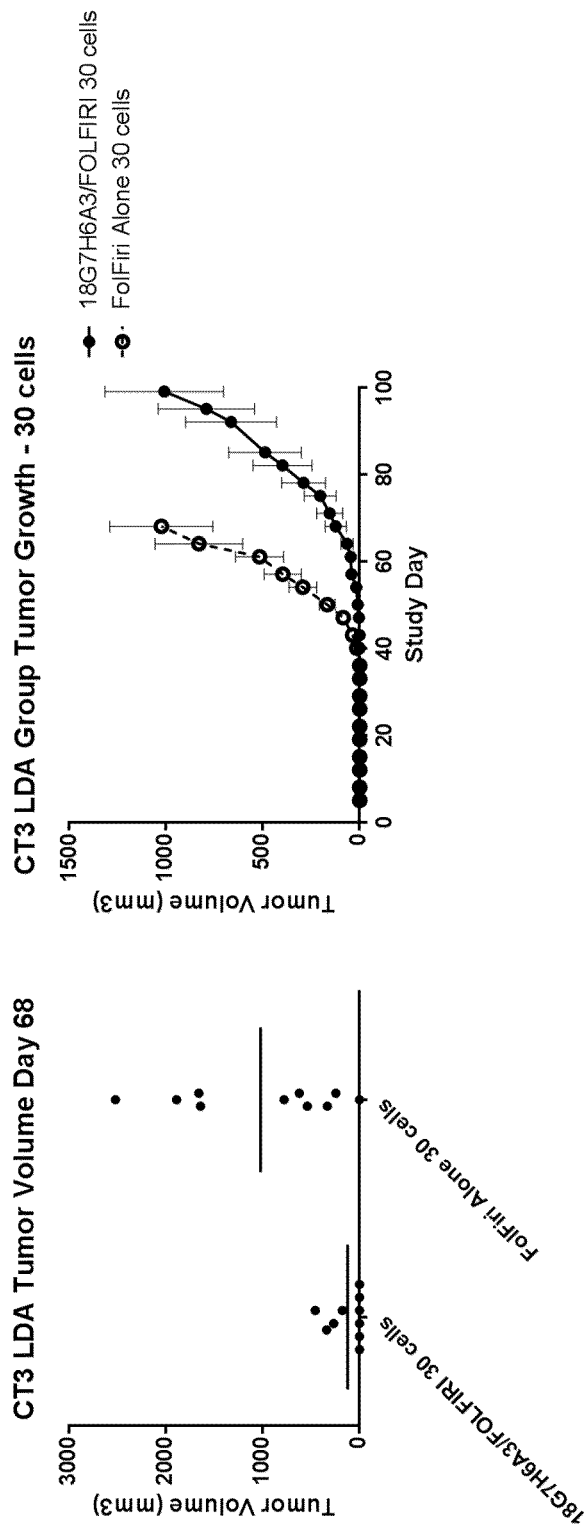
FIG. 8 is a line graph showing cells isolated from mice treated with anti-LGR5 antibody 18G7H6A3 in combination with FOLFIRI had greatly decreased tumorigenicity as compared to cells isolated from mice treated with FOLFIRI alone.
Figure 9:
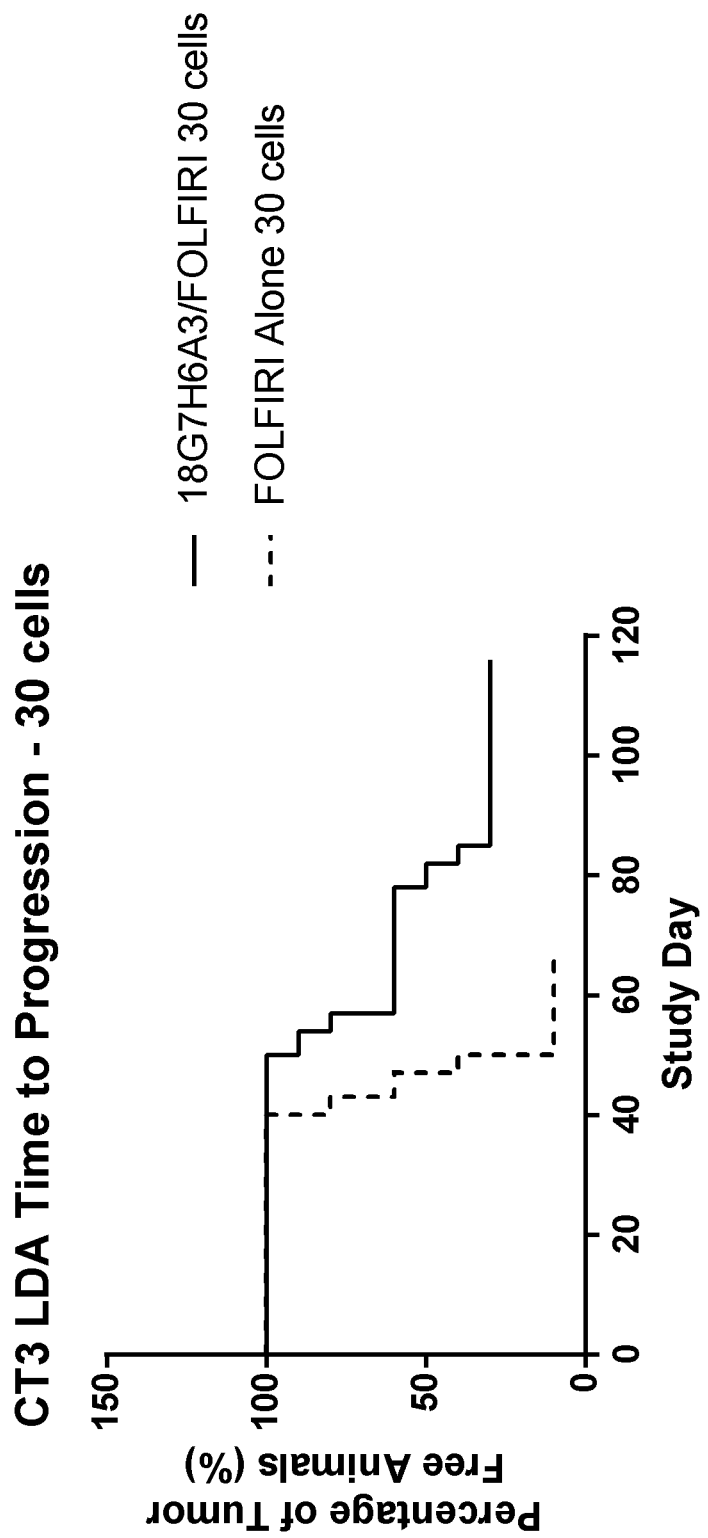
FIG. 9 is a line graph showing that re-implanted cells from the 18G7H6A3 FOLFIRI combination had a significantly delayed time to progression.

Cells isolated from mice treated with anti-LGR5 antibody 18G7H6A3 in combination with FOLFIRI had greatly decreased tumorigenicity as compared to cells isolated from mice treated with FOLFIRI alone (FIG. 8). In addition, the re-implanted cells from the 18G7H6A3 FOLFIRI combination had a significantly slower tumor growth profile and a delayed time to progression (FIG. 9) compared to FOLFIRI alone. Finally, the 18G7H6A3 treatment reduced cancer stem cell frequency by a linear regression analysis by a factor of 6 at day 40 (1/856.3 18G7H6A3/FOLFIRI vs 1/138.6 for FolFiri). These data indicate that 18G7H6A3 in combination with FOLFIRI effectively targets the tumor initiating or cancer stem cell population. Day 68 was the last day for the 30 cells/animal data. The data are significant at p=0.0039.

Example 21

Humanized LGR5 Antibody Treatment Reduces Pancreatic Cancer Tumor Recurrence and Cancer Stem Cell Frequency In Vivo The effects of 18G7H6A3 in combination with gemcitabine were tested in pancreatic cancer PANC1 model. This study showed that 18G7H6A3 in combination with gemcitabine significantly inhibited tumor growth in PANC1 model compared to gemcitabine alone. Tumors cells from these treatment groups were harvested, dissociated, pooled and re-implanted in a limiting dilution assay (500, 1500, 4500 or 13500 cells/animal) into a new cohort of CB.17 SCID mice and allowed to grow with no treatment.

Cells isolated from mice treated with anti-LGR5 antibody 18G7H6A3 in combination with gemcitabine had greatly decreased tumorigenicity in the limiting dilution assay re-implant as compared to cells isolated from mice treated with gemcitabine alone. Re-implanted PANC1 tumors treated with combination of gemcitabine and 18G7H6A3 showed reduction in the frequency of engraftment in mice implanted with 4500 cells (40% in gemcitabine vs. 20% in combination) and also in mice implanted with 13500 cells (100% in gemcitabine vs. 70% in combination). Using linear regression, frequency of cancer stem cell in gemcitabine implanted tumors was about 1.5 fold higher in gemcitabine compared to combination group (1 in 14883 vs. 1 in 21336). These data indicate that 18G7H6A3 in combination with gemcitabine effectively targets the tumor initiating or cancer stem cell population.

In addition to PANC1 tumors, we also analyzed percentage of engraftment and cancer stem cell frequency in an limiting dilution experiment (using 500, 1500, 4500 and 13500 cells) in mice bearing AsPC-1 tumors treated with gemcitabine as single agent or in combination with 18G7H6A3. Tumor volume measurement at day 40 post treatment showed a reduction in percentage of tumor bearing mice in gemcitabine vs. combination in mice implanted with 4500 or 13500 cells (40% and 80% vs. 30% and 50%, respectively). Frequency of cancer stem cells was also greater by more than 1.5 fold in gemcitabine vs. combination group further indicating that 18G7H6A3 in combination with gemcitabine is targeting cancer stem cell population in pancreatic cancer.

Example 22

Humanized LGR5 Antibody Treatment Reduces Triple Negative Breast Cancer Tumor Recurrence and Cancer Stem Cell Frequency In Vivo The effects of 18G7H6A3 in combination with paclitaxel were tested in the triple negative breast cancer MDA-MB-231-LM3 model (Example 12). This study showed that 18G7H6A3 in combination with paclitaxel had minimal additive inhibition in tumor growth compared to paclitaxel alone. These tumors were harvested, dissociated, pooled and re-implanted in a limiting dilution assay at 10, 30, 100 cells/flank into a new cohort of CB.17 SCID mice and allowed to grow with no treatment.

Cells isolated from mice treated with anti-LGR5 antibody 18G7H6A3 in combination with paclitaxel had greatly decreased tumorigenicity as compared to cells isolated from mice treated with paclitaxel alone. In addition, the re-implanted cells from the 18G7H6A3 plus paclitaxel tumors had a significantly slower tumor growth profile and a delayed time to progress compared to paclitaxel alone. Finally, the 18G7H6A3 plus paclitaxel treatment reduced cancer stem cell frequency by a linear regression analysis. These data indicate that 18G7H6A3 in combination with paclitaxel effectively targets the tumor initiating or cancer stem cell population.

Example 23

Figure 10:
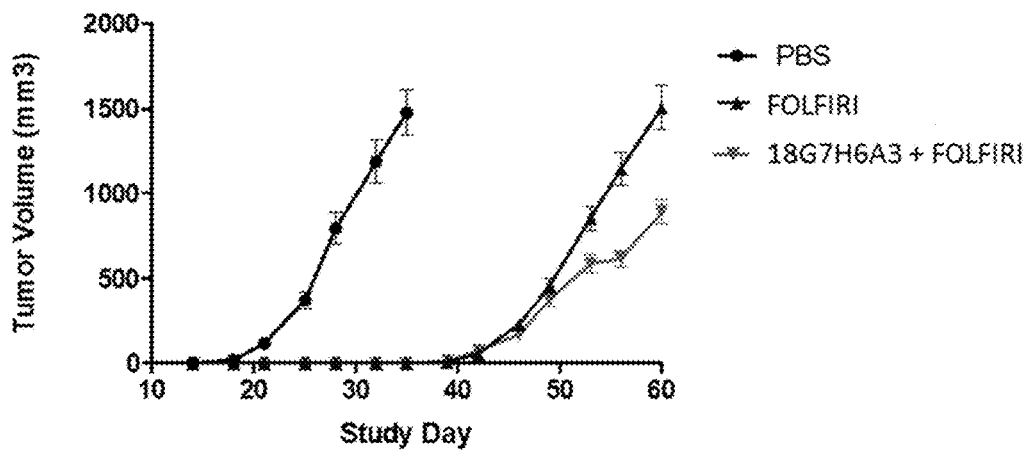
FIG. 10 is a line graph showing significant activity of humanized antibody 18G7H6A3 is observed when administered prophylactically in combination with chemotherapy (FOLFIRI).

Inhibition of Metastatic Colorectal Cancer Growth In Vivo by Prophylactic Treatment with Humanized Anti-LGR5 Antibody and Chemotherapy The in vivo study was performed using low passage colorectal cancer cells (BMCRC086) derived from a liver met of a patient with colorectal cancer. On Day 0, BMCRC086 cells were thawed, suspended in RPMI:Matrigel (1:1) and injected subcutaneously into the rear flank of CB.17 SCID mice. Animals were monitored twice weekly for tumor size and body weight. At day 7, mice were treated with PBS, 18G7H6A3, FOLFIRI or FOLFIRI in combination with 18G7H6A3. Mice were dosed with PBS and 18G7H6A3, BIW at 15 mg/kg for 7.5 weeks (16 doses). Mice were dosed with FOLFIRI (30 mg/kg Fluorouracil and 90 mg/kg Leucovorin on days 7, 12, 17, 22, 27 and 32; 24 mg/kg Irinotecan on days 8, 13, 18, 23, 28 and 33) for 4 weeks (6 doses). 18G7H6A3 in combination with FOLFIRI showed significant anti-tumor activity compared to FOLFIRI alone (FIG. 10).

Example 24

Humanized LGR5 Antibody Treatment Inhibits Wnt Signaling Pathways

Figure 11:
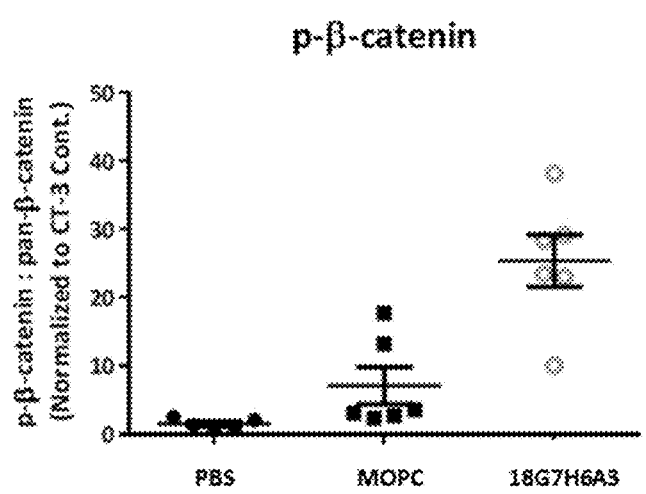
FIG. 11 is a point plot showing that antibody 18G7H6A3 is able to inhibit Wnt signaling in tumor cells in vivo as indicated by phospho-Thr41/Ser45-β-catenin immunoassays.

18G7H6A3 treated tumors from colon cancer CT1 (Example 8) and CT3 (Example 9) in vivo tumor efficacy studies were characterized by western blot analysis. Tumor samples from each treated mouse (n=5 to 10 mice per group) were resected after sacrificing, immediately frozen in a liquid nitrogen cooled mortar, ground-up pestle (cryopulverization), flash frozen in liquid nitrogen and stored at −80° C. until used. Cryopulverized tumors were lysed with ice cold lysis buffer (reducing RIPA buffer containing phosphatase and protease inhibitors) for 30 minutes on ice with occasional vortexing. Supernatants containing tumor lysate protein were run on a SDS-PAGE gel followed by western blotting for a number of Wnt-signal proteins (and their phosphorylated forms). A number of significant differences between treatment groups were observed in western blots of CT1 and CT3 tumors. In FIG. 11, phospho-Thr41/Ser45-β-catenin (a Wnt-signal protein) is a marker of inactive, and subsequently degraded, form of the protein demonstrating 18G7H6A3 is able to inhibit LGR5 signaling in tumor cells in vivo.

Example 25

Humanized LGR5 Antibody Treatment does not Inhibit In Vitro Wnt-Signaling Pathway Parental HEK-293T cells and HEK-293T cell stably expressing LGR5 were transduced with a TCF-LEF reporter vector-containing lentivirus (GFP Cignal, QIAGEN) and selected for stable expression of the reporter. Parental and LGR5 expressing stable reporter lines were plated at 25,000/well in a 96 well plate, attached overnight, serum starved and treated with antibodies or vehicle for 6 h, then treated with recombinant human Wnt3a (3 nM) and recombinant human R-spondins for 18 h. Two concentrations for each R-spondins1-3 and one concentration of R-spo4 were tested (100 pM, 300 pM, 1 nM,3 nM or 10 nM) based on our analysis of the activity of the different R-spondins in activation of the TCF/LEF reporter cell lines. The reporter driven GFP signal was measured on a plate reader. All experiments shown are pooled data from three independent experiments (each experiment performed in duplicate) for each R-spondin tested (data are means+SD).

Figure 12:
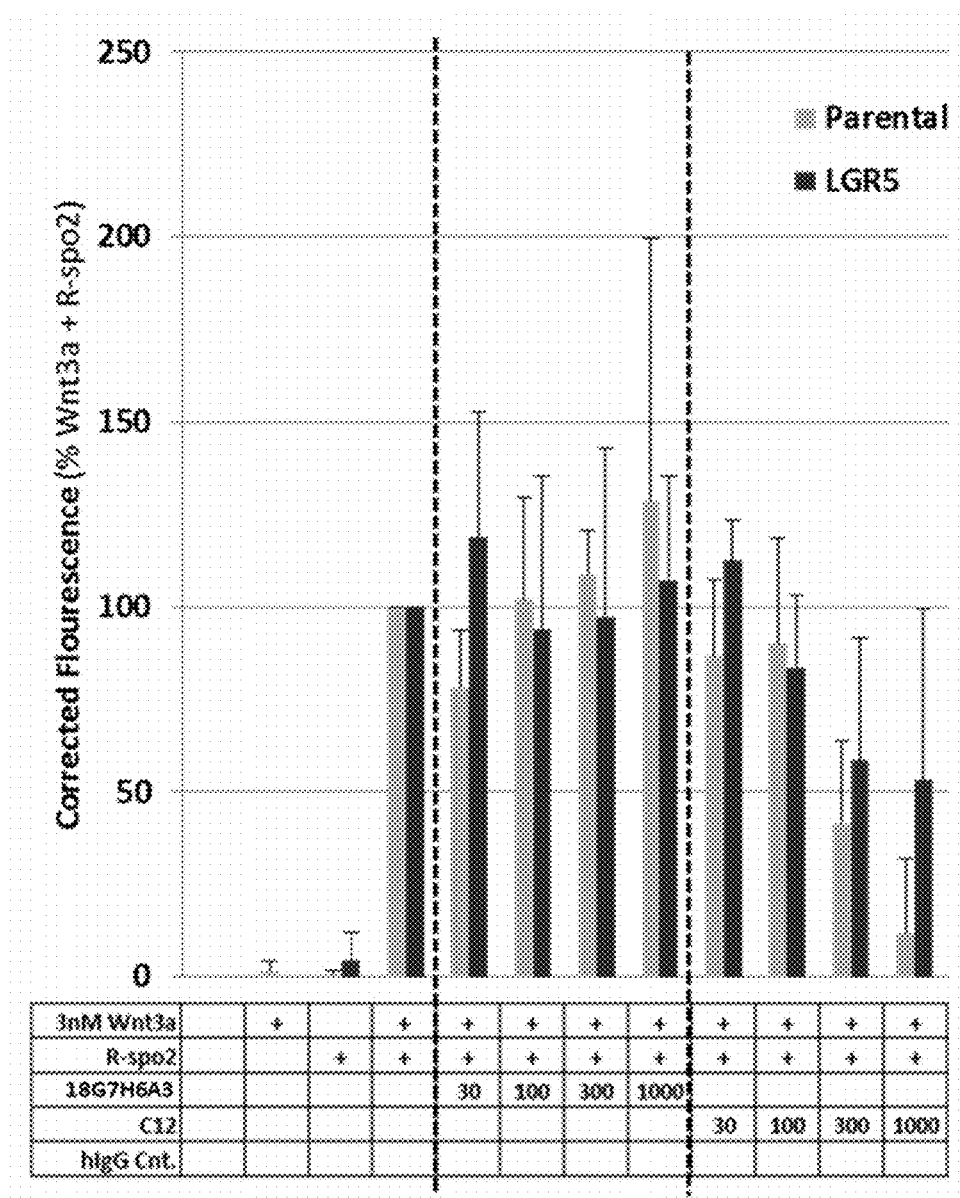
FIG. 12 is a bar chart showing that increasing concentrations of soluble antibody 18G7H6A3 did not affect the induction of TCF/LEF promoter driven GFP expression by the combination of Wnt3a plus RSPO2, demonstrating that the anti-LGR5 antibody 18G7H6A3 does not block RSPO-driven TCF/LEF promoter activation. A positive control antibody C12 is shown to inhibit Wnt3a/RSPO2 driven TCF/LEF promoter activitation.

As shown in FIG. 12, increasing concentrations of soluble 18G7H6A3 did not affect the induction of TCF/LEF promoter driven GFP expression by the combination of Wnt3a plus RSPO1, RSPO2 or RSPO3. A positive control antibody 76C12, which has been shown to inhibit the induction of signaling activity through both LGR4 and LGR5 in the presence of RSPO and Wnt, is also shown. This data demonstrates that the anti-LGR5 antibody 18G7H6A3 does not block RSPO-driven TCF/LEF promoter activation.

Example 26

Humanized LGR5 Antibody Targets Tumor Cells Via ADCC (Antibody Dependent Cell Cytotoxicity) Mechanism CHO-LGR5 cells were grown to confluent and were spun down, resuspended in PBS and were counted. An aliquot of cells (approximately 100 k) were added to another tube containing 100 µM pre-warmed (37° C.) CFSE (Carboxyfluorescein succinimidyl ester) and the mixture was incubated in the cell incubator for 15 min. The final CFSE concentration was about 1 µM. Next, cells were washed and resuspended in pre-warmed medium and were placed in the incubator for another 30 minutes followed by washing with PBS. The stained cells were then stained with 18G7H6A3 (100 µM). To ensure binding of the antibody to CHO-LGR5 cells, in some studies an aliquot of cells was also stained with a secondary goat anti-human PE conjugated antibody and was analyzed on the calibur machine in the laboratory. The U937 cells were stained with DDAO-SE (DDAO succinimidyl ester; 2 µM of dye for 100K cells) for 15 minutes and in a light protected place in the laboratory and at room temperature. Cells were then 1 ml of FBS (fetal bovine serum) followed by incubation in a light protected place for 5 minutes. Next, cells were washed with PBS supplemented with FBS (10%) and were resuspended in RPMI supplemented with FBS (2.5%). Both CHO-LGR5-18G7H6A3 and U937-DDAO-SE labeled cells were co-incubated in the cell incubator for 5 hrs and were analyzed in the calibur machine in the laboratory. As a negative control, an aliquot of CHO-LGR5-CFSE cells (no 18G7H6A3 staining) was also co-incubated with U937 and was analyzed on the calibur machine.

Analysis of flow cytometry data showed that majority of CHO-LGR5 cells stained with CFSE and 18G7H6A3 are viable and detectable in the calibur machine. Additionally, both U937 (U937 (human monocyte cell line; effector cells) and CHO-LGR5 cells were detectable when stained and were acquired individually. Finally co-incubation of U937-DDAO-SE and CHO-LGR5-CFSE-18G7H6A3 identified a double positive population of cells, however, co-incubation of U937 and CHO-LGR5-CFSE which lacks 18G7H6A3 did not generate the double positive population. The presence of the double positive population is indicative of a cross binding of U937 (which express FcR) to CHO-LGR5-18G7H6A3 (which express Fc portion) and further suggests that ADCC is one of the mechanisms of anti-tumor activity of 18G7H6A3.

Example 27

Humanized LGR5 Antibody Internalizes LGR5

Internalization of 18G7H6A3 was examined on CHO cell overexpressing LGR5. Cells were stained with 100 nM antibody for 30 min-2 hrs at 4° C., excess Ab was washed off and stained cells were incubated at either 4° C. or 37° C. Cells were stained with AlexaFluor488-conjugated secondary antibodies at various time points to monitor internalization of cell surface-bound antibodies. Upon incubation at 37° C., the internalized rate had a measured t1/2 value for surface localization of 6.703±1.282 minutes. Internalization was largely blocked by incubation at 4° C. although some decrease in surface-bound antibody was observed.

Example 28

Humanized LGR5 Antibody does not Competitively Block Binding of Soluble RSPOs to LGR5

Interaction of biotin-18G7H6A3 with hLGR5-Fc in the presence of human R-spondin 1/2/3/4 proteins was examined using competition ELISA format. LGR5-Fc was coated on a 96-well high binding ELISA plate at 2 μg/mL, and incubated overnight at 4 C. The plate was blocked with PBS +1% BSA. Biotin-18G7H6A3 was diluted in binding buffer to 1 μg/mL. The concentration was chosen from previous direct binding ELISA between LGR5-Fc and biotin-18G7H6A3 to give robust signal above EC50 concentration. Competitor proteins were added to the ELISA plate at the same time as biotin-18G7H6A3 at varying concentrations. A dilution of 1:1,000 of streptavidin-HRP (R&D Systems, cat #890803) was used for detection. Plate was developed with TMB (Thermo), and data were collected on SpectraMax Plus 384 plate reader at 450 nm. Data analysis was done using GraphPad Prism 6 program. The ELISA was repeated three times with some modifications of biotin-mAb and competitor concentrations.

Figure 13:
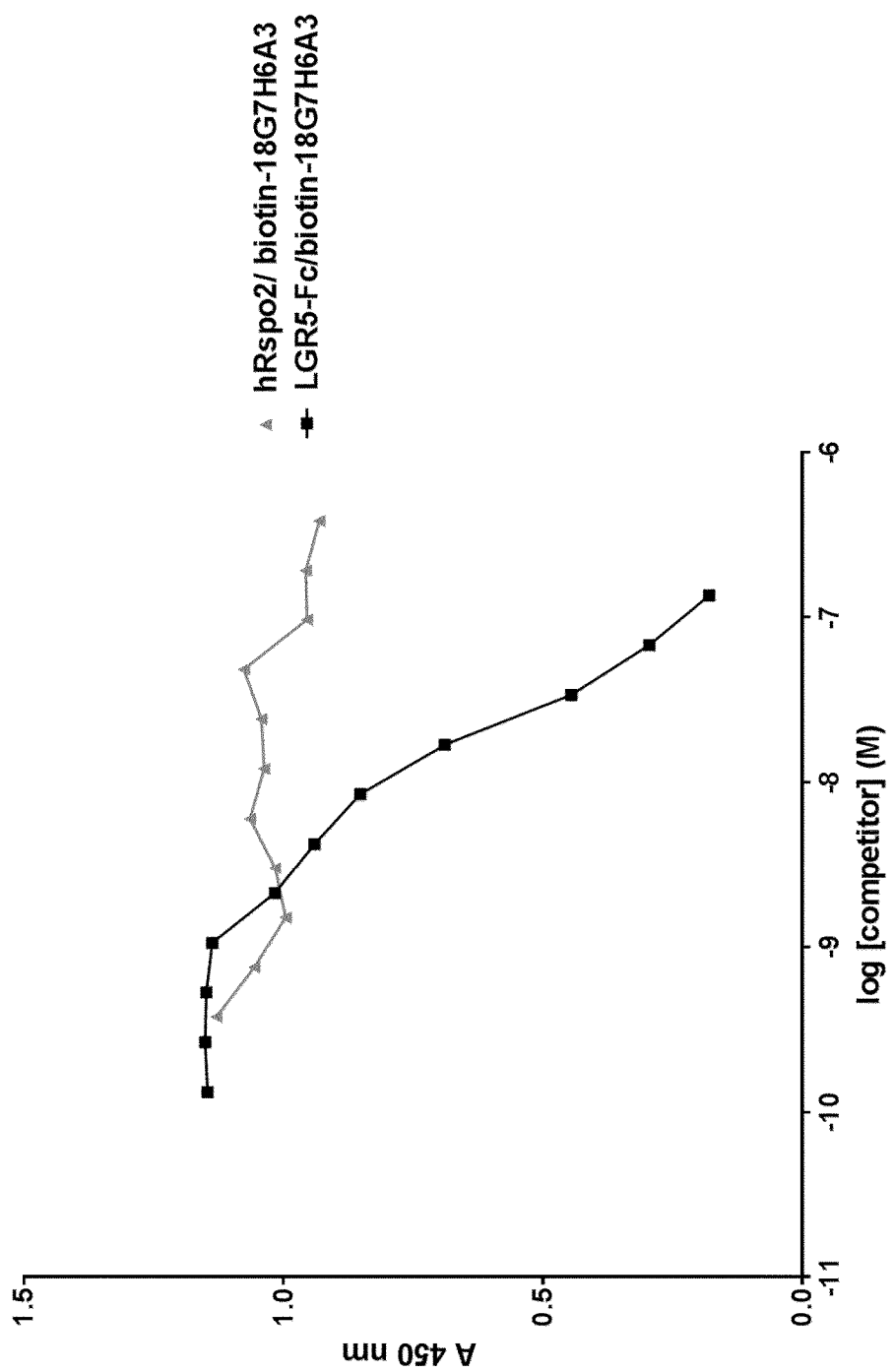
FIG. 13 is a line graph showing that R-spondin does not block antibody 18G7H6A3 binding to LGR5.

As a positive control, LGR5-Fc was competed with the binding of biotin-18G7H6A3 to hLGR5-Fc on the plate. R-spondins 1/2/3/4 were tested for the ability to block binding of biotin-18G7H6A3 to LGR5-Fc coated on the plate. The proteins were purchased from R&D Systems, and are full length constructs expressed in mammalian cells. At the highest concentration of R-spondin proteins, complete blocking of antibody binding to LGR5 was not observed (FIG. 13).

Example 29

Humanized LGR5 Antibody does not Competitively Block Binding of Soluble RSPOs to LGR5

Binding of ligand alone (RSPO or Norrin) to LGR5 is not sufficient to induce LGR5 signaling. Instead, LGR5 forms ternary complexes with multiple co-receptors to drive signaling. To examine the effects of 18G7H6A3 on the formation of LGR5 ternary complexes, the binding of LGR5 to RNF43, ZNRF3, and LRP6 in the presence of R-spondin 1/2/3/4 and Norrin was examined using an ELISA format. RNF43-Fc, ZNRF3-Fc, and LRP6-Fc were coated on a 96-well high binding plate at 4 μg/mL in 1×PBS. The plate was incubated overnight at 4° C. and blocked with PBS +1% BSA. LGR5-Fc was diluted in primary buffer to 1 μg/mL, all in the presence or absence of 1 μg/mL of R-spondin 1/2/3/4 or 0.5 μg/mL of Norrin. R-spondin 1/2/3/4 or Norrin were preincubated together with hLGR5-Fc before being added to the ELISA plate. Triplicate wells were used for each condition was tested in triplicate. 1:2,000 anti-FLAG mAb (Cell Signaling) was used to detect bound hLGR5-Fc.1:10,000 dilution of anti-mouse IgG HRP (JIR) was used for detection. Plate was developed with TMB (Thermo), and data were collected on SpectraMax Plus 384 plate reader at 450 nm. Data analysis was done using GraphPad Prism 6 program. Formation of a ternary complex with LGR5, ligands RSPO or Norrin, and co-receptor (RNF43-Fc, ZNRF3-Fc, and LRP6-Fc) was observed.

Figure 14:
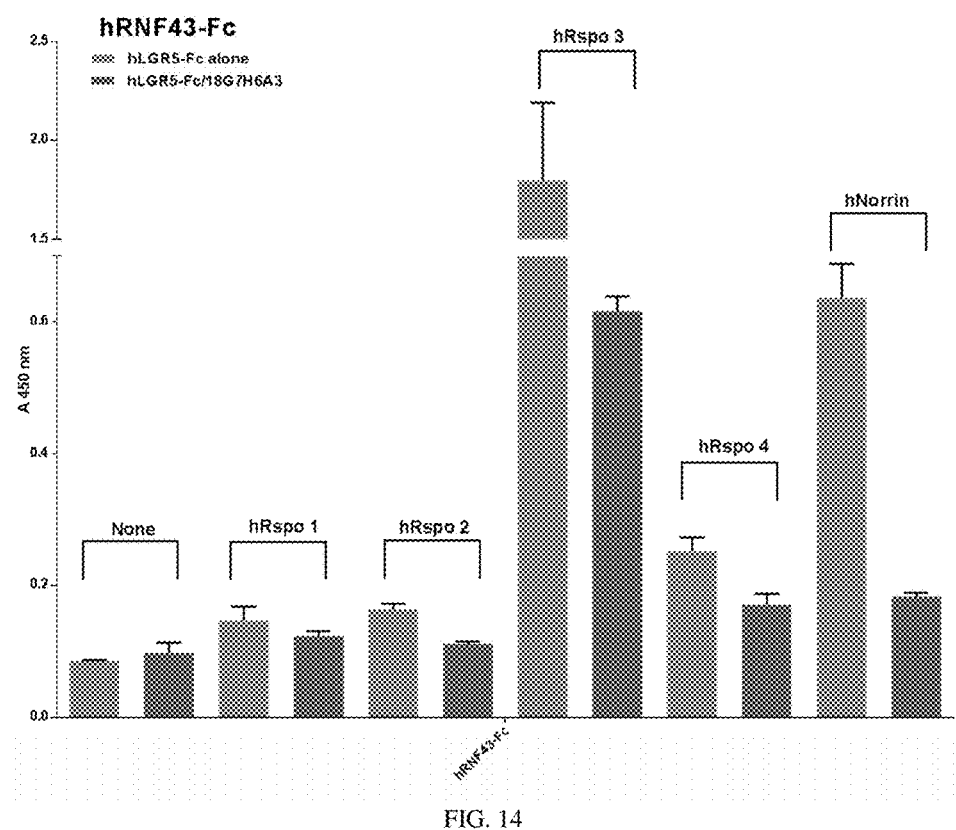
FIG. 14 is a bar chart showing that antibody 18G7H6A3 binding to LGR5 inhibits formation of ternary complex.

Next, 18G7H6A3 was added in addition to the ELISA plate in the presence of LGR5-Fc and RSPO or Norrin. 18G7H6A3 significantly reduced the formation of LGR5 ternary complexes with both RSPO and Norrin ligands as well as all three co-receptors (RNF43, ZNRF3, and LRP6). See FIG. 14. As 18G7H6A3 does not directly or competitively compete with ligand binding, this data is evidence of an allosteric model of inhibition.

Example 30

Epitope Mapping of Anti-LGR5 Antibody 18G7H6A3

To further characterize the specific region(s) of LGR5 that antibody 18G7H6A3 binds, an epitope mapping experiment was performed using hydrogen deuterium exchange mass spectrometry. Prior to conducting the hydrogen-deuterium exchange experiments, test digests prepared with undeuterated buffer in varying concentrations of guanidine hydrochloride (GdnHCl) were made to optimize proteolysis conditions for the best peptide coverage of LGR5 alone. For pepsin digestion for DXMS, a sample was thawed at 5° C. and then immediately digested over a protease column filled with porcine pepsin (Sigma) at a flow rate of 100 μl/min with 0.05% trifluoroacetic acid. Peptic fragments were collected on a C18 trap column and separated on a C18 reversed phase column (Vydac) with a linear acetonitrile gradient from 6 to 38%. The column effluent was electro sprayed directly into an LCQ Classic (Thermo Finnigan, Inc.) or Q-TOF mass spectrometer (Micromass). Determination of pepsin-generated peptides from MS/MS data sets was facilitated through the use of SEQUEST (Thermo Finnigan, Inc.). This set of peptides was then further verified by DXMS Explorer (Siena Analytics Inc., Modesto, Calif.). The peptide coverage maps for the different concentrations of GdnHCl were compared, and the condition with the best coverage map for each individual protein or protein complex was used for subsequent deuterium exchange experiments. All steps were performed at 0° C. as described previously.

Exchange experiments were initiated by mixing LGR5-Fc in protein buffer, or LGR5-Fc preincubated with 18G7H6A3 with D20 buffer to a final concentration of 50% D20. The mixtures were incubated at 0° C. for 10, 30, 100, 300, 1,000, 3,000, or 10,000 s and then the exchange reaction was quenched by adding ice-cold quench solution (0.96% formic acid, 0~0.8 M guanidine hydrochloride) resulting in samples with final concentrations of 0.58% formic acid and 0~0.5 M guanidine hydrochloride, pH 2.5. The samples were then immediately frozen on dry ice and stored at −80° C. Data processing of DXMS experiments utilized specialized software as previously described (DXMS Explorer, Sierra Analytics Inc.).

The hydrogen/deuterium (H/D)-exchange data provide details regarding changes in solvent exposure due to binding of 18G7H6A3 and the burying of surface exposed residues upon binding of antibody to antigen. The HD exchange data analysis indicates that 18G7H6A3 binds to amino acids T175, E176, Q180, R183, S186, A187, Q189, D247, E248, T251, R254, S257, N258, K260 of SEQ ID NO: 47 within the convex surface of leucine rich repeats 6-9, on the opposite of the face of the R-spondin binding site as identified by X-ray crystallographic studies. (See e.g., Chen et al. *Genes Dev.* 27(12):1345-50 which is incorporated by reference in its entirety). These data show that the residues involved in binding of LGR5 to the R-spondins are not involved in binding 18G7H6A3. These preliminary results do not preclude that fact that other structural elements in LGR5 may be involved in the binding site of 18G7H6A3.

Example 31

Administration of 18G7H6A3 to a Human Patient Suffering from Colon Cancer

A population of human patients suffering from colon cancer is treated with chemotherapy and tumor volume is monitored. It is observed that average tumor volume ceases to expand and in fact decreases upon initiation of chemotherapy. Following an extended duration of time, the tumor volume stabilizes and eventually begins to increase.

A second human patient population suffering from colon cancer is treated with chemotherapy co-administered with 18G7H6A3. Again, average tumor volume is monitored. It is observed that tumor volume ceases to expand and in fact decreases upon initiation of chemotherapy. It is observed that tumor volume decreases to a minimum volume that is substantially lower than that of the first population. It is also found that tumor size remains low for a substantially extended period of time relative to the first population.

Example 32

Administration of 18G7H6A1 to a Human Patient Suffering from Colon Cancer

A population of human patients suffering from colon cancer is treated with chemotherapy and tumor volume is monitored. It is observed that average tumor volume ceases to expand and in fact decreases upon initiation of chemotherapy. Following an extended duration of time, the tumor volume stabilizes and eventually begins to increase.

A second human patient population suffering from colon cancer is treated with chemotherapy co-administered with 18G7H6A1. Again, average tumor volume is monitored. It is observed that tumor volume ceases to expand and in fact decreases upon initiation of chemotherapy. It is observed that tumor volume decreases to a minimum volume that is substantially lower than that of the first population. It is also found that tumor size remains low for a substantially extended period of time relative to the first population.

Example 33

Administration of 18G7H6A3 to a Human Patient Suffering from Colon Cancer

A first population of human patients suffering from colon cancer is administered chemotherapy alone. A second population of human patients suffering from colon cancer is administered chemotherapy in combination with 18G7H6A3.

The first population demonstrates a temporary reduction in tumor size and growth, after which tumor growth resumes and symptoms return. Tumor growth after chemotherapy treatment is recalcitrant to subsequent chemotherapy treatments.

The second population demonstrates reduction in tumor size to a basal level and cessation of tumor growth. Tumor growth does not resume during or upon completion of a treatment regimen. After completion of the regimen, growth does not return and symptoms of the cancer are no longer present in the second population.

Example 34

Administration of 18G7H6A1 to a Human Patient Suffering from Colon Cancer

A first population of human patients suffering from colon cancer is administered chemotherapy alone. A second population of human patients suffering from colon cancer is administered chemotherapy in combination with 18G7H6A1.

The first population demonstrates a temporary reduction in tumor size and growth, after which tumor growth resumes and symptoms return. Tumor growth after chemotherapy treatment is recalcitrant to subsequent chemotherapy treatments.

The second population demonstrates reduction in tumor size to a basal level and cessation of tumor growth. Tumor growth does not resume during or upon completion of a treatment regimen. After completion of the regimen, growth does not return and symptoms of the cancer are no longer present in the second population.

Example 35

Administration of 18G7H6A3 to a Human Patient Suffering from Colon Cancer Increases Survival A first population of human patients suffering from colon cancer is administered chemotherapy alone. A second population of human patients suffering from colon cancer is administered chemotherapy in combination with 18G7H6A3.

Patient survival at a set duration after treatment (1 year) is monitored. It is observed that patient survival in the second population is substantially higher than patient survival in the first population. That is, a significantly higher proportion of the second population survives past the first year after treatment as compared to the survival rate of the first population.

Similar observations are made at later intervals, and it is observed that among survivors at the first interval, members of the second group are significantly more likely to survive to a second interval (2 years after treatment) that are members of the first group alive at 1 year post treatment.

Example 36

Administration of 18G7H6A1 to a Human Patient Suffering from Colon Cancer Increases Survival A first population of human patients suffering from colon cancer is administered chemotherapy alone. A second population of human patients suffering from colon cancer is administered chemotherapy in combination with 18G7H6A1.

Patient survival at a set duration after treatment (1 year) is monitored. It is observed that patient survival in the second population is substantially higher than patient survival in the first population. That is, a significantly higher proportion of the second population survives past the first year after treatment as compared to the survival rate of the first population.

Similar observations are made at later intervals, and it is observed that among survivors at the first interval, members of the second group are significantly more likely to survive to a second interval (2 years after treatment) that are members of the first group alive at 1 year post treatment.

Example 37

Administration of 18G7H6A3 to a Human Patient Suffering from Breast Cancer

A population of human patients suffering from breast cancer is treated with chemotherapy and tumor volume is monitored. It is observed that average tumor volume ceases to expand and in fact decreases upon initiation of chemotherapy. Following an extended duration of time, the tumor volume stabilizes and eventually begins to increase.

A second human patient population suffering from breast cancer is treated with chemotherapy co-administered with 18G7H6A3. Again, average tumor volume is monitored. It is observed that tumor volume ceases to expand and in fact decreases upon initiation of chemotherapy. It is observed that tumor volume decreases to a minimum volume that is substantially lower than that of the first population. It is also found that tumor size remains low for a substantially extended period of time relative to the first population.

Example 38

Administration of 18G7H6A1 to a Human Patient Suffering from Breast Cancer

A population of human patients suffering from breast cancer is treated with chemotherapy and tumor volume is monitored. It is observed that average tumor volume ceases to expand and in fact decreases upon initiation of chemotherapy. Following an extended duration of time, the tumor volume stabilizes and eventually begins to increase.

A second human patient population suffering from breast cancer is treated with chemotherapy co-administered with 18G7H6A1. Again, average tumor volume is monitored. It is observed that tumor volume ceases to expand and in fact decreases upon initiation of chemotherapy. It is observed that tumor volume decreases to a minimum volume that is substantially lower than that of the first population. It is also found that tumor size remains low for a substantially extended period of time relative to the first population.

Example 39

Administration of 18G7H6A3 to a Human Patient Suffering from Breast Cancer

A first population of human patients suffering from breast cancer is administered chemotherapy alone. A second population of human patients suffering from breast cancer is administered chemotherapy in combination with 18G7H6A3.

The first population demonstrates a temporary reduction in tumor size and growth, after which tumor growth resumes and symptoms return. Tumor growth after chemotherapy treatment is recalcitrant to subsequent chemotherapy treatments.

The second population demonstrates reduction in tumor size to a basal level and cessation of tumor growth. Tumor growth does not resume during or upon completion of a treatment regimen. After completion of the regimen, growth does not return and symptoms of the cancer are no longer present in the second population.

Example 40

Administration of 18G7H6A1 to a Human Patient Suffering from Breast Cancer

A first population of human patients suffering from breast cancer is administered chemotherapy alone. A second population of human patients suffering from breast cancer is administered chemotherapy in combination with 18G7H6A1.

The first population demonstrates a temporary reduction in tumor size and growth, after which tumor growth resumes and symptoms return. Tumor growth after chemotherapy treatment is recalcitrant to subsequent chemotherapy treatments.

The second population demonstrates reduction in tumor size to a basal level and cessation of tumor growth. Tumor growth does not resume during or upon completion of a treatment regimen. After completion of the regimen, growth does not return and symptoms of the cancer are no longer present in the second population.

Example 41

Administration of 18G7H6A3 to a Human Patient Suffering from Breast Cancer Increases Survival A first population of human patients suffering from breast cancer is administered chemotherapy alone. A second population of human patients suffering from breast cancer is administered chemotherapy in combination with 18G7H6A3.

Patient survival at a set duration after treatment (1 year) is monitored. It is observed that patient survival in the second population is substantially higher than patient survival in the first population. That is, a significantly higher proportion of the second population survives past the first year after treatment as compared to the survival rate of the first population.

Similar observations are made at later intervals, and it is observed that among survivors at the first interval, members of the second group are significantly more likely to survive to a second interval (2 years after treatment) that are members of the first group alive at 1 year pot treatment.

Example 42

Administration of 18G7H6A1 to a Human Patient Suffering from Breast Cancer Increases Survival A first population of human patients suffering from breast cancer is administered chemotherapy alone. A second population of human patients suffering from breast cancer is administered chemotherapy in combination with 18G7H6A1.

Patient survival at a set duration after treatment (1 year) is monitored. It is observed that patient survival in the second population is substantially higher than patient survival in the first population. That is, a significantly higher proportion of the second population survives past the first year after treatment as compared to the survival rate of the first population.

Similar observations are made at later intervals, and it is observed that among survivors at the first interval, members of the second group are significantly more likely to survive to a second interval (2 years after treatment) that are members of the first group alive at 1 year pot treatment.

Example 43

Administration of 18G7H6A3 to a Human Patient Suffering from Colon Cancer Decreases Side Effects A first population of human patients suffering from colon cancer is administered chemotherapy and an anti-LGR5 antibody that blocks LGR5-RSPO binding and signaling. A second population of human patients suffering from colon cancer is administered chemotherapy and 18G7H6A3.

The first population demonstrates non-therapeutic side effects associated with the interference of RSPO1 signaling through LGR5. These side-effects are detrimental to patient health.

The second population, administered 18G7H6A3 in combination with chemotherapy, does not demonstrate non-therapeutic side effects associated with the interference of RSPO1 signaling through LGR5.

Example 44

LGR5 Expression in Advanced CRC Tumors

LGR5 transcript expression was investigated using RNAscope technology with LGR5 specific probes. LGR5 transcript was detectable in tissues including colon, intestine, cerebellum and pancreas. LGR5 transcript was also detectable in patient derived xenograft (PDX) tissues including CT1 CRC and JH109 pancreatic tumors. LGR5 expression was investigated in CRC patient samples isolated at different stages of tumorigenesis including early (Grade-I) vs. advanced (Metastatic) lesions. LGR5 transcript was expressed in CRC Grade I, II and II lesions, and was highly expressed in CRC metastatic lesions.

Example 45

LGR54 Expression in Metastatic Pancreatic Patient Derived Xenografts

LGR5 expression in metastatic pancreatic patient derived xenografts was investigated using the quantitative polymerase chain reaction (QPCR). A sample of tumor tissue was flash frozen or added to a cryovial containing RNAlater (Qiagen, CA), and transferred to −70° C. after incubation at 4° C. for several hours. Total RNA was extracted using a Qiagen RNeasy extraction kit (Qiagen, CA), and cDNA was synthesized using a SuperScriptIII kit (Life Technologies, CA) and protocols provided by the manufacturer. Human LGR5 transcript abundance was measured using human specific LGR5 and GAPDH primers and the following thermal condition in the StepOne Thermocycler (Life Technologies, CA): 50° C. (2 min); 90° C. (2 min) and 40 cycles of 90° C. (15 sec) and 60° C. (1 min) and melt curve assessment (from 65° C.-95° C.). LGR5 abundance was quantified using $2^{\wedge}\delta Ct$ equation.

LGR5 was highly expressed in metastatic pancreatic patient derived xenografts. Treatment with chemotherapy resulted in increased LGR5 expression in pancreatic tumors. Using human specific primers, LGR5 transcript was measurable using QPCR in a series of pancreatic patient derived xenografts. While LGR5 was detectable in most tumors there was a trend for increased LGR5 expression in metastatic tumors further suggesting a role for LGR5 in advanced tumorigenesis.

Figure 15:
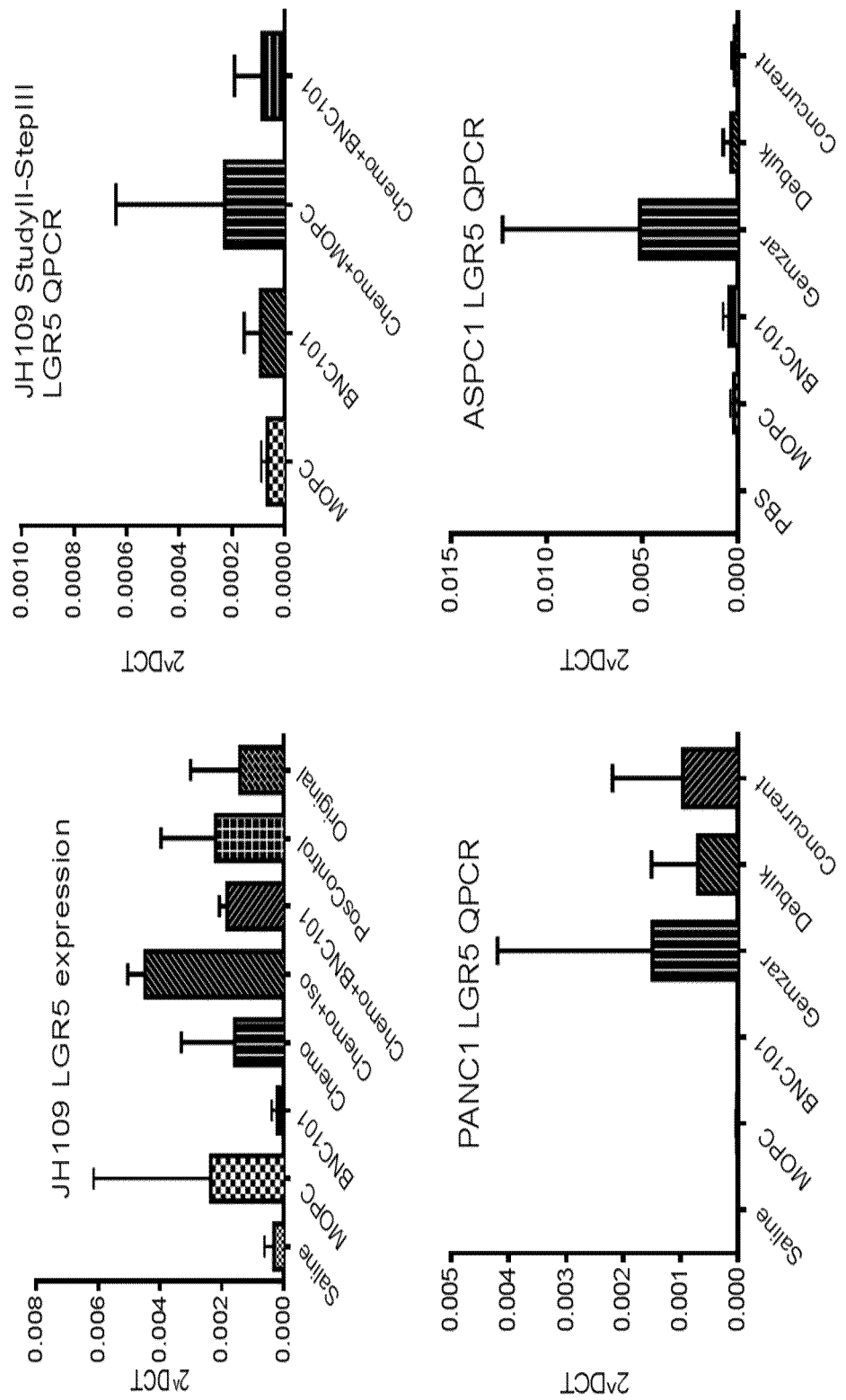
FIG. 15 depicts levels of LGR5 expression in treated samples.

LGR5 expression was investigated in a series of pancreatic tumors including JH109, ASPC1 and PANC1. Treatment with a standard of care treatment (SOC) (Gemzar and Abraxane in JH109 and Gemzar alone in PANC1 and ASPC1) resulted in an induction in LGR5 expression in each of the foregoing tumors (FIG. 15). Notably, LGR5 expression was reduced to levels comparable to controls (saline or MOPC) in tumors treated with combination of 18G7H6A3 and SOC. These data further indicate that LGR5 expression can serve as a biomarker of response to combination therapy (18G7H6A3+SOC) in PANC tumors.

Example 46

CTNNB1 is One of the 18G7H6A3 Target Genes in CRC and Pancreatic Tumors

Potential targets in the Wnt pathway for 18G7H6A3 were investigated. Wnt QPCR plates (Qiagen, CA) were prepared with primers for about 80 Wnt pathway genes in a 96 well PCR plate. cDNA from 18G7H6A3 or MOPC (control) treated tumors was pooled and QPCR in the Wnt plate was performed. Data in each plate was normalized to corresponding GAPDH and the abundance of each gene was measured using an $2^{\wedge}\delta Ct$ equation. To measure fold differences, data in each 18G7H6A3 treated tumor was divided by the corresponding value from MOPC treated group. Values above 1 or below 1 were indicative of upregulation or downregulation in 18G7H6A3 treated group, respectively.

Preliminary assessment of the number of genes that were up- or down-regulated showed that in both tumor models (CT1 and CT3) there were more downregulated genes than upregulated genes, suggesting 18G7H6A3 has an inhibitory effect on gene expression. Detailed analyses identified several differentially expressed genes including FZDB, FZD7, WNT7B, FBXW11, FZD1, DVL1, CSNK2A1 and CTNNB1.

Figure 16:
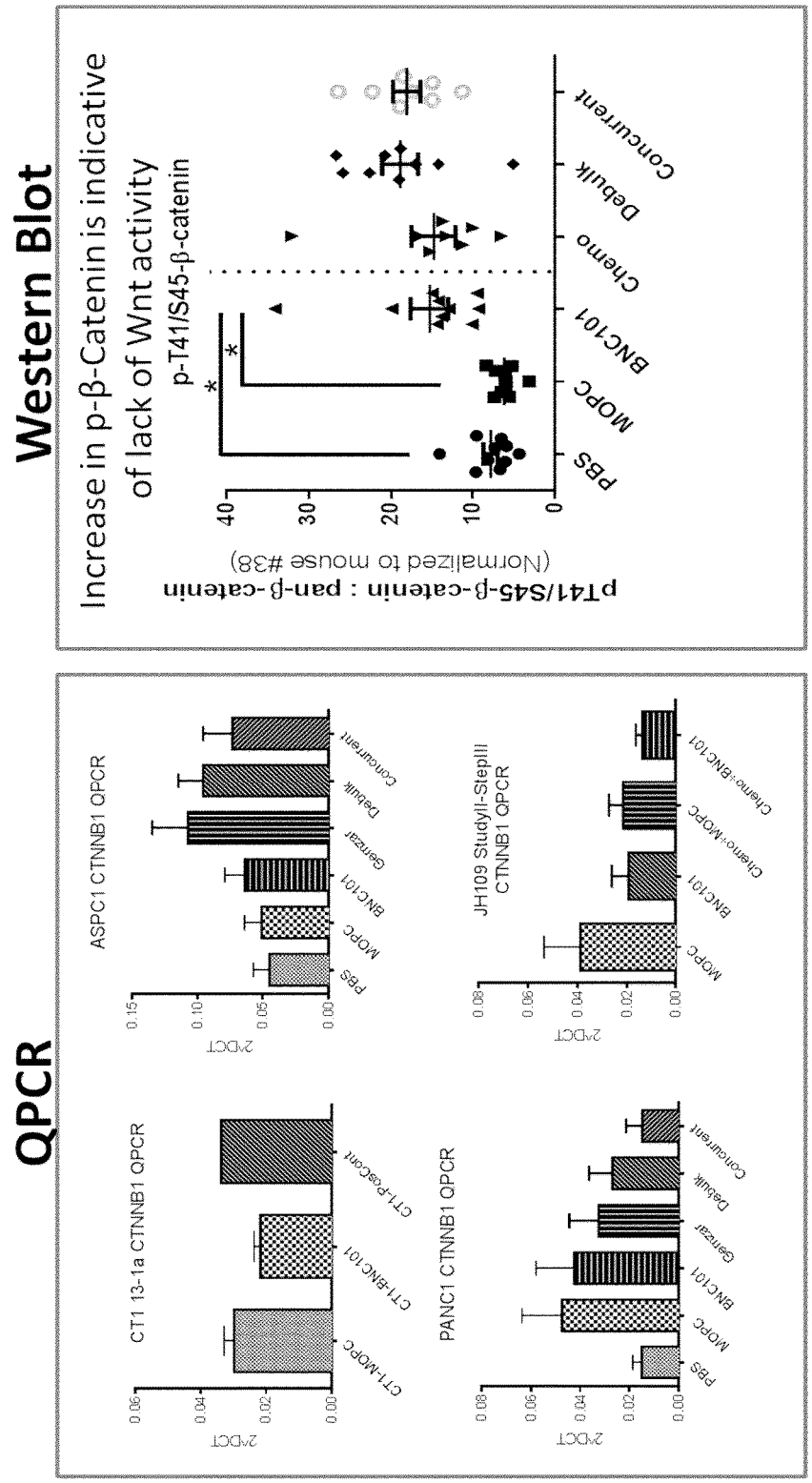
FIG. 16 depicts levels of CTNNB1 expression, and p-β-Catenin expression in treated samples.

In cervical cancer, there may be a close correlation between LGR5 expression and CTNNB1. In other studies, over-expression (using LGR5 recombinant vector) or downregulation of LGR5 (using shRNA) resulted in upregulation or downregulation of CTNNB1, respectively (Chen Q, Cao H Z, Zheng P S. 2014. Oncotarget 5: 9092-105). Additionally, analysis of immunohistochemical slides from cervical cancer patients showed a significant correlation between LGR5 and CTNNB1 expression. In this study, CTNNB1 expression was investigated further using QPCR (to measure transcript level) and Western Blotting (to assess protein expression). Using human specific primers, CTNNB1 expression was investigated in pancreatic and CRC tumors. Similar to LGR5 expression explained in Example 45, treatment with SOC increased CTNNB1 expression and the combination of 18G7H6A3 and SOC resulted in a reduction in CTNNB1 expression. Additionally, CTNNB1 expression was reduced about 35% in CT1 tumors treated with 18G7H6A3. Thus, treatment with 18G7H6A3 inhibits CTNNB1. Expression of β-catenin and phospho-β-catenin (indicative of lack of activity in Wnt pathway) was investigated by western blot analysis. Western blot data in ASPC1 tumors confirmed QPCR data in which 18G7H6A3 as single agent or in combination with SOC upregulated pβ-catenin suggesting inhibition of Wnt pathway activity in these tumors (FIG. 16).

Other components of the Wnt pathway including p-β-catenin, GSK-3β (total and phospho), and LRP6 were investigated in a series of CRC, pancreatic and breast tumors. Quantification of Western blot data showed significant inhibition of Wnt pathway signaling in ASPC1 and PANC1 tumors but also revealed some trends in favor of Wnt pathway downregulation in other models. BMCRC086 tumors that were not responsive to treatment with 18G7H6A3 were also negative for the expression of LGR5 and Wnt signaling pathway components, further supporting that the mechanism of action for 18G7H6A3 was specifically targeting LGR5 and inhibiting Wnt signaling.

Expression of Wnt pathway genes in pancreatic tumors including ASPC1, PANC1 and JH109 was investigated. Based on in vivo data, in both PANC1 and ASPC1 there was a difference in tumor volume between 18G7H6A3- vs. PBS-treated tumors. In contrast, JH109 tumors did not respond to a standard treatment regimen with either 18G7H6A3 single agent or SOC chemo combination. Differences in Wnt gene expression in responsive cells (PANC1 and ASPC1) and non-responsive cells (JH109) were investigated. In combo treated groups, Wnt6, FZD8, FOSL1, Wnt11, NFATC and FZD5 were downregulated in both ASPC1 and PANC1 combo-treated tumors, are were upregulated in JH109 tumors. In both the pancreatic and CRC data, genes including WNT11, WNT6, FRZB and PRICKEL were downregulated in PANC1, ASPC1, CT1 and CT3 cells, but not in JH109 cells.

Figure 17:
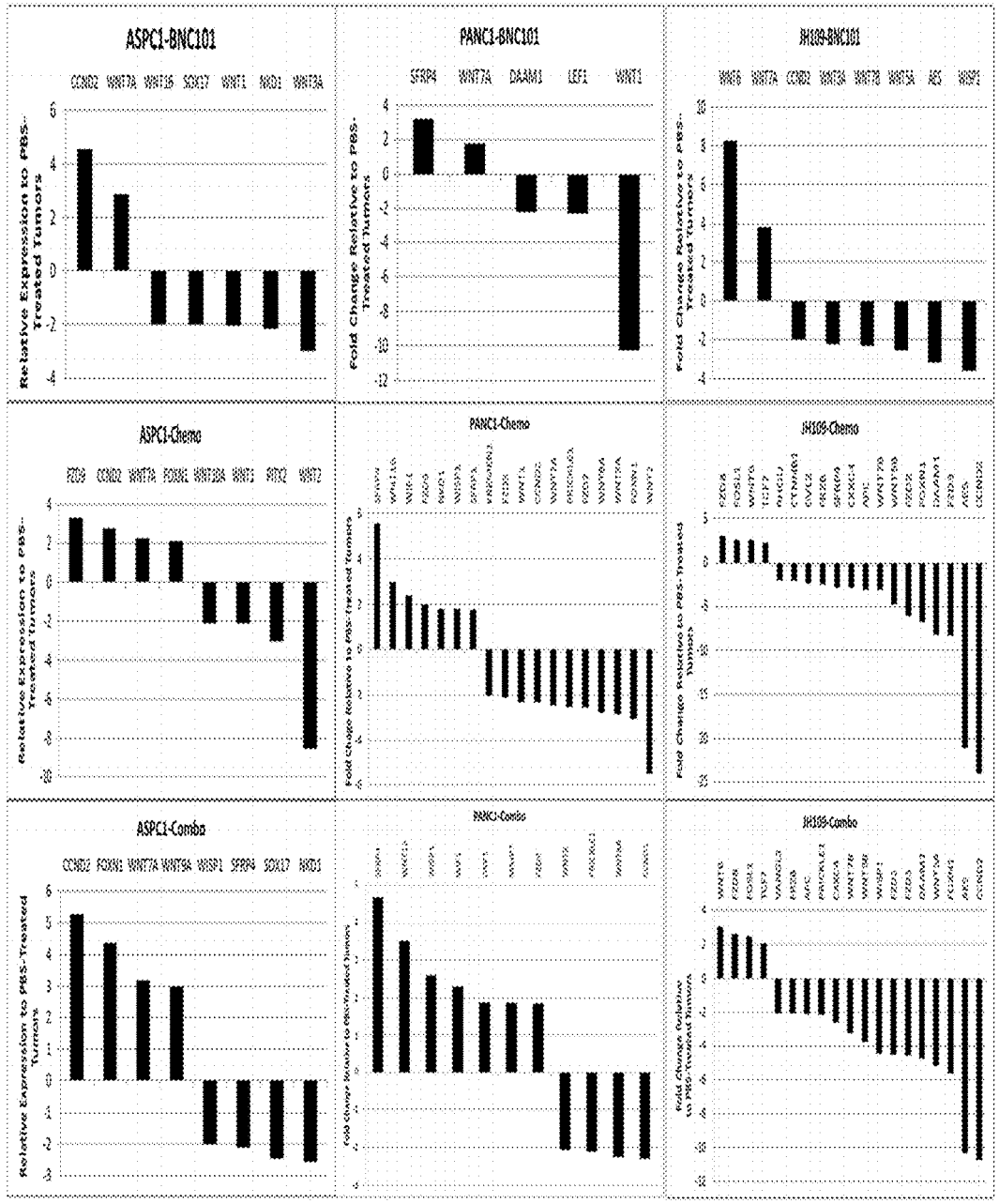
FIG. 17 depicts differentially expressed transcripts in various treated samples.

Gene Tree analysis identified potential genes co-regulated in pancreatic tumors treated with 18G7H6A3 that included Wnt11, FRAT1, LEF1, GSK3B, FZD8 and LRP6. Analysis of differentially expressed transcripts in each treatment also identified genes that were up/down regulated more than 2 fold in pancreatic tumors (FIG. 17). Some genes, such as Wnt7A, were common between all the tumors in 18G7H6A3 vs. control treated tumors.

Example 47

18G7H6A3 Inhibits Transcription in CT1 Tumors

Expression of 18G7H6A3-targeted genes were investigated in early vs. late tumorigenesis. Mice were implanted mice with CT1, and tumors were harvested from control, 18G7H6A3, FOLFIRI or combo groups at days 3, 10 and 17. Total RNA from each tumor at day-3 was harvested and prepared for gene array hybridization using Illumina human chips. Overall analysis of differentially expressed genes (more than 1.5 or 2 folds, p<0.05) showed that in tumors treated with 18G7H6A3 (as single agent or in combination with FOLFIRI) there are more downregulated genes than upregulated ones. This suggested that treatment with 18G7H6A3 may have had a more suppressive impact on overall cellular transcriptional machinery. PCA (Principal Component Analyses) also showed a proximity in overall gene expression in 18G7H6A3 and control treated tumors. However, when 18G7H6A3 was added to FOLFIRI (i.e. combo group) there was clear separation between combo vs. FOLFIRI suggesting that targeting LGR5 may have significantly changed gene expression in FOLFIRI-treated tumors.

Figure 18:
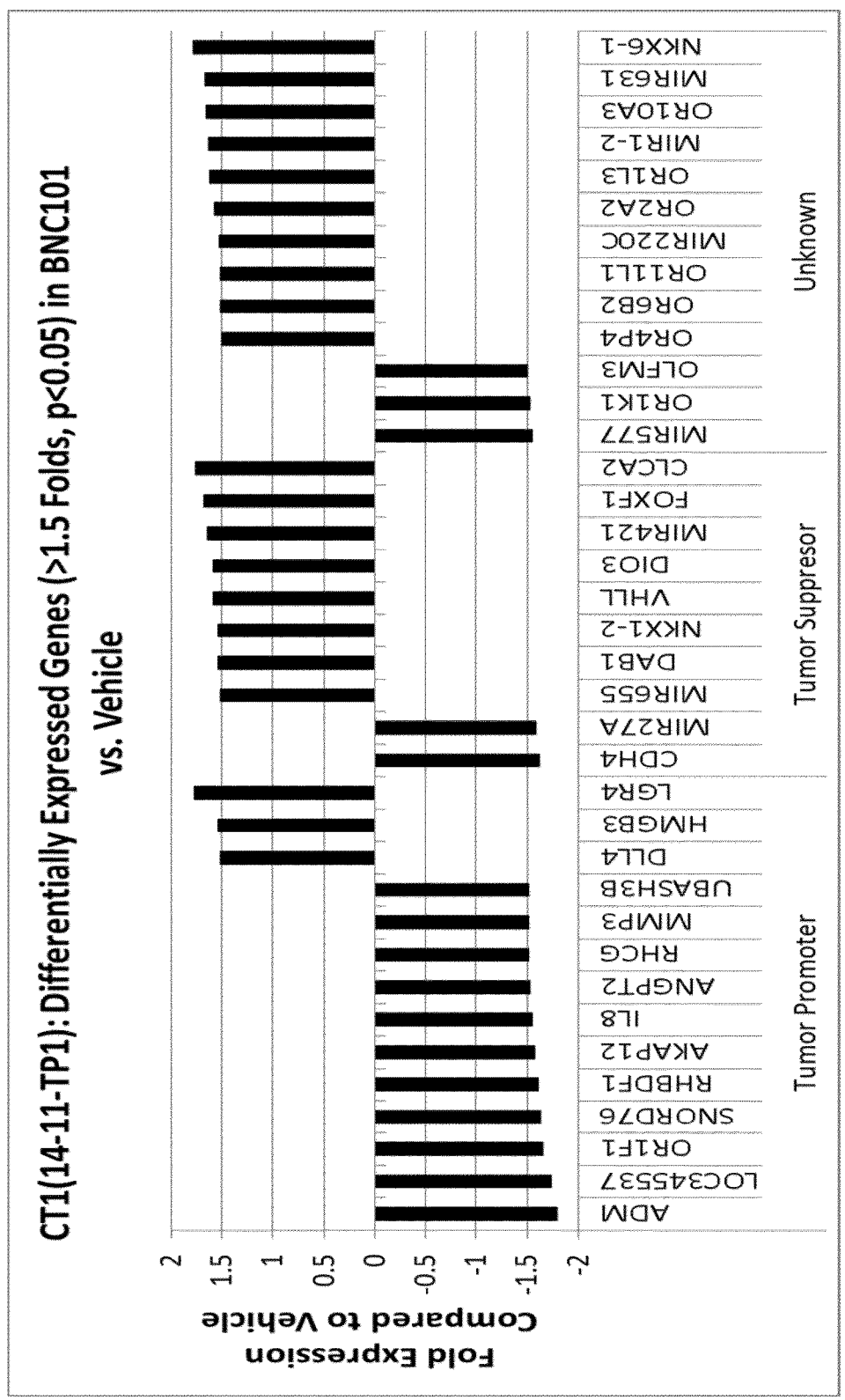
FIG. 18 depicts differentially expressed genes in 18G7H6A3− (BNC101) treated tumors.
Figure 19:
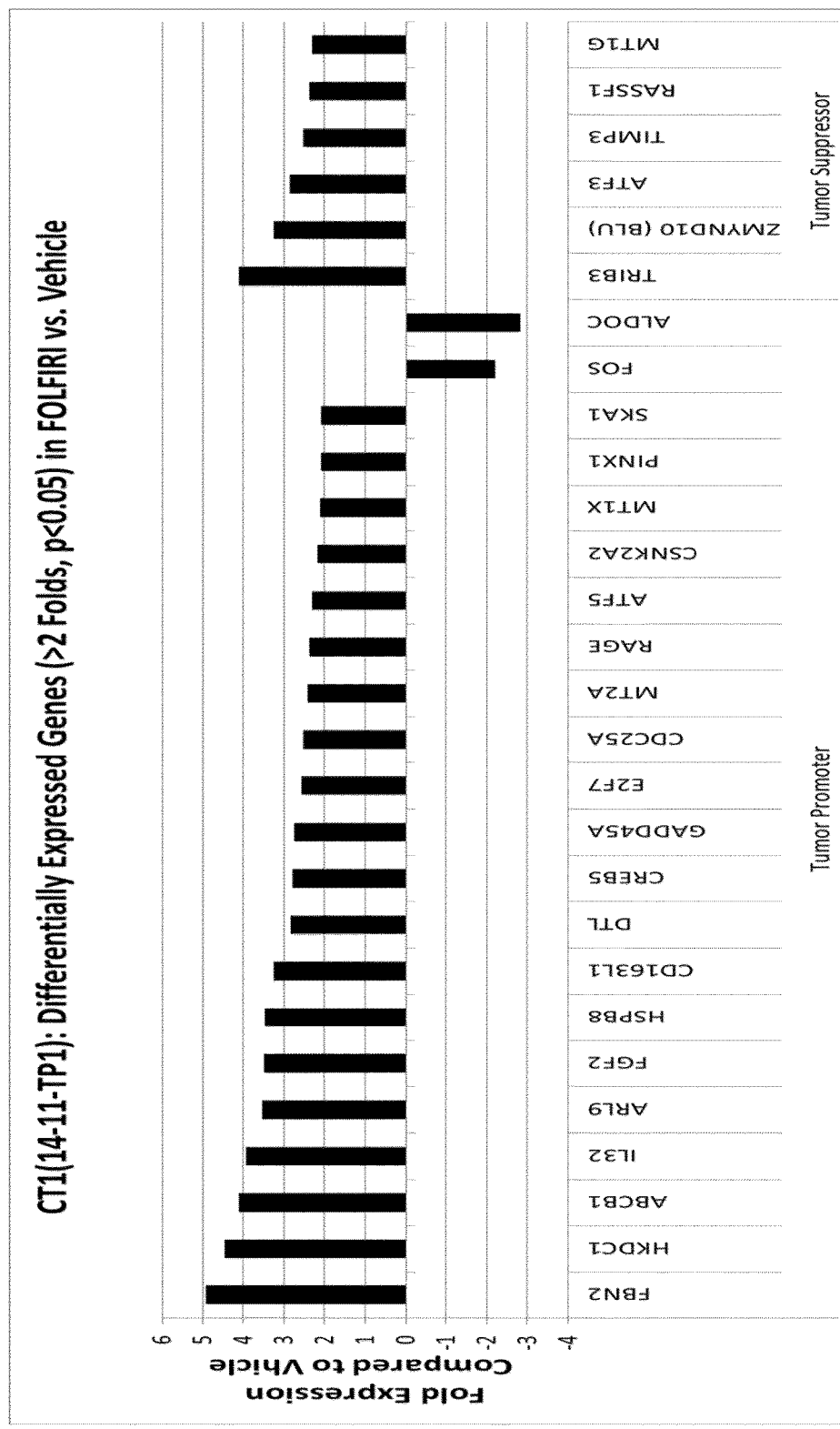
FIG. 19 depicts differentially expressed genes in FOLFIRI treated tumors.
Figure 20:
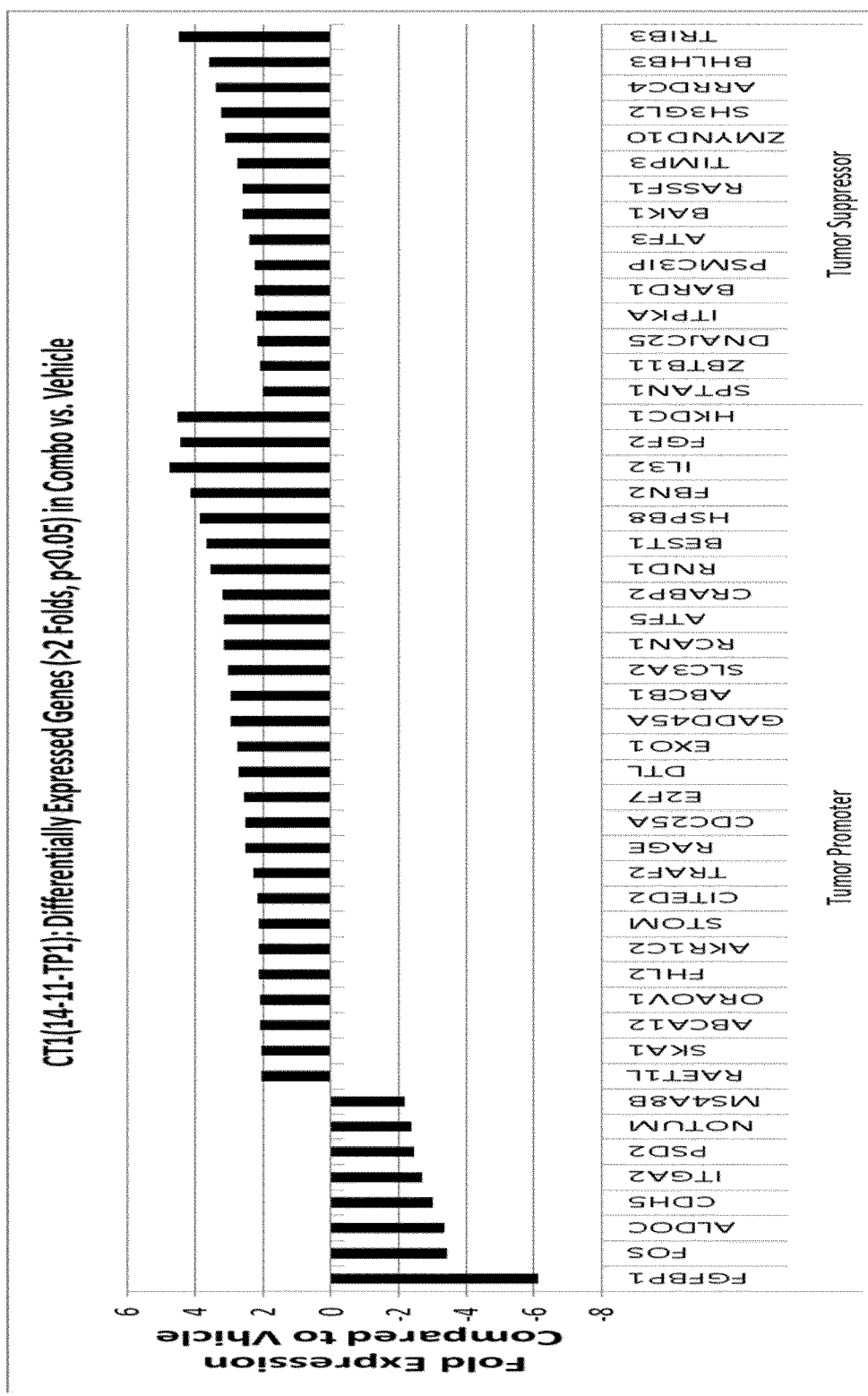
FIG. 20 depicts differentially expressed genes in combination-treated tumors

Analysis of differentially expressed genes in 18G7H6A3 vs. Vehicle identified several tumor promoters such as ANGPT2, AKAP12 and ADM that were downregulated in 18G7H6A3 treated tumors, and also several tumor suppressors such as DAB1, MIR655, NKX1-2 that were upregulated in 18G7H6A3 treated tumors (FIG. 18). Conversely FOLFIRI treatment appears to upregulate tumor promoters (FBN2, HKDC1, ABCB1, FGF2) and also some tumor suppressors such as TRIB3, ATF3 and TIMP3 (FIG. 19). Combination of FOLFIRI and 18G7H6A3 resulted in downregulation of more tumor promoters such as ALDOC, CDH5, ITGA2 and also upregulation of more tumor suppressors such as ZBTB11, ITPKA, PSMC3IP and BAK1 (FIG. 20).

Example 48

18G7H6A3 Treatment Significantly Reduces Human CTCs in Peripheral Blood in Orthotopic Models of Pancreatic Patient Derived Xenografts To investigate the role of 18G7H6A3 in inhibition of primary tumor growth and metastasis, LGR5 expression was examined in a series of pancreatic patient derived xenograft samples, and PANC1424 cells and PANC1427 cells.

Tumor samples were subcutaneously implanted in NOD/SCID (non-obese diabetic severe combined immunodeficient) mice and subsequently implanted into the pancreas in recipients designated for in vivo studies. Tumor volume was measured weekly in ultrasound and mice with tumors ~100 mm$^3$ were enrolled into the efficacy study and were treated with the followings: 1—MOPC isotype (15 mg/kg twice/week; ip); 2—18G7H6A3 (15 mg/kg twice/week; ip); 3—SOC (Gemzar 50 mg/kg; ip twice per week and Abraxane 30 mg/kg iv twice per week); 4—Combination of 18G7H6A3 and SOC at the above doses. At the end of the study, peripheral blood from each tumor bearing mouse was collected for CTC (using flow cytometry) and circulating DNA assessments. For flow cytometry, blood samples were treated with RBC lysis buffer (ACK buffer, Life Tech, CA) using manufacturer protocol and were stained with human HLA-FITC (eBiosciences, CA) and human LGR5-AF647 (BD Pharmingen, CA) for 30 min at 4° C. Cells were washed with staining buffer (PBS-FBS3%) twice and 7AAD (7-aminoactinomycin) prior to acquisition in the FACS calibur machine in the laboratory and the data were analyzed using FCS Express software (De Novo, CA).

Figure 21:
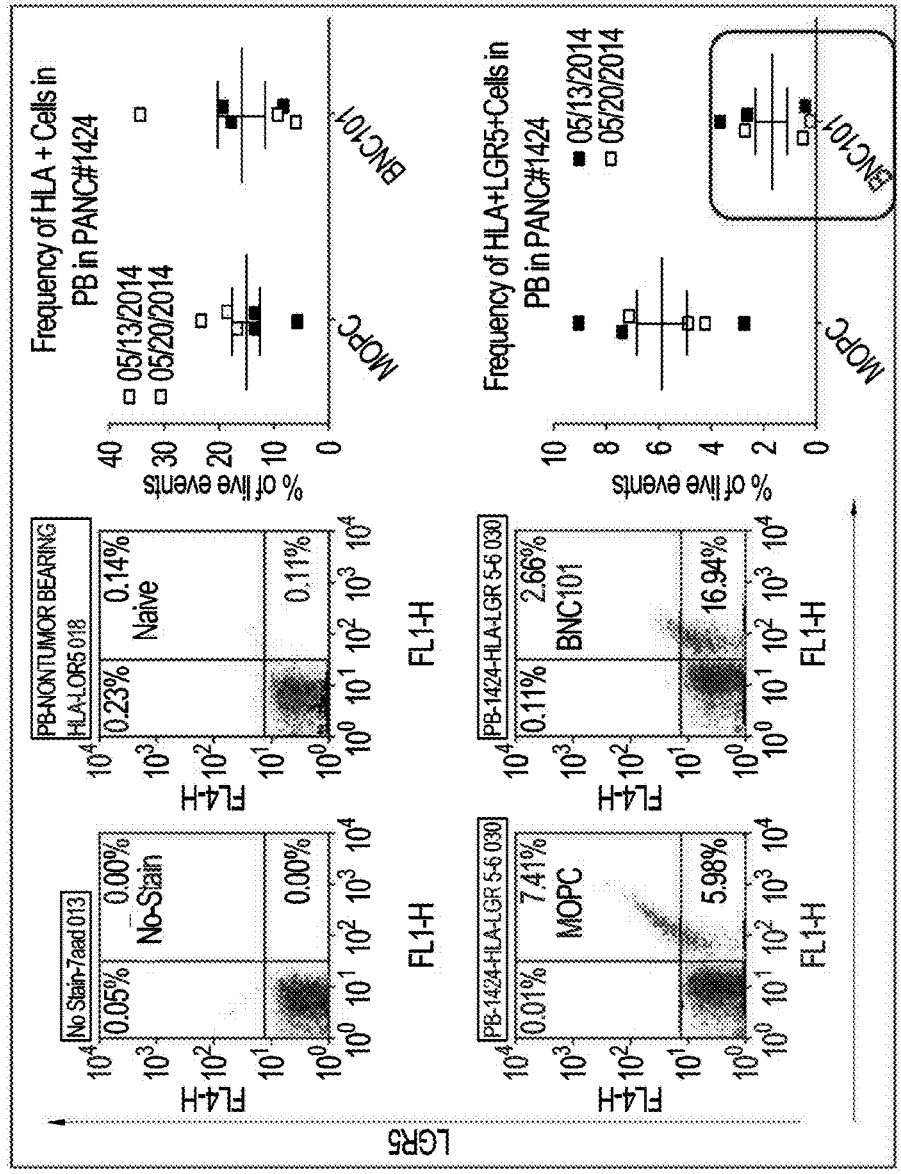
FIG. 21 depicts levels of LGR5 in circulating HLA+ cells.

LGR5 was expressed in various pancreatic patient derived xenograft samples. Human CTCs were detected in the peripheral blood. While percentage of HLA+ cells did not significantly change in MOPC vs. 18G7H6A3, the percentage of circulating HLA+LGR5+ cells was significantly reduced in 18G7H6A3 treated mice (FIG. 21).

Figure 22A:
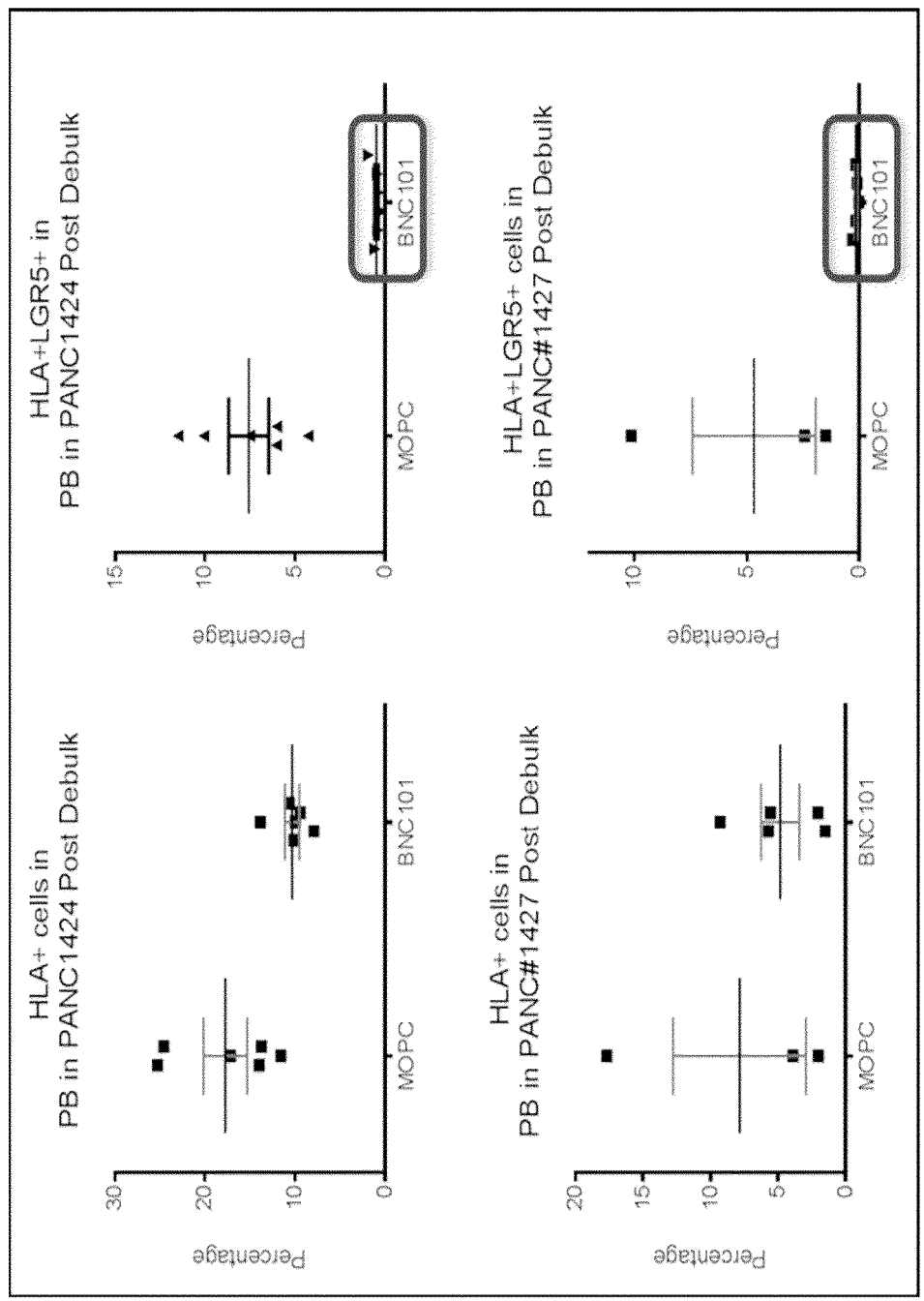
FIG. 22A and FIG. 22B depict levels of LGR5 in circulating HLA+ cells.
Figure 22B:
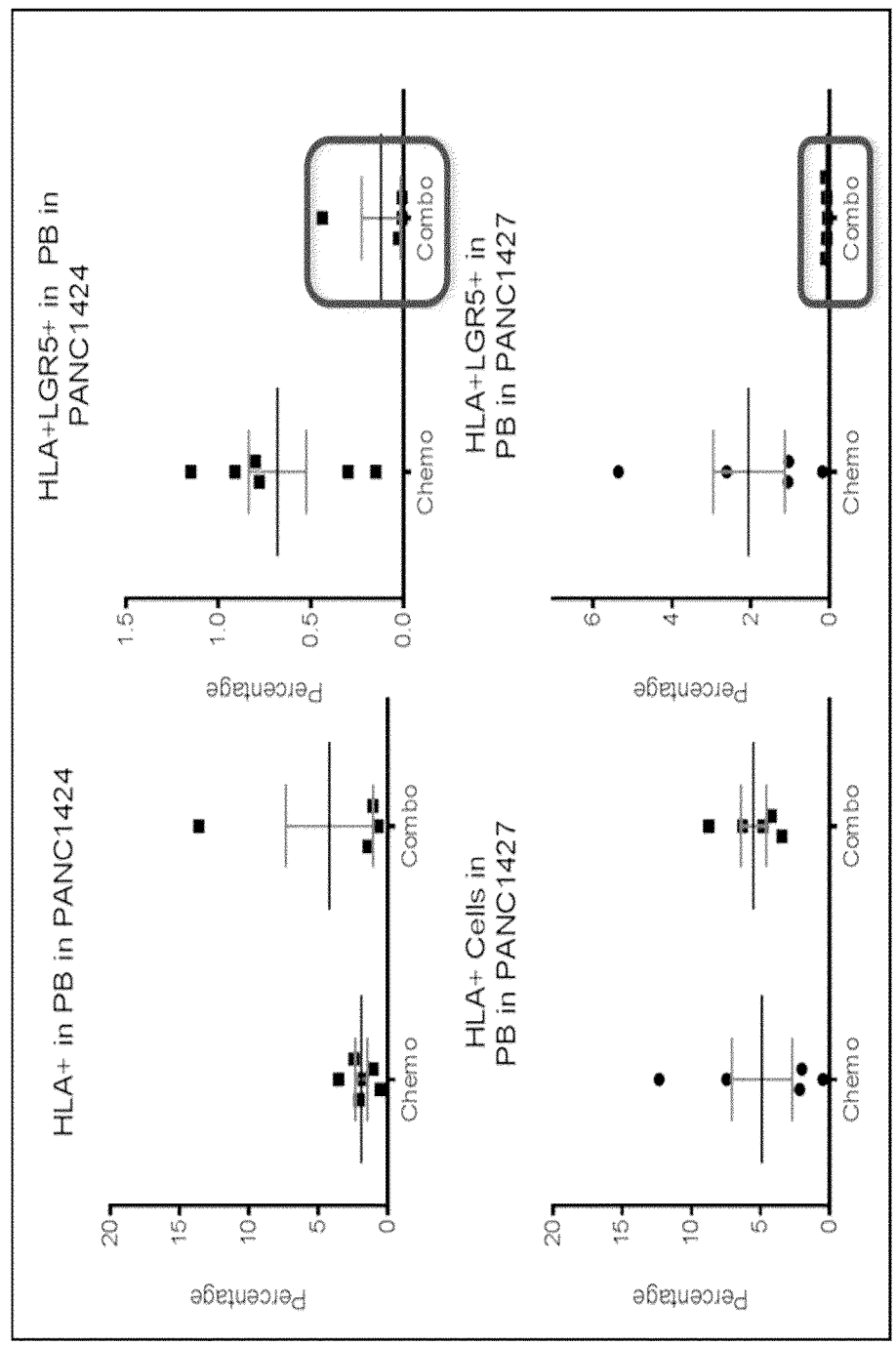

The percentage of HLA+ cells did not significantly change in chemo vs. combo treated mice, however, combination of 18G7H6A3 and SOC almost completely ablated HLA+LGR5+ cells in both concurrent and debulk settings (FIG. 22A, and FIG. 22B). 18G7H6A3 treatment (as single agent or in combination with SOC) significantly reduces human CTCs in peripheral blood in orthotopic models of pancreatic patient derives xenografts.

Example 49

LGR5 Expression in Other Models

LGF5 expression was investigated in skin samples from Cynomolgus macaques (Cynos) using flow cytometry and RNAscope. Skin samples from Cynos were treated with vehicle or various doses of 18G7H6A3 (G2:10 mg/kg; G3:50 mg/kg; and G4:150 mg/kg) at day 0, 7, 14 and 21. At study termination, skin samples were provided in DMEM supplemented with antibiotic (penicillin and streptomycin) and antimycotic solution (Anti-Anti 100×, Life Technologies, CA). Skin samples were digested using a cocktail of collagenases and thermolysin (Liberase, Roch Inc, CA). Skin progenitors (SPs) were isolated after overnight incubation with Liberase and mechanical disruption. SPs were stained with Rat anti-human LGR5 (AF647, BD Pharmingen, CA) and were analyzed in a calibur machine in the laboratory. Data analyses using FCS Express (Denovo Software, CA) showed that LGR5 was detectable in Cynos SPs, however, there was no significant difference in LGR5 frequency between 18G7H6A3 (at different doses) vs. vehicle treated group. Using RNAscope, LGR5 was detectable in skin areas especially in hair follicles and to a much lesser extent in skin epithelial cells. There was no significant difference in LGR5 positive area in vehicle vs. 18G7H6A3 treated samples.

Gene expression peripheral blood monocytes isolated from the Cynos was investigated. Total RNA was extracted using Qiagen RNeasy kit and cDNA was synthesized using Superscript cDNA Synthesis Kit (Life Technologies, CA). The cDNA from each treatment was pooled and was added to $RT^2$ Sybergreen qPCR master mix (SABiosciences, MA). The final mixture was added to each well of a 96-well plate containing Cyno QPCR primers for chemokines or inflammatory cytokines. PCR thermal profile included: 95° C. for 10 min and 40 cycles of 95° C. 15 sec and 60° C. 1 min followed by melt curve stage. Data (Ct values) in each plate was normalized by subtracting from the corresponding GAPDH and the abundance of each transcript was calculated using 2ADCT equation. Analyses of the number of transcripts differentially expressed (more than 2 folds) between any of the 18G7H6A3 group vs. vehicle treated group showed that, consistent with gene array data, there are much more downregulated genes than the upregulated ones. With dose escalation there were less upregulated genes and more downregulated genes. The G4-recovery (G4R) group in which Cynos did not receive any treatment for 4 weeks after the last dose of 18G7H6A3 showed almost similar number of up-down-regulated genes. Detailed analysis identified differentially expressed genes (CCL11, IL3, SPP1, CCL13, CXCL6 and TNFRSF11b) whose expression was inversely correlated with 18G7H6A3 dose i.e. highest in 10 mg/kg and lowest in 150 mg/kg.

Genes that were commonly downregulated between the treatments included CCL1, IFNγ, CCR8, IL2, IL3 and IL4, some of which are enriched in M1 or M2 macrophages.

Example 50

Inhibition of Small Cell Lung Cancer Tumor Growth In Vivo by a Humanized Anti-LGR5 Antibody Patient derived small cell lung cancer xenograft model. Dissociated tumor cells from BLG293 tumors were implanted into CB.17 SCID mice in Matrigel subcutaneously, and monitored twice weekly for tumor size and body weight. When tumors reached an average of 130 mm3, mice were randomized. Mice were treated with either PBS, antibody control MOPC, or 18G7H6A3. Mice were dosed BIW at 15 mg/kg for. All mice were monitored twice weekly for body weight and tumor size, as well as overall health and appearance, until termination.

18G7H6A3 showed significant anti-tumor activity compared to PBS (24.9% tumor growth inhibition) and MOPC antibody (24.7% tumor growth inhibition) controls.

Example 51

Figure 23:
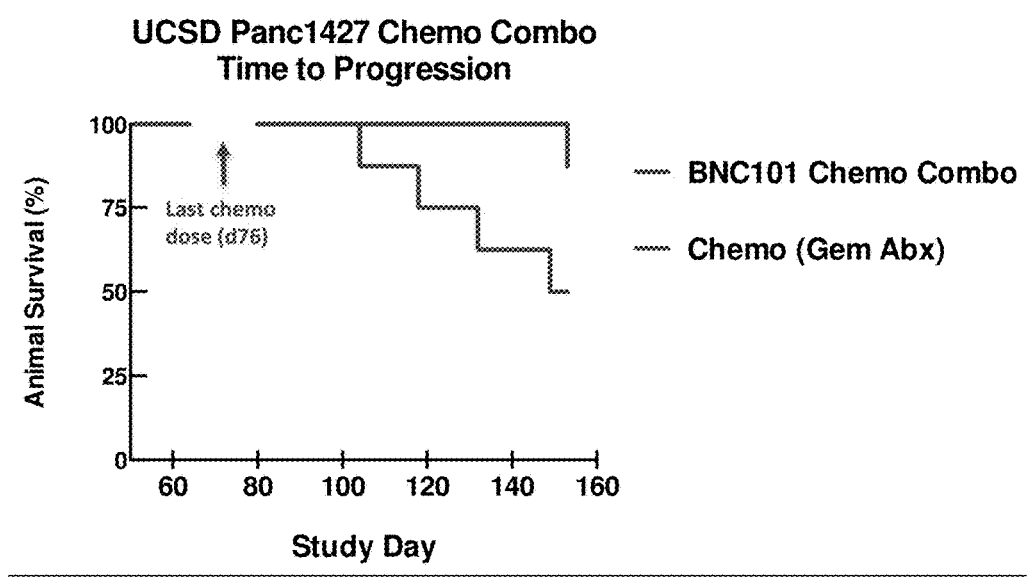
FIG. 23 is a graph showing animal survival of mice treated with Gemcitabine/Abraxane or with Gemcitabine/Abraxane and 18G7H6A3.

18G7H6A3 Increases Survival in Mice with Pancreatic Tumors that Relapse Following Debulk Chemotherapy Therapy Panc1427 (UCSD1427) tumors were completely debulked (regressed) by treatment with chemotherapy (Gemcitabine/Abraxane) and 18G7H6A3. When tumors were regressed, chemotherapy was removed and mice were treated with either 18G7H6A3 or no treatment. Animals treated with 18G7H6A3 were noticeably more healthy compared to the control animals, where several mice had to be euthanized due to severe health observations such as lameness or body weight loss. At day 150, 7/8 mice treated with 18G7H6A3 and chemotherapy were alive, versus 4/8 mice treated with chemotherapy alone. FIG. 23 summarizes the results.

The term "comprising" as used herein is synonymous with "including," "containing," or "characterized by," and is inclusive or open-ended and does not exclude additional, unrecited elements or method steps.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All references cited herein, including but not limited to published and unpublished applications, patents, and literature references, are incorporated herein by reference in their entirety and are hereby made a part of this specification. To the extent publications and patents or patent applications incorporated by reference contradict the disclosure contained in the specification, the specification is intended to supersede and/or take precedence over any such contradictory material.

What is claimed is:

1. A human or humanized antibody or epitope-binding fragment thereof that specifically binds human leucine-rich repeat containing G-protein-coupled receptor 5 (LGR5), and comprises activity to inhibit growth of a human colon tumor cell in vivo, wherein the antibody comprises:
    a heavy chain complementary determining region 1 (CDR1) comprising an amino acid sequence shown in SEQ ID NO:23;
    a heavy chain complementary determining region 2 (CDR2) comprising an amino acid sequence shown in SEQ ID NO:25;
    a heavy chain complementary determining region 3 (CDR3) comprising an amino acid sequence shown in SEQ ID NO:27;
    a light chain CDR1 comprising an amino acid sequence shown in SEQ ID NO:29;
    a light chain CDR2 comprising an amino acid sequence shown in SEQ ID NO:31; and
    a light chain CDR3 comprising an amino acid sequence shown in SEQ ID NO:33.

2. The human or humanized antibody of claim 1 comprising:
    a heavy chain variable domain selected from the group consisting of SEQ ID NOs: 19 and 48; or
    a light chain variable domain selected from the group consisting of SEQ ID NOs: 21 and 49.

3. The human or humanized antibody of claim 1 comprising:
    a heavy chain selected from the group consisting of SEQ ID NOs: 13 and 10; or
    a light chain selected from the group consisting of SEQ ID NOs: 14 and 9.

4. The human or humanized antibody of claim 1, wherein the antibody binds to an epitope comprising a residue of SEQ ID NO: 47 selected from the group consisting of T175, E176, Q180, R183, S186, A187, Q189, D247, E248, T251, R254, S257, N258, and K260.

5. The human or humanized antibody of claim 1, wherein the antibody lacks specific binding to a rodent LGR5.

6. The human or humanized antibody of claim 1, wherein the antibody does not disrupt binding between LGR5 and RSPO.

7. The human or humanized antibody of claim 6, wherein the RSPO is selected from the group consisting of: RSPO1, RSPO2, RSPO3, and RSPO4.

8. The human or humanized antibody of claim 1, wherein the antibody disrupts formation of an LGR5-RSPO-LRP6 complex.

9. The human or humanized antibody of claim 1, having an EC50 for human LGR5 binding that is less than 10 nM and greater than or equal to 300 pM.

10. The humanized antibody of claim 1, wherein the humanized antibody comprises activity to inhibit growth of a human neoplastic cell in vivo, wherein the neoplastic cell is selected from the group consisting of: lung tumor cell, breast tumor cell, and pancreatic tumor cell.

11. The human or humanized antibody of claim 1, wherein the humanized antibody comprises activity to inhibit growth of a human neoplastic cell in vivo, wherein the neoplastic cell is selected from the group consisting of: a triple negative breast cancer cell, a colon cancer cell having a mutation in a gene selected from the group consisting of K-Ras, H-Ras, APC, PI3K, PTEN, p53, STK11, RB1, TP53, FGFR2, VANGL2, and ISCO, and a small cell lung cancer cell.

12. The human or humanized antibody of claim 1, wherein the human colon tumor cell is a cancer stem cell.

13. The human or humanized antibody of claim 12, wherein the cancer stem cell expresses a CD44 or a CD166 marker on its surface.

14. The human or humanized antibody of claim 1 comprising:
    a heavy chain variable domain comprising SEQ ID NO: 19; and
    a light chain variable domain comprising SEQ ID NO: 21.

15. A pharmaceutical composition comprising the human or humanized antibody of claim 1 and a pharmaceutically acceptable carrier.

16. A human or humanized antibody or epitope-binding fragment thereof that specifically binds human leucine-rich repeat containing G-protein-coupled receptor 5 (LGR5), and comprises activity to inhibit growth of a human colon tumor cell in vivo, wherein the antibody comprises:
    a heavy chain complementary determining region 1 (CDR1) comprising an amino acid sequence as shown in SEQ ID NO:23, or conservative variations thereof;
    a heavy chain complementary determining region 2 (CDR2) comprising an amino acid sequence as shown in SEQ ID NO:25;
    a heavy chain complementary determining region 3 (CDR3) comprising an amino acid sequence as shown in SEQ ID NO:27;
    a light chain CDR1 comprising an amino acid sequence as shown in SEQ ID NO:29;
    a light chain CDR2 comprising an amino acid sequence as shown in SEQ ID NO:31; and
    a light chain CDR3 comprising an amino acid sequence as shown in SEQ ID NO:33.

17. The human or humanized antibody of claim 16, wherein the heavy chain CDR1 comprises an amino acid sequence as shown in SEQ ID NO:23 with conservative substitutions thereof.

18. The human or humanized antibody of claim 16, wherein the heavy chain CDR1 comprises a polypeptide having at least 90% identity with an amino acid sequence as shown in SEQ ID NO:23.

19. The human or humanized antibody of claim 16, wherein the heavy chain CDR1 comprises one or more conservative substitutions at a residue as shown in SEQ ID NO:23 and selected from the group consisting of the third residue, the fifth residue, and the sixth residue.

* * * * *